US010941428B2

(12) United States Patent
Rubio Herrero et al.

(10) Patent No.: US 10,941,428 B2
(45) Date of Patent: Mar. 9, 2021

(54) REAGENTS AND METHODS FOR THE EXPRESSION OF AN ACTIVE NIFB PROTEIN AND USES THEREOF

(71) Applicant: UNIVERSIDAD POLITÉCNICA DE MADRID, Madrid (ES)

(72) Inventors: Luis Manuel Rubio Herrero, Madrid (ES); Stefan Burén, Madrid (ES); Xi Jiang, Madrid (ES); Carlos Echavarri Erasun, Madrid (ES); Gema López Torrejón, Madrid (ES)

(73) Assignee: UNIVERSIDAD POLITÉCNICA DE MADRID, Madrid (ES)

( * ) Notice: Subject to any disclaimer, the term of this patent is extended or adjusted under 35 U.S.C. 154(b) by 52 days.

(21) Appl. No.: 16/161,487

(22) Filed: Oct. 16, 2018

(65) Prior Publication Data
US 2020/0080117 A1   Mar. 12, 2020

(30) Foreign Application Priority Data
Sep. 12, 2018   (EP) .................................... 18382654

(51) Int. Cl.
C12P 21/02 (2006.01)
C12P 13/24 (2006.01)
C07K 14/21 (2006.01)
C12N 9/88 (2006.01)

(52) U.S. Cl.
CPC .............. *C12P 13/24* (2013.01); *C07K 14/21* (2013.01); *C12N 9/88* (2013.01); *C07K 2319/07* (2013.01); *C07K 2319/40* (2013.01)

(58) Field of Classification Search
CPC ................................ C12P 21/02; C07K 14/21
USPC ....................................................... 435/107
See application file for complete search history.

(56) References Cited

U.S. PATENT DOCUMENTS

| 4,945,050 | A | 7/1990 | Sanford et al. |
| 5,004,863 | A | 4/1991 | Umbeck |
| 5,063,154 | A | 11/1991 | Fink et al. |
| 5,104,310 | A | 4/1992 | Saltin |
| 5,141,131 | A | 8/1992 | Miller et al. |
| 5,159,135 | A | 10/1992 | Umbeck |
| 5,177,010 | A | 1/1993 | Goldman et al. |
| 5,378,619 | A | 1/1995 | Rogers |
| 5,384,253 | A | 1/1995 | Krzyzek et al. |
| 5,451,513 | A | 9/1995 | Maliga et al. |
| 5,463,175 | A | 10/1995 | Barry et al. |
| 5,472,869 | A | 12/1995 | Krzyzek et al. |
| 5,545,818 | A | 8/1996 | McBride et al. |
| 5,589,617 | A | 12/1996 | Nehra et al. |
| 5,591,616 | A | 1/1997 | Yokoh et al. |
| 5,693,507 | A | 12/1997 | Daniell et al. |
| 5,877,402 | A | 3/1999 | Maliga et al. |
| 5,932,479 | A | 8/1999 | Daniell et al. |
| 6,100,447 | A | 8/2000 | Wu et al. |
| 6,541,257 | B2 | 4/2003 | Lemaux et al. |

FOREIGN PATENT DOCUMENTS

| AU | 6178194 A | 9/1994 |
| AU | 667939 B2 | 4/1996 |
| CA | 2092588 A1 | 9/1994 |
| EP | 0120516 B1 | 10/1991 |
| WO | WO 87/06614 A1 | 11/1987 |
| WO | WO 92/09696 A1 | 6/1992 |
| WO | WO 93/21335 A2 | 10/1993 |
| WO | WO 95/24492 A1 | 9/1995 |
| WO | WO 97/048814 A2 | 12/1997 |
| WO | WO 99/05265 A2 | 2/1999 |
| WO | WO 99/14314 A1 | 3/1999 |

OTHER PUBLICATIONS

Abdullah, R., et al., Efficient Plant Regeneration from Rice Protoplasts Through Somatic Embryogenesis, Bio/Technology, vol. 4, pp. 1087-1090, 1986.

Allen, R.M., et al., Incorporation of Iron and Sulfur from NifB Cofractor into the Iron-Molybdenum Cofactor in Dinitrogenase, Journal of Biological Chemistry, vol. 270, No. 45, pp. 26890-26896, 1995.

Allen, R.S. ,et al., Expression of 16 Nitrogenase Proteins within the Plant Mitochondrial Matrix, Frontiers in Plant Science, vol. 8, Article 287, 14 pages, 2017.

Arragain, S., et al., Diversity and Functional Analysis of the FeMo-Cofactor Maturase NifB, Frontiers in Plant Science, vol. 8, Article 1947, 17 pages, 2017.

Beinert, H., Semi-Micro Methods for Analysis of Labile Sulfide and of Labile Sulfide Plus Sulfane Sulfur in Unusually Stable Iron-Sulfur Proteins, Analytical Biochemistry, vol. 131, pp. 373-378, 1983.

Berman, J., et al Expression of Nitrogen Fixation Genes in Foreign Hosts, The Journal of Biological Chemistry, vol. 260, No. 9, pp. 5240-5243, 1985.

Bevan, M. et al., Structure and Transcription of Nopaline Synthase Gene Region of T-DNA, Nucleic Acids Research, vol. 11, No. 2, pp. 369-385, 1983.

Bulen, W.A., et al., The Nitorgenase System From Azotbacter: Two-Enzyme Requirement for N2 Reduction, ATP-Depended, $H_2$ Evolution and ATP Hydrolysis, Biochemistry, vol. 56, pp. 979-986, 1966.

Burén, S., et al., Formation of Nitrogenase NifDK Tetramers in the Mitochondria of *Saccharomyces cerevisiae*, ACS Synthetic Biology, vol. 6, pp. 1043-1055, 2017.

Burén, S., et al., Purification and In Vitro Activity of Mitochondria Target Nitorgenase Cofactor Maturase NifB, Frontiers in Plant Science, vol. 8, Article 1567, 53 pages, 2017.

(Continued)

*Primary Examiner* — Tekchand Saidha

(74) *Attorney, Agent, or Firm* — Knobbe, Martens, Olson & Bear, LLP

(57) ABSTRACT

The invention relates to reagents and methods that allow the expression of an active NifB protein in yeast and plants under aerobic conditions. The active NifB protein allows the in vitro synthesis of the FeMo cofactor (FeMo-co) which leads to the subsequent apo-NifDK activation and generation of active nitrogenase.

10 Claims, 22 Drawing Sheets

Specification includes a Sequence Listing.

(56) References Cited

OTHER PUBLICATIONS

Burén, S., Eukaryotic expression of nitrogenase cofactor maturase NifB, 13th European Nitrogen Fixation Conference (ENFC), Stockholm, Sweden, Aug. 18-21, 2018.

Burén, S., On the road to making nitrogen fixing plants, 13th European Nitrogen Fixation Conference (ENFC), Stockholm, Sweden, Aug. 18-21, 2018.

Abstract Book, 13th European Nitrogen Fixation Conference (ENFC), Stockholm, Sweden, Aug. 18-21, 2018.

Candat, A., et al., The Ubiquitous Distribution of Late Embryogenesis Abundant Proteins Across Cell Compartments in *Aradiopsis* Offers Tailored Protection Against Abiotic Stress, Plant Cell, vol. 26, pp. 3148-3166, 2014.

Capecchi, M., High Efficiency Transformation by Direct Microinjection of DNA into Cultured Mammalian Cells, Cell, vol. 22, pp. 479-488, 1980.

Carlson, P.S., et al., Forced Association Between Higher Plant and Bacterial Cells in Vitro, Nature, vol. 252, pp. 393-395, 1974.

Christiansen, J., et al., Catalytic and Biophysical Properties of a Nitrogenize Apo-MoFe Protein Produced by a Nif-B-Deletion Mutant of Azotobacter vinelandii, Biochemistry, vol. 37, pp. 12611-12623, 1998.

Clapp, D.W., Somatic gene Therapy into Hematopoietic Cells, Clinics in Perinatology, vol. 20, No. 1, pp. 155-168, 1993.

Curatti, L., et al., NifB-dependent in vitro synthesis of the iron—molybdenum cofactor of nitrogenase, Proceedings of the National Academy of Sciences of the U.S.A., vol. 103, No. 14, 5297-5301, 2006.

Curiel, D.T., et al., High-Efficiency Gene Transfer Mediated by Adenovirus Coupled to DNA-Polylysine Complexes, Human Gene Therapy, vol. 3, pp. 147-154, 1992.

Diekert, K., et al., Isolation and Subfractionation of Mitochondria from the Yeast *Saccharomyces cerevisiae*, Methods in Cell Biology, vol. 65, pp. 37-51, 2001.

Dobereiner, J., et al., Nitrogenize Activity and Oxygen Sensitivity of the Paspalum notatum-Azotobacter paspali Association, Journal of General Microbiology, vol. 71, pp. 103-116, 1972.

Echavarri-Erasun, C., et al., Expression and Purification of NifB Proteins from Aerobic and Anaerobic Sources, Juan C. Fontecilla-Camps and Yvain Nicolet (eds.), Springer Science+Business Media New York, *Metalloproteins: Methods and Protocols*, Methods in Molecular Biology, Chapter 3, vol. 1122, 14 pages, 2014.

Egener, T., et al., Use of Green Fluorescent Protein to Detect Expression of nif Genes of *Azoarcus* sp. BH72, a Grass-Associated Diazotroph, on Rice Roots, Molecular Plant-Microbe Interactions, vol. 11, No. 1, pp. 71-75, 1998.

Eglitis, M.A., et al., Retroviral-Mediated Gene Transfer Into Hemopietic Cells, Advances in Experimental Medicine and Biology, vol. 241, pp. 19-27, 1998.

Emerich, D., et al., Interactions of Heterologous Nitrogenase Components That Generate Catalytically Inactive Complexes, Proceedings of the National Academy of Sciences of the U.S.A., vol. 73, pp. 4369-4373, 1976.

Emerich, D., et al., Complementary Functioning of the Component Proteins of Nitrogenase from Several Bacteria, Journal of Bacteriology, vol. 134, pp. 936-943, 1978.

Fay, A.W., et al., Identification and Characterization of Functional Homologs of Nitrogenase Cofactor Biosynthesis Protein Nifb from Methanogens, Proceedings of the National Academy of Sciences of the U.S.A., vol. 112, pp. 14829-14833, 2015.

Feng, L., et al., High-Level Expression and Mutagenesis of Recombinant Human Phosphatidylcholine Transfer Protein Using a Synthetic Gene: Evidence for a C-Terminal Membrane Binding Domain, Biochemistry, vol. 39, No. 50, pp. 15399-15409, 2000.

Fish, W., Rapid Colorimetric Micromethod for the Quantitation of Complexed Iron in Biological Samples Methods Enzymol, vol. 158, pp. 357-364, 1988.

Fujimura, T., et al., Regeneration of Rice Plants from Protoplasts, Plant Tissue Culture Letters, vol. 2, pp. 74-75, 1985.

Gietz, R.D., et al., Quick and Easy Yeast Transformation Using the LiAc/SS Carrier DNA/PEG Method, Nature Protocols, vol. 2, pp. 35-37, 2007.

Graham, F.L., et al., Transformation of Rat Cells by DNA of Human Adenovirus 5, Virology, vol. 54, No. 2, pp. 536-539, 1973.

Guo, Y., et al., The Nitrogenase FeMo-Cofactor Precursor Formed by NifB Protein: A Diamagnetic Cluster Containing Eight Iron Atoms, Angewandte Chemie International edition in English, vol. 55, pp. 12764-12767, 2006.

Herrera-Estrella, L., et al., Expression for Chimaeric Genes Transferred into Plant Cells Using a Ti-Plasmid-Derived Vector, Nature, vol. 303, pp. 209-213, 1983.

Hill, D., et al., Protein Determination Using Bicinchoninic Acid in the Presence of Sulfhydryl Reagents', Analytical Biochemistry, vol. 170, pp. 203-208, 1988.

Huang, Z., et al., A DNA Replicon System for Rapid High-Level Production of Virus-Like Particles in Plants, Biotechnology and Bioengineering, vol. 103, pp. 706-714, 2009.

Humphreys, D., et al., High-Level Periplasmic Expression in *Escherichia coli* Using a Eukaryotic Signal Peptide: Importance of Codon Usage at the 59 End of the Coding Sequence, Protein Expression and Purification, vol. 20, pp. 252-264, 2000.

Hurek, T., et al., Augmented Rates of Respiration and Efficient Nitrogen Fixation at Nanomolar Concentrations of Dissolved $O_2$ in Hyperinduced *Azoarcus* sp. Strain BH72, Journal of Bacteriology, vol. 176, No. 15, pp. 4726-4733, 1994.

Hurek, T., et al., Root Colonization and Systemic Spreading of *Azoarcus* sp. Strain BH72 in Grasses, Journal of Bacteriology, vol. 176, No. 7, pp. 1913-1923, 1994.

Hurek, T., et al., Azoarcus Grass Endophytes Contribute Fixed Nitrogen to the Plant in an Unculturable State, MPMI, vol. 15, No. 3, pp. 233-242, 2002.

Jeanthon, C., et al., *Methanococcus infernus* Sp. Nov., A Novel Hyperthermophilic Lithotrophic Methanogen Isolated From a Deep-Sea Hydrothermal Vent, International Journal of Systematic and Evolutionary Microbiology, vol. 48, pp. 913-919, 1998.

Jiménez-Vicente, E., et al., Role of Azotobacter vinelandii FdxN in FeMo-co Biosynthesis, FEBS Letters, vol. 588, pp. 512-516, 2014.

Kay, R., et al., Duplication of CaMV 35S Promoter Sequences Creates a Strong Enhancer for Plant Genes, Science, vol. 236, pp. 1299-1302, 1987.

Kennedy, C., et al., Genetics of Azotobacters: Applications to Nitrogen Fixation and Related Aspects of Metabolism, Annual Review of Microbiology Journal, vol. 41, pp. 227-258, 1987.

Kennedy, M., et al., The Role of Iron in the Activation-Inactivation of Aconitase, Journal of Biological Chemistry, vol. 258, pp. 11098-11105, 1983.

Köhler, R. H., et al., The Green Fluorescent Protein as a Marker to Visualize Plant Mitochondria In Vivo, The Plant Journal, vol. 11, No. 613-621, pp. 1365-313, 1997.

Leuzinger, K., et al., Efficient Agroinfiltration of Plants for High-level Transient Expression of Recombinant Proteins, Journal of Visualized Experiments, vol. 77, e50521, 2013.

López-Torrejón, G., et al., Expression of a Functional Oxygen-Labile Nitrogenase Component in the Mitochondrial Matrix of Aerobically Grown Yeast, Nature Communications, vol. 7, 11426, 6 pages, 2015.

Lu, L., et al., High Efficiency Retroviral Mediated Gene Transduction into Single Isolated Immature and Replatable CD343 + Hematopoietic Stem/Progenitor Cells from Human Umbilical Cord Blood, Journal of Experimental Medicine, vol. 178, No. 6, pp. 2089-2096, 1993.

Maiti, I. B., et al., Promoter/Leader Deletion Analysis and Plant Expression Vectors With the Figwort Mosaic Virus (FMV) Full Length Transcript (Flt) Promoter Containing Single or Double Enhancer Domains, Transgenic Research, vol. 6, pp. 143-156, 1997.

McBride, K.E., et al., Amplification of a Chimeric Bacillus Gene in Chloroplasts Leads to an Extraordinary Level of an Insecticidal Protein in Tobacco, Bio/Technology NY, vol. 13, No. 4, pp. 362-365, 1995.

McElroy, D., et al., Isolation of an Efficient Actin Promoter for Use in Rice Transformation, Plant Cell, pp. 163-171, 1990.

(56) References Cited

OTHER PUBLICATIONS

Millar, A.H., et al., Isolation and Sub fractionation of Mitochondria from Plants, Methods Cell Biology, vol. 80, pp. 65-90, 2007.
Narum, D., et al., Codon Optimization of Gene Fragments Encoding Plasmodium Falciparum Merzoite Proteins Enhances DNA Vaccine Protein Expression and Immunogenicity in Mice Infection and Immunity, vol. 69, No. 12, pp. 7250-7253, 2001.
Nelson, B.K., et al., A Multicolored Set of In Vivo Organelle Markers for Co-Localization Studies in *Arabidopsis* and Other Plants, Plant Journal, vol. 51, pp. 1126-1136, 2007.
Nioh, I., Nitrogen Fixation and a Nitrogen-Fixing Bacterium From the Roots of Eragrostis Ferruginea, The Journal of General and Applied Microbiology, vol. 25, pp. 261-271, 1979.
Outchkourov, N., et al., Optimization of the Expression of Equistatin in Pichia Pastoris, Protein Expression and Purification, vol. 24, No. 1, pp. 18-24, 2002.
Pan, R., et al., The *Arabidopsis* Mitochondrial Membrane-Bound Ubiquitin Protease UBP27 Contributes to Mitochondrial Morphogenesis, Plant Journal, vol. 78, pp. 1047-1059, 2014.
Prankeviciuaus, A., et al., Bacterial Dinitrogen Fixation in the Leaf of the Northern Pitcher Plant (*Sarracenia purp urea*), Canadian Journal of Botany, vol. 69, pp. 2296-2298, 1991.
Rettberg, L., et al., Radical S-Adenosyl-L-Methionine (SAM) Enzyme Involved in the Maturation of the Nitrogenas Cluster, Methods in Enzymology, vol. 606, pp. 341-361, 2018.
Rodriguez-Quinones, F., et al., Expression of the Nififdxnrnfoq Region of Azotobacter Vinelandii and Its Role in Nitrogenase Activity, Journal of Bacteriology, vol. 175, pp. 2926-2935, 1993.
Rubio, L., Expression of Nitrogenase Biosynthetic Proteins in Eukaryotes: Implications for Engineering N-fixing Cereals James Hutton Institute, Dundee, 2018.
Rubio, L., et al., Engineering Nitrogenase Assembly in Eukaryotes, Joyn Bio, 2018.
Rubio, L. Functional Expression of Nitrogenase Structural and Biosynthetic Proteins in Yeast Mitochondria, Nitrogen Network Meeting, Oxford, 2018.
Sadoff, H., et al., Characterization of Azotobacter vinelandii Deoxyribonucleic Acid and Folded Chromosomes, Journal of Bacteriology, vol. 138, No. 3, pp. 871-877, 1979.
Schmidt, T.G.M., et al., Development of the Twin-Strep-Tag_ and Its Application for Purification of Recombinant Proteins From Cell Culture Supernatants, Protein Expression and Purification, vol. 92, pp. 54-61, 2013.
Shah, V.K., et al., Simple Method of Purification of Homogeneity of Nitro-Genase Components from Aztobacter Vinelandii, Biochimica et Biophysica Acta, vol. 305, pp. 445-454, 1973.
Shah V.K., et al., In Vitro Synthesis of the Iron-Molybdenum Cofactor of Nitrogenase, Journal of Biological Chemistry, vol. 269, pp. 1154-1158, 1994.
Sprent, J., et al., Legume Evolution: Where Do Nodules and Mycorrhizas Fit In?, Plant Physiology, vol. 144, pp. 575-581, 2007.
Staub, J., et al., Marker Rescue From the Nicotania Tabacum Plastid Genome Using Plastid, *Escherichi coli* Shuttle Vector, MGG—Molecular and General Genetics, vol. 249, No. 1, pp. 37-42, 1995.
Staub, J., et al., Expression of Chimeric Uid a Gene Indicates that Polycistronic mRNAs are efficiently translated in Tobacco Plastids, The Plant Journal, vol. 7, No. 5, pp. 845-848, 1995.
Stewart, W., et al., In Situ Studies on N2 Fixation Using the Acetylene Reduction Technique, Proceedings of the National Academy of Sciences of the U.S.A., vol. 58, pp. 2071-2078, 1967.
Toriyama, K., et al., Haploid and Dipolid Plant Regeneration from Protoplasts of Another Callus in Rice, Theoretical and Applied Genetics, vol. 73, pp. 16-19, 1986.
Vasil. V., et al., The Biology of Azospirillum-sugarcane Association I. Establishment of the Association, Z. Pflanzenphysiol. Bd. 95. S. 141-147, 1979.
Vickers, C.E., et al., pGFPGUSPlus, A New Binary Vector for Gene Expression Studies and Optimising Transformation Systems in Plants, Biotechnology Letters, vol. 29, pp. 1793-1796, 2007.
Vögtle, F.N., et al., Global Analysis of the Mitochondrial N-Proteome Identifies a Processing Peptidase Critical for Protein Stability, Cell, vol. 139, pp. 428-439, 2009.
Wagner, E., et al.,Coupling of Adenovirus to Transferrin-Polylysine/DNA Complexes Greatly Enhances Receptor-Mediated Gene Delivery and Expression of Transfected Genes, Proceedings of the National Academy of Sciences of the United States of America of the U.S.A., vol. 89, No. 13, pp. 6099-6103, 1992.
Westermann, B., et al., Mitochondria-targeted Green Fluorescent Proteins: Convenient Tools for the Study of Organelle Biogenesis in *Saccharomyces cerevisiae*, Yeast, vol. 16, pp. 1421-1427, 2000.
Wilcoxen, J., et al., Electron Paramagnetic Resonance Characterization of Three Iron-Sulfur Clusters Present in the Nitrogenase Cofactor Maturase NifB from Methanocaldococcus infernus, Journal of the American Chemical Society, vol. 138, pp. 7468-7471, 2016.
Witte, C.P., et al., Rapid One-Step Protein Purification From Plant Material Using the Eight-Amino Acid Strepii Epitope, Plant Molecular Biology, vol. 55, pp. 135-147,2004.
Wiig, J.A., et al., Radical SAM-Dependent Carbon Insertion into the Nitrogenase M-Cluster, Science, vol. 337, pp. 1672-1675, 2012.
Wiig, J.A., et al., NifEN-B Complex of Azotobacter Vinelandii is Fully Functional in Nitrogenase Femo Cofactor Assembly, Proceedings of the National Academy of Sciences of the U.S.A., vol. 108, pp. 8623-8627, 2011.
Zhao, D., et al., Evidence for nifU and nifS Participation in the Biosynthesis of the Iron-Molybdenum Cofactor of Nitrogenase*, Journal of Biological Chemistry. vol. 282, pp. 37016-37025, 2007.
Curatti, L., et al. In vitro synthesis of the iron-molybdenum cofactor of nitrogenase from iron, sulfur, molybdenum, and homocitrate using purified proteins, PNAS, vol. 104, No. 45, pp. 17626-17631, 2007.

SEQUENCE LISTING

```
<160> NUMBER OF SEQ ID NOS: 58

<210> SEQ ID NO 1
<211> LENGTH: 69
<212> TYPE: PRT
<213> ORGANISM: Artificial sequence
<220> FEATURE:
<223> OTHER INFORMATION: mitochondrial targeting peptide

<400> SEQUENCE: 1

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30
```

```
Lys Arg Thr Ile Gln Thr Gly Ser Pro Leu Gln Thr Leu Lys Arg Thr
            35                  40                  45

Gln Met Thr Ser Ile Val Asn Ala Thr Thr Arg Gln Ala Phe Gln Lys
    50                  55                  60

Arg Ala Tyr Ser Ser
65

<210> SEQ ID NO 2
<211> LENGTH: 29
<212> TYPE: PRT
<213> ORGANISM: Artificial sequence
<220> FEATURE:
<223> OTHER INFORMATION: mitochondrial targeting peptide

<400> SEQUENCE: 2

Met Leu Ser Leu Arg Gln Ser Ile Arg Phe Phe Lys Pro Ala Thr Arg
1               5                   10                  15

Thr Leu Cys Ser Ser Arg Tyr Leu Leu Gln Gln Lys Pro
            20                  25

<210> SEQ ID NO 3
<211> LENGTH: 28
<212> TYPE: PRT
<213> ORGANISM: Artificial sequence
<220> FEATURE:
<223> OTHER INFORMATION: peptide tag

<400> SEQUENCE: 3

Trp Ser His Pro Gln Phe Glu Lys Gly Gly Ser Gly Gly Gly Gly Ser
1               5                   10                  15

Gly Gly Ser Ala Trp Ser His Pro Gln Phe Glu Lys
            20                  25

<210> SEQ ID NO 4
<211> LENGTH: 8
<212> TYPE: PRT
<213> ORGANISM: Artificial sequence
<220> FEATURE:
<223> OTHER INFORMATION: peptide tag

<400> SEQUENCE: 4

Trp Ser His Pro Gln Phe Glu Lys
1               5

<210> SEQ ID NO 5
<211> LENGTH: 6
<212> TYPE: PRT
<213> ORGANISM: Artificial sequence
<220> FEATURE:
<223> OTHER INFORMATION: peptide tag

<400> SEQUENCE: 5

Ala His Gly His Arg Pro
1               5

<210> SEQ ID NO 6
<211> LENGTH: 14
<212> TYPE: PRT
<213> ORGANISM: Artificial sequence
<220> FEATURE:
<223> OTHER INFORMATION: peptide tag

<400> SEQUENCE: 6

Pro Ile His Asp His Asp His Pro His Leu Val Ile His Ser
```

```
                   1               5                        10

<210> SEQ ID NO 7
<211> LENGTH: 7
<212> TYPE: PRT
<213> ORGANISM: Artificial sequence
<220> FEATURE:
<223> OTHER INFORMATION: peptide tag
<220> FEATURE:
<221> NAME/KEY: misc_feature
<222> LOCATION: (5)..(6)
<223> OTHER INFORMATION: Xaa can be any naturally occurring amino acid

<400> SEQUENCE: 7

Gly Met Thr Cys Xaa Xaa Cys
1               5

<210> SEQ ID NO 8
<211> LENGTH: 6
<212> TYPE: PRT
<213> ORGANISM: Artificial sequence
<220> FEATURE:
<223> OTHER INFORMATION: tetracysteine motif
<220> FEATURE:
<221> NAME/KEY: misc_feature
<222> LOCATION: (3)..(4)
<223> OTHER INFORMATION: Xaa can be any naturally occurring amino acid

<400> SEQUENCE: 8

Cys Cys Xaa Xaa Cys Cys
1               5

<210> SEQ ID NO 9
<211> LENGTH: 37
<212> TYPE: PRT
<213> ORGANISM: Artificial sequence
<220> FEATURE:
<223> OTHER INFORMATION: mitochondrial targeting peptide

<400> SEQUENCE: 9

Met Leu Arg Thr Arg Thr Thr Lys Thr Leu Ser Thr Val Ala Arg Thr
1               5                   10                  15

Thr Arg Ala Ile Gln Tyr Tyr Arg Ser Ile Ala Lys Thr Ala Ala Val
            20                  25                  30

Ser Gln Arg Arg Phe
        35

<210> SEQ ID NO 10
<211> LENGTH: 40
<212> TYPE: PRT
<213> ORGANISM: Artificial sequence
<220> FEATURE:
<223> OTHER INFORMATION: mitochondrial targeting peptide

<400> SEQUENCE: 10

Met Leu Lys Leu Ser Arg Ser Ala Asn Leu Arg Leu Val Gln Leu Pro
1               5                   10                  15

Ala Ala Arg Leu Ser Gly Asn Gly Ala Lys Leu Leu Thr Gln Arg Gly
            20                  25                  30

Phe Phe Thr Val Thr Arg Leu Trp
        35                  40

<210> SEQ ID NO 11
<211> LENGTH: 33
<212> TYPE: PRT
<213> ORGANISM: Artificial sequence
```

```
-continued

<220> FEATURE:
<223> OTHER INFORMATION: mitochondrial targeting peptide

<400> SEQUENCE: 11

Met Leu Ser Arg Ile Val Ser Asn Asn Ala Thr Arg Ser Val Met Cys
1               5                   10                  15

His Gln Ala Gln Val Gly Ile Leu Tyr Lys Thr Asn Pro Val Arg Thr
            20                  25                  30

Tyr

<210> SEQ ID NO 12
<211> LENGTH: 33
<212> TYPE: PRT
<213> ORGANISM: Artificial sequence
<220> FEATURE:
<223> OTHER INFORMATION: mitochondrial targeting peptide

<400> SEQUENCE: 12

Met Phe Ser Arg Leu Pro Thr Ser Leu Ala Arg Asn Val Ala Arg Arg
1               5                   10                  15

Ala Pro Thr Ser Phe Val Arg Pro Ser Ala Ala Ala Ala Ala Leu Arg
            20                  25                  30

Phe

<210> SEQ ID NO 13
<211> LENGTH: 71
<212> TYPE: PRT
<213> ORGANISM: Artificial sequence
<220> FEATURE:
<223> OTHER INFORMATION: mitochondrial targeting peptide

<400> SEQUENCE: 13

Met Asn Ser Leu Ile Phe Gly Lys Gln Leu Ala Phe His Lys Ile Val
1               5                   10                  15

Pro Thr Thr Ala Ile Gly Trp Leu Val Pro Leu Gly Asn Pro Ser Leu
            20                  25                  30

Gln Ile Pro Gly Gln Lys Gln Leu Gly Ser Ile His Arg Trp Leu Arg
        35                  40                  45

Glu Lys Leu Gln Gln Asp His Lys Asp Thr Glu Asp Lys Asp Phe Phe
    50                  55                  60

Ser Asn Asn Gly Ile Leu Leu
65                  70

<210> SEQ ID NO 14
<211> LENGTH: 31
<212> TYPE: PRT
<213> ORGANISM: Artificial sequence
<220> FEATURE:
<223> OTHER INFORMATION: mitochondrial targeting peptide

<400> SEQUENCE: 14

Met Leu Gln Leu Arg Phe Met Pro Gly Trp Val Pro Arg Asn Gly Phe
1               5                   10                  15

Phe Gly Leu Lys Glu Thr Ile Gly Thr Val His Lys Arg Phe Tyr
            20                  25                  30

<210> SEQ ID NO 15
<211> LENGTH: 17
<212> TYPE: PRT
<213> ORGANISM: Artificial sequence
<220> FEATURE:
<223> OTHER INFORMATION: mitochondrial targeting peptide
```

```
<400> SEQUENCE: 15

Met Phe Asn Arg Val Phe Thr Arg Ser Phe Ala Ser Ser Leu Arg Ala
1               5                   10                  15

Ala

<210> SEQ ID NO 16
<211> LENGTH: 33
<212> TYPE: PRT
<213> ORGANISM: Artificial sequence
<220> FEATURE:
<223> OTHER INFORMATION: mitochondrial targeting peptide

<400> SEQUENCE: 16

Met Ser Ile Val Gly Arg Asn Ala Ile Leu Asn Leu Arg Ile Ser Leu
1               5                   10                  15

Cys Pro Leu Phe Met Gly Lys Arg Ser Phe Val Ser Ser Pro Val Ser
            20                  25                  30

Asn

<210> SEQ ID NO 17
<211> LENGTH: 46
<212> TYPE: PRT
<213> ORGANISM: Artificial sequence
<220> FEATURE:
<223> OTHER INFORMATION: mitochondrial targeting peptide

<400> SEQUENCE: 17

Met Phe Leu Arg Ser Val Asn Arg Ala Val Thr Arg Ser Ile Leu Thr
1               5                   10                  15

Thr Pro Lys Pro Ala Val Val Lys Ser Ser Trp Arg Val Phe Thr Val
            20                  25                  30

Ala Asn Ser Lys Arg Cys Phe Thr Pro Ala Ala Ile Met Arg
        35                  40                  45

<210> SEQ ID NO 18
<211> LENGTH: 36
<212> TYPE: PRT
<213> ORGANISM: Artificial sequence
<220> FEATURE:
<223> OTHER INFORMATION: mitochondrial targeting peptide

<400> SEQUENCE: 18

Met Phe Arg Ser Val Cys Arg Ile Ser Ser Arg Val Ala Pro Ser Ala
1               5                   10                  15

Tyr Arg Thr Ile Met Gly Arg Ser Val Met Ser Asn Thr Ile Leu Ala
            20                  25                  30

Gln Arg Phe Tyr
        35

<210> SEQ ID NO 19
<211> LENGTH: 27
<212> TYPE: PRT
<213> ORGANISM: Artificial sequence
<220> FEATURE:
<223> OTHER INFORMATION: mitochondrial targeting peptide

<400> SEQUENCE: 19

Met Leu Cys Gln Gln Met Ile Arg Thr Thr Ala Lys Arg Ser Ser Asn
1               5                   10                  15

Ile Met Thr Arg Pro Ile Ile Met Lys Arg Ser
            20                  25
```

<210> SEQ ID NO 20
<211> LENGTH: 27
<212> TYPE: PRT
<213> ORGANISM: Artificial sequence
<220> FEATURE:
<223> OTHER INFORMATION: mitochondrial targeting peptide

<400> SEQUENCE: 20

```
Met Leu Arg Asn Thr Phe Thr Arg Ala Gly Gly Leu Ser Arg Ile Thr
1               5                   10                  15

Ser Val Arg Phe Ala Gln Thr His Ala Leu Ser
            20                  25
```

<210> SEQ ID NO 21
<211> LENGTH: 37
<212> TYPE: PRT
<213> ORGANISM: Artificial sequence
<220> FEATURE:
<223> OTHER INFORMATION: mitochondrial targeting peptide

<400> SEQUENCE: 21

```
Met Ser Ala Ile Leu Ser Thr Thr Ser Lys Ser Phe Leu Ser Arg Gly
1               5                   10                  15

Ser Thr Arg Gln Cys Gln Asn Met Gln Lys Ala Leu Phe Ala Leu Leu
            20                  25                  30

Asn Ala Arg His Tyr
        35
```

<210> SEQ ID NO 22
<211> LENGTH: 15
<212> TYPE: PRT
<213> ORGANISM: Artificial sequence
<220> FEATURE:
<223> OTHER INFORMATION: mitochondrial targeting peptide

<400> SEQUENCE: 22

```
Met Leu Arg Asn Thr Phe Phe Arg Asn Thr Ser Arg Arg Phe Leu
1               5                   10                  15
```

<210> SEQ ID NO 23
<211> LENGTH: 29
<212> TYPE: PRT
<213> ORGANISM: Artificial sequence
<220> FEATURE:
<223> OTHER INFORMATION: mitochondrial targeting peptide

<400> SEQUENCE: 23

```
Met Phe Leu Pro Lys Phe Asn Pro Ile Arg Ser Phe Ser Pro Ile Leu
1               5                   10                  15

Arg Ala Lys Thr Leu Leu Arg Tyr Gln Asn Arg Met Tyr
            20                  25
```

<210> SEQ ID NO 24
<211> LENGTH: 1149
<212> TYPE: DNA
<213> ORGANISM: Artificial sequence
<220> FEATURE:
<223> OTHER INFORMATION: recombinant polynucleotide

<400> SEQUENCE: 24

```
atggcctcca ctcgtgtcct cgcctctcgc ctggcctccc agatggctgc ttccgccaag      60
gttgcccgcc ctgctgtccg cgttgctcag gtcagcaagc gcaccatcca gactggctcc     120
```

-continued

```
cccctccaga ccctcaagcg cacccagatg acctccatcg tcaacgccac cacccgccag      180
gctttccaga agcgcgccta ctcttccagg ccttgggact actctgaaaa ggttaaggaa      240
catttctaca atccaaagaa cgccggtgct gtagaaggtg caaacgccat tggtgacgtt      300
ggttcattat cctgtggtga cgctttgaga ttaacattga agttgaccc tgaaaccgat       360
gtcatcttgg acgcaggttt tcaaactttc ggttgcggtt ctgctattgc atcttcatcc      420
gctttgactg aaatggttaa gggttttgaca ttggatgaag cattgaaaat ctcaaaccaa     480
gatatcgctg actatttgga tggtttgcca cctgaaaaga tgcattgttc cgtcatgggt      540
agagaagcct acaagctgc agtagctaac tacagaggtg aaaccattga agatgaccac      600
gaagaaggtg cattgatatg taaatgcttt gccgttgatg aagttatggt cagagatacc      660
ataagagcaa ataagttaag tactgtagaa gatgttacta actacacaaa agctggtggt     720
ggttgttctg cttgccatga agcaatagaa agagttttga cagaagaatt ggccgctaga     780
ggtgaagtat tcgttgcagc cccaattaaa gccaaaaaga aagtcaaggt attggctcca     840
gaacctgccc cagctcctgt tgcagaagcc ccagctgcag cccctaagtt gtcaaatttg      900
caaagaatta aagaatcga acagtcttg gctgcaataa gacctaccct gcaaagagac       960
aaaggtgacg tcgaattaat tgatgtagac ggtaaaaatg tttacgtcaa attgaccggt    1020
gcttgtactg gttgccaaat ggcatccatg acattaggtg gtatacaaca aagattgatc    1080
gaagaattgg gtgagttcgt caaagttatc ccagtctccg ctgccgcaca cgcccaaatg    1140
gaagtctga                                                            1149
```

<210> SEQ ID NO 25
<211> LENGTH: 382
<212> TYPE: PRT
<213> ORGANISM: Artificial sequence
<220> FEATURE:
<223> OTHER INFORMATION: recombinant protein

<400> SEQUENCE: 25

```
Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Tyr Ser Ser Arg Pro Trp Asp Tyr Ser Glu Lys Val Lys Glu
65                  70                  75                  80

His Phe Tyr Asn Pro Lys Asn Ala Gly Ala Val Glu Gly Ala Asn Ala
                85                  90                  95

Ile Gly Asp Val Gly Ser Leu Ser Cys Gly Asp Ala Leu Arg Leu Thr
            100                 105                 110

Leu Lys Val Asp Pro Glu Thr Asp Val Ile Leu Asp Ala Gly Phe Gln
        115                 120                 125

Thr Phe Gly Cys Gly Ser Ala Ile Ala Ser Ser Ala Leu Thr Glu
    130                 135                 140

Met Val Lys Gly Leu Thr Leu Asp Glu Ala Leu Lys Ile Ser Asn Gln
145                 150                 155                 160

Asp Ile Ala Asp Tyr Leu Asp Gly Leu Pro Pro Glu Lys Met His Cys
                165                 170                 175
```

```
Ser Val Met Gly Arg Glu Ala Leu Gln Ala Ala Val Ala Asn Tyr Arg
            180                 185                 190
Gly Glu Thr Ile Glu Asp Asp His Glu Glu Gly Ala Leu Ile Cys Lys
            195                 200                 205
Cys Phe Ala Val Asp Glu Val Met Val Arg Asp Thr Ile Arg Ala Asn
        210                 215                 220
Lys Leu Ser Thr Val Glu Asp Val Thr Asn Tyr Thr Lys Ala Gly Gly
225                 230                 235                 240
Gly Cys Ser Ala Cys His Glu Ala Ile Glu Arg Val Leu Thr Glu Glu
                245                 250                 255
Leu Ala Ala Arg Gly Glu Val Phe Val Ala Pro Ile Lys Ala Lys
            260                 265                 270
Lys Lys Val Lys Val Leu Ala Pro Glu Pro Ala Pro Val Ala
        275                 280                 285
Glu Ala Pro Ala Ala Pro Lys Leu Ser Asn Leu Gln Arg Ile Arg
            290                 295                 300
Arg Ile Glu Thr Val Leu Ala Ala Ile Arg Pro Thr Leu Gln Arg Asp
305                 310                 315                 320
Lys Gly Asp Val Glu Leu Ile Asp Val Asp Gly Lys Asn Val Tyr Val
                325                 330                 335
Lys Leu Thr Gly Ala Cys Thr Gly Cys Gln Met Ala Ser Met Thr Leu
            340                 345                 350
Gly Gly Ile Gln Gln Arg Leu Ile Glu Glu Leu Gly Glu Phe Val Lys
                355                 360                 365
Val Ile Pro Val Ser Ala Ala His Ala Gln Met Glu Val
            370                 375                 380

<210> SEQ ID NO 26
<211> LENGTH: 1218
<212> TYPE: DNA
<213> ORGANISM: Artificial sequence
<220> FEATURE:
<223> OTHER INFORMATION: recombinant polynucleotide

<400> SEQUENCE: 26
atggcctcca ctcgtgtcct cgcctctcgc ctggcctccc agatggctgc ttccgccaag      60
gttgcccgcc tgctgtccg cgttgctcag gtcagcaagc gcaccatcca gactggctcc     120
cccctccaga ccctcaagcg cacccagatg acctccatcg tcaacgccac cacccgccag     180
gctttccaga gcgcgcccta ctcttcctca gcatggagtc atcctcagtt tgagaaaggt     240
ggaggttcag gtggtggaag cggtggatct gcttggtcac atccacaatt tgaaaaactc     300
gaaggatcca tggaaaagat gtccaagttc tcccatttgt tgaaagctca tccatgcttc     360
aacgaaaagg ttcatgataa gtacggtaga gttcatttgc cagttgctcc aagatgtaac     420
attgcttgta agttctgcaa gaggtccgtt tctaaagaat gttgtgaaca tagaccaggt     480
gtttctttgg gtgttttgaa accagaagat gttgaggact acctgaaaaa gatcttgaaa     540
gagatgccaa acatcaaggt tgttggtatt gctggtcctg tgattctct gtttaacaaa     600 gaaactttcg aaaccctgaa gatcatcgac gaaaagtttc ccaacttgat taagtgcatt     660
tccaccaacg tctgttgtt gtctaagtac tacaaggatt tggccaactt gaacgttaga     720
actattaccg ttactgtcaa cgccattaag ccagaaatct tggaaaaaat cgttgactgg     780
gtttactacg acaagaagtt gtatagaggt ttggaaggtg ccaagttgtt gatcgaaaaa     840
caaatcgaag gtatcaagaa ggcctccgaa gaagatttca ttatcaagat caacaccgtc     900
```

-continued

```
ttgatcccag aaatcaacat ggatcacgtt gttgaaattg ccaagttctt caaggattac     960
gcctacgttc aaaacatcat tccattgatt ccacagtaca agatgaagga attgagagca    1020
ccaacttgcg aagaaatcaa aaaggtcaga aagagtgcg agaagtacat cccacaattc     1080
agagcttgtg gtcaatgtag agctgatgct gttggtctga tcaaagaaaa agagctgttg    1140
aaagagtttt tcaaagagaa gaacaaagaa agaacatca agctggaagt gttcgacttg     1200
aagcacttct ctcattga                                                   1218
```

<210> SEQ ID NO 27
<211> LENGTH: 405
<212> TYPE: PRT
<213> ORGANISM: Artificial sequence
<220> FEATURE:
<223> OTHER INFORMATION: recombinant protein

<400> SEQUENCE: 27

```
Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
                20                  25                  30

Lys Arg Thr Ile Gln Thr Gly Ser Pro Leu Gln Thr Leu Lys Arg Thr
            35                  40                  45

Gln Met Thr Ser Ile Val Asn Ala Thr Thr Arg Gln Ala Phe Gln Lys
        50                  55                  60

Arg Ala Tyr Ser Ser Ser Ala Trp Ser His Pro Gln Phe Glu Lys Gly
65                  70                  75                  80

Gly Gly Ser Gly Gly Ser Gly Gly Ser Ala Trp Ser His Pro Gln
                85                  90                  95

Phe Glu Lys Leu Glu Gly Ser Met Glu Lys Met Ser Lys Phe Ser His
            100                 105                 110

Leu Leu Lys Ala His Pro Cys Phe Asn Glu Lys Val His Asp Lys Tyr
        115                 120                 125

Gly Arg Val His Leu Pro Val Ala Pro Arg Cys Asn Ile Ala Cys Lys
    130                 135                 140

Phe Cys Lys Arg Ser Val Ser Lys Glu Cys Cys Glu His Arg Pro Gly
145                 150                 155                 160

Val Ser Leu Gly Val Leu Lys Pro Glu Asp Val Glu Asp Tyr Leu Lys
                165                 170                 175

Lys Ile Leu Lys Glu Met Pro Asn Ile Lys Val Val Gly Ile Ala Gly
            180                 185                 190

Pro Gly Asp Ser Leu Phe Asn Lys Glu Thr Phe Glu Thr Leu Lys Ile
        195                 200                 205

Ile Asp Glu Lys Phe Pro Asn Leu Ile Lys Cys Ile Ser Thr Asn Gly
    210                 215                 220

Leu Leu Leu Ser Lys Tyr Tyr Lys Asp Leu Ala Asn Leu Asn Val Arg
225                 230                 235                 240

Thr Ile Thr Val Thr Val Asn Ala Ile Lys Pro Glu Ile Leu Glu Lys
                245                 250                 255

Ile Val Asp Trp Val Tyr Tyr Asp Lys Lys Leu Tyr Arg Gly Leu Glu
            260                 265                 270

Gly Ala Lys Leu Leu Ile Glu Lys Gln Ile Glu Gly Ile Lys Lys Ala
        275                 280                 285

Ser Glu Glu Asp Phe Ile Ile Lys Ile Asn Thr Val Leu Ile Pro Glu
    290                 295                 300
```

Ile Asn Met Asp His Val Val Glu Ile Ala Lys Phe Phe Lys Asp Tyr
305                 310                 315                 320

Ala Tyr Val Gln Asn Ile Ile Pro Leu Ile Pro Gln Tyr Lys Met Lys
                325                 330                 335

Glu Leu Arg Ala Pro Thr Cys Glu Ile Lys Lys Val Arg Lys Glu
            340                 345                 350

Cys Glu Lys Tyr Ile Pro Gln Phe Arg Ala Cys Gly Gln Cys Arg Ala
                355                 360                 365

Asp Ala Val Gly Leu Ile Lys Glu Lys Glu Leu Lys Glu Phe Phe
            370                 375                 380

Lys Glu Lys Asn Lys Glu Lys Asn Ile Lys Leu Glu Val Phe Asp Leu
385                 390                 395                 400

Lys His Phe Ser His
            405

<210> SEQ ID NO 28
<211> LENGTH: 1422
<212> TYPE: DNA
<213> ORGANISM: Artificial sequence
<220> FEATURE:
<223> OTHER INFORMATION: recombinant polynucleotide

<400> SEQUENCE: 28

```
atggcctcca ctcgtgtcct cgcctctcgc ctggcctccc agatggctgc ttccgccaag      60
gttgcccgcc ctgctgtccg cgttgctcag gtcagcaagc gcaccatcca gactggctcc     120
cccctccaga ccctcaagcg cacccagatg acctccatcg tcaacgccac cacccgccag     180
gctttccaga agcgcgccta ctcttccgca gccatggccg acgtttactt ggataataac     240
gctactacaa gagtcgatga cgaaaatagta caagctatgt tgccattttt cacagaacaa     300
ttcggtaacc cttccagttt gcattccttc ggtaaccaag ttggtatggc cttgaagaaa     360
gctagacaat ctgtccaaaa attgttaggt gcagaacacg attccgaaat cgttttttacc     420 agttgtggta ctgaatctga ctcaaccgcc attttgtctg ccttaaaagc tcaaccagaa     480
agaaagactg tcataaccac tgttgtcgaa catcctgcag tattgtcttt atgcgattat     540
ttggcctcag aaggttacac tgttcataag ttaccagtcg ataaaaaggg tagattggac     600
ttagaacact atgcttcctt gttaacagat gacgtagctg tagttagtgt tatgtgggca     660
aataacgaaa ctggtacatt gttttccaatt gaagaaatgg caagattagc cgatgacgct     720
ggtataatgt tccatactga tgcagtacaa gccgttggta agtccctat agacttgaag     780 aactcgtcaa tccacatgtt gtccttaagt ggtcataaat tgcacgctcc aaagggtgtt     840
ggtgtcttgt acttaagaag aggtacaaga ttcagacctt tgttaagagg tggtcatcaa     900
gaaagaggta gaagagccgg tactgaaaat gctgcatcta ttataggttt gggtgttgcc     960
gctgaaagag cttacaattt catggaacat gaaaacactg aagttaagag attgcgtgat    1020 agttagaag caggtatttt ggccgtcgta ccacacgcat tgttactgg tgacccagac    1080 aatagattac ctaacacagc taacatcgca ttcgaataca tcgaaggtga agctatcttg    1140
ttgttgttga acaaagttgg tatagcagcc tccagtggtt ctgcttgtac atctggttca    1200
ttggaaccat cacatgttat gagagcaatg gatattcctt atacagctgc acacggtact    1260
gttagatttt ctttgagtag atacacaacc gaagaagaaa ttgatagagt cattagagaa    1320
gtaccaccta ttgttgctca attgagaaaa ttgtctcctt actggtcagg taatggtcct    1380
gttgaagacc ctggtaaagc ctttgctcct gtctatggtt ga                       1422
```

<210> SEQ ID NO 29
<211> LENGTH: 473
<212> TYPE: PRT
<213> ORGANISM: Artificial sequence
<220> FEATURE:
<223> OTHER INFORMATION: recombinant protein

<400> SEQUENCE: 29

```
Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Tyr Ser Ser Ala Ala Met Ala Asp Val Tyr Leu Asp Asn Asn
65                  70                  75                  80

Ala Thr Thr Arg Val Asp Asp Glu Ile Val Gln Ala Met Leu Pro Phe
                85                  90                  95

Phe Thr Glu Gln Phe Gly Asn Pro Ser Ser Leu His Ser Phe Gly Asn
            100                 105                 110

Gln Val Gly Met Ala Leu Lys Lys Ala Arg Gln Ser Val Gln Lys Leu
        115                 120                 125

Leu Gly Ala Glu His Asp Ser Glu Ile Val Phe Thr Ser Cys Gly Thr
    130                 135                 140

Glu Ser Asp Ser Thr Ala Ile Leu Ser Ala Leu Lys Ala Gln Pro Glu
145                 150                 155                 160

Arg Lys Thr Val Ile Thr Thr Val Val Glu His Pro Ala Val Leu Ser
                165                 170                 175

Leu Cys Asp Tyr Leu Ala Ser Glu Gly Tyr Thr Val His Lys Leu Pro
            180                 185                 190

Val Asp Lys Lys Gly Arg Leu Asp Leu Glu His Tyr Ala Ser Leu Leu
        195                 200                 205

Thr Asp Asp Val Ala Val Val Ser Val Met Trp Ala Asn Asn Glu Thr
    210                 215                 220

Gly Thr Leu Phe Pro Ile Glu Glu Met Ala Arg Leu Ala Asp Asp Ala
225                 230                 235                 240

Gly Ile Met Phe His Thr Asp Ala Val Gln Ala Val Gly Lys Val Pro
                245                 250                 255

Ile Asp Leu Lys Asn Ser Ser Ile His Met Leu Ser Leu Ser Gly His
            260                 265                 270

Lys Leu His Ala Pro Lys Gly Val Gly Val Leu Tyr Leu Arg Arg Gly
        275                 280                 285

Thr Arg Phe Arg Pro Leu Leu Arg Gly Gly His Gln Glu Arg Gly Arg
    290                 295                 300

Arg Ala Gly Thr Glu Asn Ala Ala Ser Ile Ile Gly Leu Gly Val Ala
305                 310                 315                 320

Ala Glu Arg Ala Leu Gln Phe Met Glu His Glu Asn Thr Glu Val Lys
                325                 330                 335

Arg Leu Arg Asp Lys Leu Glu Ala Gly Ile Leu Ala Val Val Pro His
            340                 345                 350

Ala Phe Val Thr Gly Asp Pro Asp Asn Arg Leu Pro Asn Thr Ala Asn
        355                 360                 365
```

```
Ile Ala Phe Glu Tyr Ile Glu Gly Glu Ala Ile Leu Leu Leu Asn
            370                 375                 380

Lys Val Gly Ile Ala Ala Ser Ser Gly Ser Ala Cys Thr Ser Gly Ser
385                 390                 395                 400

Leu Glu Pro Ser His Val Met Arg Ala Met Asp Ile Pro Tyr Thr Ala
                405                 410                 415

Ala His Gly Thr Val Arg Phe Ser Leu Ser Arg Tyr Thr Thr Glu Glu
                420                 425                 430

Glu Ile Asp Arg Val Ile Arg Glu Val Pro Pro Ile Val Ala Gln Leu
                435                 440                 445

Arg Lys Leu Ser Pro Tyr Trp Ser Gly Asn Gly Pro Val Glu Asp Pro
450                 455                 460

Gly Lys Ala Phe Ala Pro Val Tyr Gly
465                 470

<210> SEQ ID NO 30
<211> LENGTH: 486
<212> TYPE: DNA
<213> ORGANISM: Artificial sequence
<220> FEATURE:
<223> OTHER INFORMATION: recombinant polynucleotide

<400> SEQUENCE: 30
atggcctcca ctcgtgtcct cgcctctcgc ctggcctccc agatggctgc ttccgccaag      60
gttgcccgcc ctgctgtccg cgttgctcag gtcagcaagc gcaccatcca gactggctcc     120
cccctccaga ccctcaagcg cacccagatg acctccatcg tcaacgccac cacccgccag     180
gctttccaga gcgcgcccta ctcttccatg gctcttaaga tagttgagtc ttgtgtgaac     240
tgctgggcat gtgttgatgt gtgcccaagt gaggctatat ccttggcagg tcctcatttt     300
gaaatttctg cttcaaaatg caccgagtgt gatggagact atgctgaaaa gcaatgcgca     360
tctatttgtc cagttgaagg tgctatcttg ttagcagacg gaactcctgc taacccacct     420
ggttcactta caggaatccc acctgaaaga ttggctgagg caatgagaga aatacaggca     480
aggtaa                                                                486

<210> SEQ ID NO 31
<211> LENGTH: 161
<212> TYPE: PRT
<213> ORGANISM: Artificial sequence
<220> FEATURE:
<223> OTHER INFORMATION: recombinant protein

<400> SEQUENCE: 31

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
                20                  25                  30

Lys Arg Thr Ile Gln Thr Gly Ser Pro Leu Gln Thr Leu Lys Arg Thr
            35                  40                  45

Gln Met Thr Ser Ile Val Asn Ala Thr Thr Arg Gln Ala Phe Gln Lys
50                  55                  60

Arg Ala Tyr Ser Ser Met Ala Leu Lys Ile Val Glu Ser Cys Val Asn
65                  70                  75                  80

Cys Trp Ala Cys Val Asp Val Cys Pro Ser Glu Ala Ile Ser Leu Ala
                85                  90                  95

Gly Pro His Phe Glu Ile Ser Ala Ser Lys Cys Thr Glu Cys Asp Gly
                100                 105                 110
```

```
Asp Tyr Ala Glu Lys Gln Cys Ala Ser Ile Cys Pro Val Glu Gly Ala
            115                 120                 125

Ile Leu Leu Ala Asp Gly Thr Pro Ala Asn Pro Pro Gly Ser Leu Thr
    130                 135                 140

Gly Ile Pro Pro Glu Arg Leu Ala Glu Ala Met Arg Glu Ile Gln Ala
145                 150                 155                 160

Arg

<210> SEQ ID NO 32
<211> LENGTH: 513
<212> TYPE: DNA
<213> ORGANISM: Artificial sequence
<220> FEATURE:
<223> OTHER INFORMATION: recombinant polynucleotide

<400> SEQUENCE: 32
atggcctcca ctcgtgtcct cgcctctcgc ctggcctccc agatggctgc ttccgccaag      60
gttgcccgcc ctgctgtccg cgttgctcag gtcagcaagc gcaccatcca gactggctcc     120
cccctccaga ccctcaagcg cacccagatg acctccatcg tcaacgccac cacccgccag     180
gctttccaga agcgcgccta ctcttccatg gctcttaaga tagttgagtc ttgtgtgaac     240
tgctgggcat gtgttgatgt gtgcccaagt gaggctatat ccttggcagg tcctcatttt     300
gaaatttctg cttcaaaatg caccgagtgt gatggagact atgctgaaaa gcaatgcgca     360
tctatttgtc cagttgaagg tgctatcttg ttagcagacg gaactcctgc taacccacct     420
ggttcactta caggaatccc acctgaaaga ttggctgagg caatgagaga aatacaggca     480
aggtatccat atgatgttcc agattatgct taa                                  513

<210> SEQ ID NO 33
<211> LENGTH: 170
<212> TYPE: PRT
<213> ORGANISM: Artificial sequence
<220> FEATURE:
<223> OTHER INFORMATION: recombinant protein

<400> SEQUENCE: 33

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Tyr Ser Ser Met Ala Leu Lys Ile Val Glu Ser Cys Val Asn
65                  70                  75                  80

Cys Trp Ala Cys Val Asp Val Cys Pro Ser Glu Ala Ile Ser Leu Ala
                85                  90                  95

Gly Pro His Phe Glu Ile Ser Ala Ser Lys Cys Thr Glu Cys Asp Gly
            100                 105                 110

Asp Tyr Ala Glu Lys Gln Cys Ala Ser Ile Cys Pro Val Glu Gly Ala
            115                 120                 125

Ile Leu Leu Ala Asp Gly Thr Pro Ala Asn Pro Pro Gly Ser Leu Thr
    130                 135                 140

Gly Ile Pro Pro Glu Arg Leu Ala Glu Ala Met Arg Glu Ile Gln Ala
145                 150                 155                 160
```

```
Arg Tyr Pro Tyr Asp Val Pro Asp Tyr Ala
            165                 170
```

<210> SEQ ID NO 34
<211> LENGTH: 11
<212> TYPE: PRT
<213> ORGANISM: Artificial sequence
<220> FEATURE:
<223> OTHER INFORMATION: ferredoxin conserved motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid

<400> SEQUENCE: 34

```
Cys Xaa Xaa Cys Xaa Xaa Cys Xaa Xaa Xaa Cys
1               5                   10
```

<210> SEQ ID NO 35
<211> LENGTH: 124
<212> TYPE: PRT
<213> ORGANISM: Artificial sequence
<220> FEATURE:
<223> OTHER INFORMATION: ferredoxin conserved motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(83)
<223> OTHER INFORMATION: Xaa can be any naturally occurring amino acid
<220> FEATURE:
<221> NAME/KEY: misc_feature
<222> LOCATION: (85)..(87)
<223> OTHER INFORMATION: Xaa can be any naturally occurring amino acid
<220> FEATURE:
<221> NAME/KEY: misc_feature
<222> LOCATION: (89)..(123)
<223> OTHER INFORMATION: Xaa can be any naturally occurring amino acid

<400> SEQUENCE: 35

```
Cys Xaa Xaa Cys Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Cys Xaa Xaa Xaa Cys Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Cys
        115                 120
```

<210> SEQ ID NO 36
<211> LENGTH: 21
<212> TYPE: DNA
<213> ORGANISM: Artificial sequence
<220> FEATURE:
<223> OTHER INFORMATION: primer

<400> SEQUENCE: 36
attttcggtt tgtattactt c                                    21

<210> SEQ ID NO 37
<211> LENGTH: 17
<212> TYPE: DNA
<213> ORGANISM: Artificial sequence
<220> FEATURE:
<223> OTHER INFORMATION: primer

<400> SEQUENCE: 37
catggaagag taggcgc                                         17

<210> SEQ ID NO 38
<211> LENGTH: 35
<212> TYPE: DNA
<213> ORGANISM: Artificial sequence
<220> FEATURE:
<223> OTHER INFORMATION: primer

<400> SEQUENCE: 38
gcgcctactc ttccatggaa ttgtctgttt tgggt                     35

<210> SEQ ID NO 39
<211> LENGTH: 40
<212> TYPE: DNA
<213> ORGANISM: Artificial sequence
<220> FEATURE:
<223> OTHER INFORMATION: primer

<400> SEQUENCE: 39
atgatggtgg tggtgatgat gatgagcctt agcttgcaac                40

<210> SEQ ID NO 40
<211> LENGTH: 40
<212> TYPE: DNA
<213> ORGANISM: Artificial sequence
<220> FEATURE:
<223> OTHER INFORMATION: primer

<400> SEQUENCE: 40
atcaccacca ccatcatcac cattaagtcg acatggaaca                40

<210> SEQ ID NO 41
<211> LENGTH: 20
<212> TYPE: DNA
<213> ORGANISM: Artificial sequence
<220> FEATURE:
<223> OTHER INFORMATION: primer

<400> SEQUENCE: 41
gtacacgcgt ctgtacagaa                                      20

<210> SEQ ID NO 42
<211> LENGTH: 35
<212> TYPE: DNA
<213> ORGANISM: Artificial sequence
<220> FEATURE:
<223> OTHER INFORMATION: primer

```
<400> SEQUENCE: 42
gcgcctactc ttccatggag aaaatgtcta aattt                              35

<210> SEQ ID NO 43
<211> LENGTH: 40
<212> TYPE: DNA
<213> ORGANISM: Artificial sequence
<220> FEATURE:
<223> OTHER INFORMATION: primer

<400> SEQUENCE: 43
atgatggtgg tggtgatgat gatggtgtga gaaatgcttc                         40

<210> SEQ ID NO 44
<211> LENGTH: 22
<212> TYPE: DNA
<213> ORGANISM: Artificial sequence
<220> FEATURE:
<223> OTHER INFORMATION: primer

<400> SEQUENCE: 44
ggtggtaatg ccatgtaata tg                                            22

<210> SEQ ID NO 45
<211> LENGTH: 40
<212> TYPE: DNA
<213> ORGANISM: Artificial sequence
<220> FEATURE:
<223> OTHER INFORMATION: primer

<400> SEQUENCE: 45
gcataatctg gaacatcata tggatacctt gcctgtattt                         40

<210> SEQ ID NO 46
<211> LENGTH: 40
<212> TYPE: DNA
<213> ORGANISM: Artificial sequence
<220> FEATURE:
<223> OTHER INFORMATION: primer

<400> SEQUENCE: 46
gatgttccag attatgctta agagctctta attaacaatt                         40

<210> SEQ ID NO 47
<211> LENGTH: 29
<212> TYPE: DNA
<213> ORGANISM: Artificial sequence
<220> FEATURE:
<223> OTHER INFORMATION: primer

<400> SEQUENCE: 47
aaagtttaaa ccgcatcagg aaattgtaa                                     29

<210> SEQ ID NO 48
<211> LENGTH: 27
<212> TYPE: DNA
<213> ORGANISM: Artificial sequence
<220> FEATURE:
<223> OTHER INFORMATION: primer

<400> SEQUENCE: 48
aaaaagatct atggcctcca ctcgtgt                                       27

<210> SEQ ID NO 49
```

```
<211> LENGTH: 40
<212> TYPE: DNA
<213> ORGANISM: Artificial sequence
<220> FEATURE:
<223> OTHER INFORMATION: primer

<400> SEQUENCE: 49
ttttccatgg atccttcgag tttttcaaat tgtggatgtg                           40

<210> SEQ ID NO 50
<211> LENGTH: 37
<212> TYPE: DNA
<213> ORGANISM: Artificial sequence
<220> FEATURE:
<223> OTHER INFORMATION: primer

<400> SEQUENCE: 50
ttgaaaaact cgaaggatcc atggaaaaga tgtccaa                              37

<210> SEQ ID NO 51
<211> LENGTH: 26
<212> TYPE: DNA
<213> ORGANISM: Artificial sequence
<220> FEATURE:
<223> OTHER INFORMATION: primer

<400> SEQUENCE: 51
tttttctcga ggtcacctca atgaga                                          26

<210> SEQ ID NO 52
<211> LENGTH: 33
<212> TYPE: DNA
<213> ORGANISM: Artificial sequence
<220> FEATURE:
<223> OTHER INFORMATION: primer

<400> SEQUENCE: 52
aaaaggatcc aatggcctcc actcgtgtcc tcg                                  33

<210> SEQ ID NO 53
<211> LENGTH: 31
<212> TYPE: DNA
<213> ORGANISM: Artificial sequence
<220> FEATURE:
<223> OTHER INFORMATION: primer

<400> SEQUENCE: 53
ttttcacgtg ttaatggtga tgatggtggt g                                    31

<210> SEQ ID NO 54
<211> LENGTH: 32
<212> TYPE: DNA
<213> ORGANISM: Artificial sequence
<220> FEATURE:
<223> OTHER INFORMATION: primer

<400> SEQUENCE: 54
aaaagctagc atggcctcca ctcgtgtcct cg                                   32

<210> SEQ ID NO 55
<211> LENGTH: 30
<212> TYPE: DNA
<213> ORGANISM: Artificial sequence
<220> FEATURE:
<223> OTHER INFORMATION: primer

<400> SEQUENCE: 55
```

```
ttttgctagc gccttagctt gcaacaaagc                                    30

<210> SEQ ID NO 56
<211> LENGTH: 34
<212> TYPE: DNA
<213> ORGANISM: Artificial sequence
<220> FEATURE:
<223> OTHER INFORMATION: primer

<400> SEQUENCE: 56
ttttgctagc gcgtgtgaga aatgcttcaa gtcg                               34

<210> SEQ ID NO 57
<211> LENGTH: 28
<212> TYPE: DNA
<213> ORGANISM: Artificial sequence
<220> FEATURE:
<223> OTHER INFORMATION: primer

<400> SEQUENCE: 57
aaaaaggatc catggtgagc aagggcga                                      28

<210> SEQ ID NO 58
<211> LENGTH: 34
<212> TYPE: DNA
<213> ORGANISM: Artificial sequence
<220> FEATURE:
<223> OTHER INFORMATION: primer

<400> SEQUENCE: 58
aaaaaggtca ccttacttgt acagctcgtc catg                               34
```

US 10,941,428 B2

REAGENTS AND METHODS FOR THE EXPRESSION OF AN ACTIVE NIFB PROTEIN AND USES THEREOF

PRIORITY AND CROSS-REFERENCE TO RELATED APPLICATIONS

This application claims the benefit of European Patent Application No. EP18382654.4 filed on Sep. 12, 2018, which is hereby incorporated by reference in its entirety.

SEQUENCE LISTING IN ELECTRONIC FORMAT

The present application is being filed along with an Electronic Sequence Listing as an ASCII text file via EFS-Web. The Electronic Sequence Listing is provided as a file entitled ABG013001AUSSEQLIST.txt, created on Oct. 11, 2018 and modified on Oct. 15, 2018, which is 36,542 bytes in size. The information in the Electronic Sequence Listing is incorporated herein by reference in its entirety.

FIELD OF THE INVENTION

The invention relates to the field of genetics and, more particularly, to methods for expressing the NifB protein in a eukaryotic cell and for in vitro synthesis of active nitrogenase complex.

BACKGROUND OF THE INVENTION

Nitrogen is essential in plant development and a limiting factor in plant growth. It represents about 2% of the total plant dry matter that enters the food chains. Nevertheless, plants cannot directly access nitrogen gas ($N_2$) which makes up 78% of the atmosphere. In order for nitrogen gas to be used for growth it must first be fixed (i.e. reduced by hydrogen to ammonia) and be available in the combined form of ammonium ($NH_4^+$) or nitrate ($NO_3^-$). Plants adsorb said combined forms of nitrogen through their roots.

It is known that nitrogen is the main limiting factor of agricultural plant cultivation since the supply of nitrogen by fertilization is albeit efficient but expensive and is accompanied by an extreme environmental pollution due to the inefficient use of nitrogen by plants. Moreover, manufacturing nitrogen fertilizers requires six times more energy than needed to produce either phosphor or potassium fertilizers. The worldwide spreading conception of cultivation and sustainable development gives preference to the production based on internal resources instead of using external ones.

The so-called aerobic nitrogen-fixing bacteria, the members of genera *Azomonas, Azotobacter, Beijerinckia* and *Derxia* belonging to the family of Azotobactereceae, are capable of an efficient nitrogen-fixation even at atmospheric oxygen levels by the action of an evolutionarily conserved enzyme complex called nitrogenase. This complex is composed of two enzymes: a dinitrogenase and a dinitrogenase reductase. Both protein components of nitrogenase are extremely sensitive to oxygen and the bacteria fixing nitrogen aerobically have evolved a variety of strategies to protect nitrogenase from oxygen poisoning.

The nitrogen-fixing bacteria are unable in the nature to be incorporated into the inner tissue spaces of plants and to spread in the intercellular spaces although it could be proven that, when settling down on the roots or on the outer surfaces of leaves, these species are capable to provide the nitrogen demand of some plants to a significant or whole extent.

Genetic transformation of plants with genes of interest is a common technique used in order to make plants resistant to pest and agents which causing harm to cultures, to producing certain nutrients or pharmaceutical agents such as vaccines and to improve the growth of these plants to assist in farmer efficiency. However, a genetically engineered plant capable of fixing nitrogen has not been produced yet. Two main barriers have impaired this approach: the known sensitivity of nitrogenase to oxygen, which is the byproduct of plant photosynthesis and the genetic and biochemical complexity of nitrogenase biosynthesis.

Thus, it would be advantageous provide a method which allow plants fix their own nitrogen avoiding interactions of plants with specific symbiotic or associative nitrogen fixing bacteria.

SUMMARY OF THE INVENTION

In a first aspect the invention relates to a first polynucleotide encoding a fusion protein comprising NifB protein and a mitochondrial targeting peptide.

In a second aspect the invention relates to a first expression vector comprising the first polynucleotide of the invention.

In a third aspect the invention relates to a eukaryotic cell comprising the first polynucleotide or the first expression vector of the invention.

In a fourth aspect the invention relates to a first method for expressing NifB protein in a eukaryotic cell comprising the steps of:
  i) introducing into said cell a polynucleotide according to the first aspect of the invention or a vector according to the second aspect of the invention.
  ii) growing said cell under conditions allowing the expression of said protein and, if desired,
  iii) purifying said protein under anaerobic conditions.

In a fifth aspect the invention relates to a NifB protein obtained by the first method of the invention.

In a sixth aspect the invention relates to a second polynucleotide encoding a fusion protein comprising any of NifU, NifS or FdxN proteins and a mitochondrial targeting peptide.

In a seventh aspect the invention relates to a second expression vector comprising the second polynucleotide of the invention.

In an eighth aspect the invention relates to a eukaryotic cell comprising the second polynucleotide or the second expression vector of the invention.

In a ninth aspect the invention relates to a second method for expressing NifU, NifS or FdxN proteins in a eukaryotic cell comprising the steps of:
  i) introducing into said cell the second polynucleotide or the second vector of the invention,
  ii) growing said cell under conditions allowing the expression of said protein and, if desired,
  iii) purifying said protein under anaerobic conditions.

In a tenth aspect the invention relates to a NifU, NifS or FdxN protein obtained by the second method of the invention.

In an eleventh aspect the invention relates to a third method for in vitro synthesis of FeMo-co using NifB comprising the steps of:
  i) mixing NifB, apo-NifEN, NifH proteins with SAM or SAM generating system, molybdate or molybdenum donating protein, R-homocitrate or R-homocitrate generating system, a reducing agent, an ATP regenerating system and Mg-ATP, and, if desired, any or all of these components NifX, $Fe^{2+}$, and $S^{2-}$,
  ii) incubating the mixture defined in (i) under conditions allowing the synthesis of FeMo-co.

In a twelfth aspect the invention relates to a fourth method for in vitro synthesis of FeMo-co comprising the steps of:
  i) Mixing NifB with a cell-free-extract from an *Azotobacter vinelandii* strain carrying a disrupted nifB gene, R-homocitrate or R-homocitrate generating system, molybdate or molybdenum donating protein, a reducing agent, an ATP regenerating system and ATP, and, if desired, NifH, SAM or SAM generating system, $Fe^{2+}$, and $S^{2-}$,
  ii) incubating the mixture defined in (i) under conditions allowing the synthesis of FeMo-co.

In a thirteenth aspect the invention relates to a fifth method for in vitro activation of apo-NifDK comprising the steps of:
  i) contacting the product obtained by any of the fourth or fifth methods of the invention with apo-NifDK and,
  ii) incubating the mixture defined in (i) under conditions allowing the activation of apo-NifDK.

In a fourteenth aspect the invention relates to a kit comprising:
  i) a polynucleotide according to the first aspect of the invention or an expression vector according to the second aspect of the invention,
  ii) polynucleotides according to the sixth aspect of the invention or vectors according to the seventh aspect of the invention encoding each of NifU, NifS or FdxN proteins.
  iii) reagents adequate for carrying out a method according to any of the fourth or fifth aspects of the invention.

from W303-1a *S. cerevisiae* cells (WT) or cells expressing SU9-NifB$_{Av}$-Nis10 (SB09Y) were prepared. Soluble protein extracts (S) from *N. benthamiana* leaf cells infiltrated with *A. tumefaciens* containing control vector (pGFPGUSPlus) or vector for expression of SU9-NifB$_{Av}$-His10 (pN2XJ13). Dotted line indicate different exposures of the right part of the membrane. (C) Migration of SU9-NifB$_{Mt}$-His10 when expressed in *S. cerevisiae* and *N. benthamiana*. Migration in SDS-PAGE was determined after Western blot analysis using NifB$_{Mt}$ specific antibodies. Total protein extracts (TE) from W303-1a *S. cerevisiae* cells (WT) or cells expressing SU9-NifB$_{Mt}$-His10 (SB10Y) were prepared. Soluble protein extracts (S) from *N. benthamiana* leaf cells infiltrated with *A. tumefaciens* containing control vector (pGFPGUSPlus) or vector for expression of SU9-NifB$_{Mt}$-His10 (pN2XJ14). As control of *N. benthamiana* leaf infiltration, GFP expressed from the pGFPGUSPlus vector backbone was detected (B,C).

Figure 8:
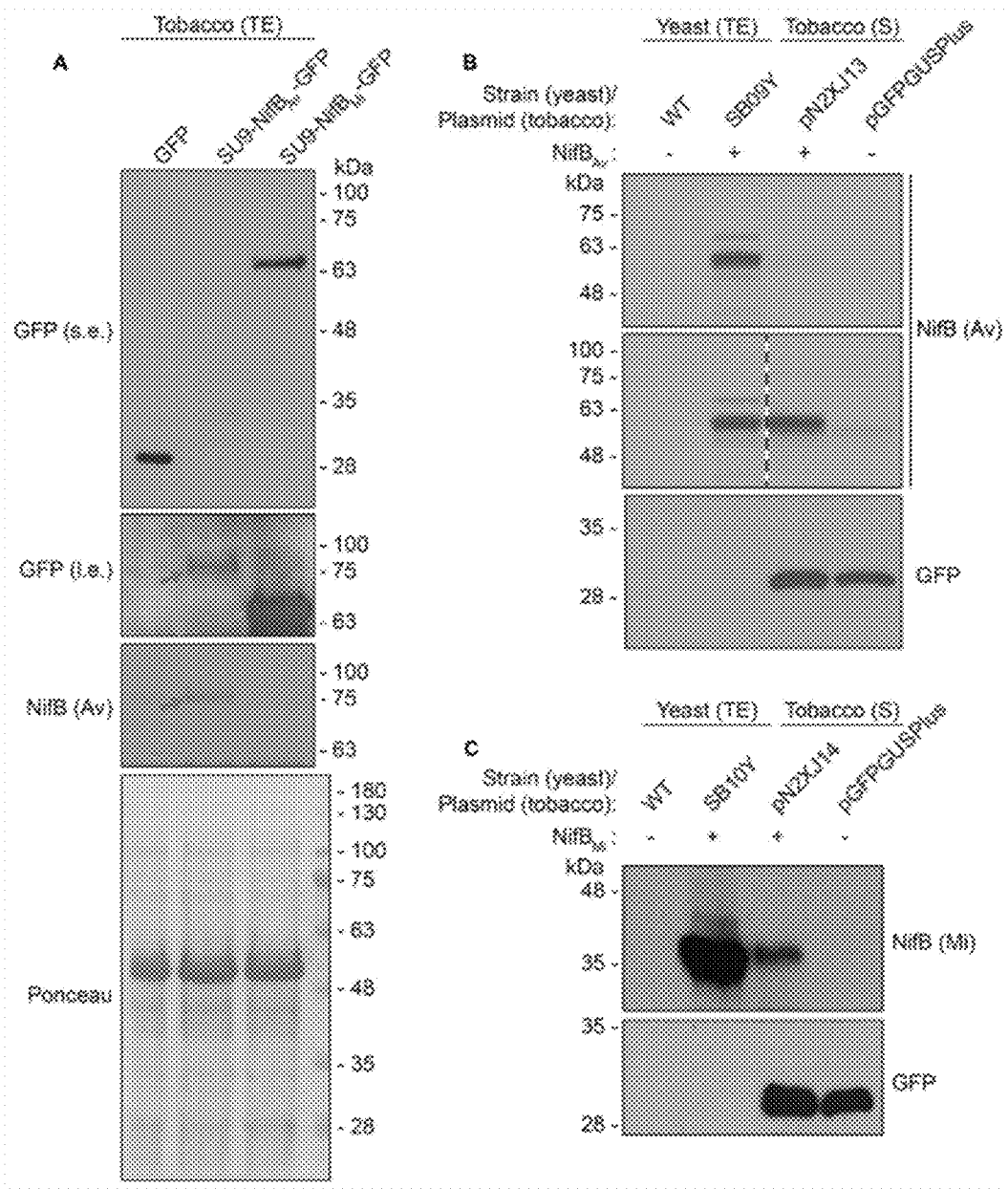
FIG. 8. Expression and solubility of mitochondria targeted (SU9) $NifB_{AV}$ and $NifB_{Mi}$ in *N. benthamiana* leaves. (A) Western blot analysis of total protein extracts (TE) prepared from infiltrated *N. benthamiana* leaves expressing GFP, SU9-$NifB_{Ai}$-GFP or SU9-$NifB_{Mi}$-GFP. Grey arrows indicate the polypeptide recognized both by GFP and NifBAv specific antibodies. Short (s.e.) and long (l.e.) film exposures of the GFP antibody probed membrane are shown. (B) Migration of SU9-NifBAv-His10 when expressed in *S. cerevisiae* and *N. benthamiana*. Migration in SDS-PAGE was determined after Western blot analysis using $NifB_{AV}$ specific antibodies. Total protein extracts (TE)
Figure 9:
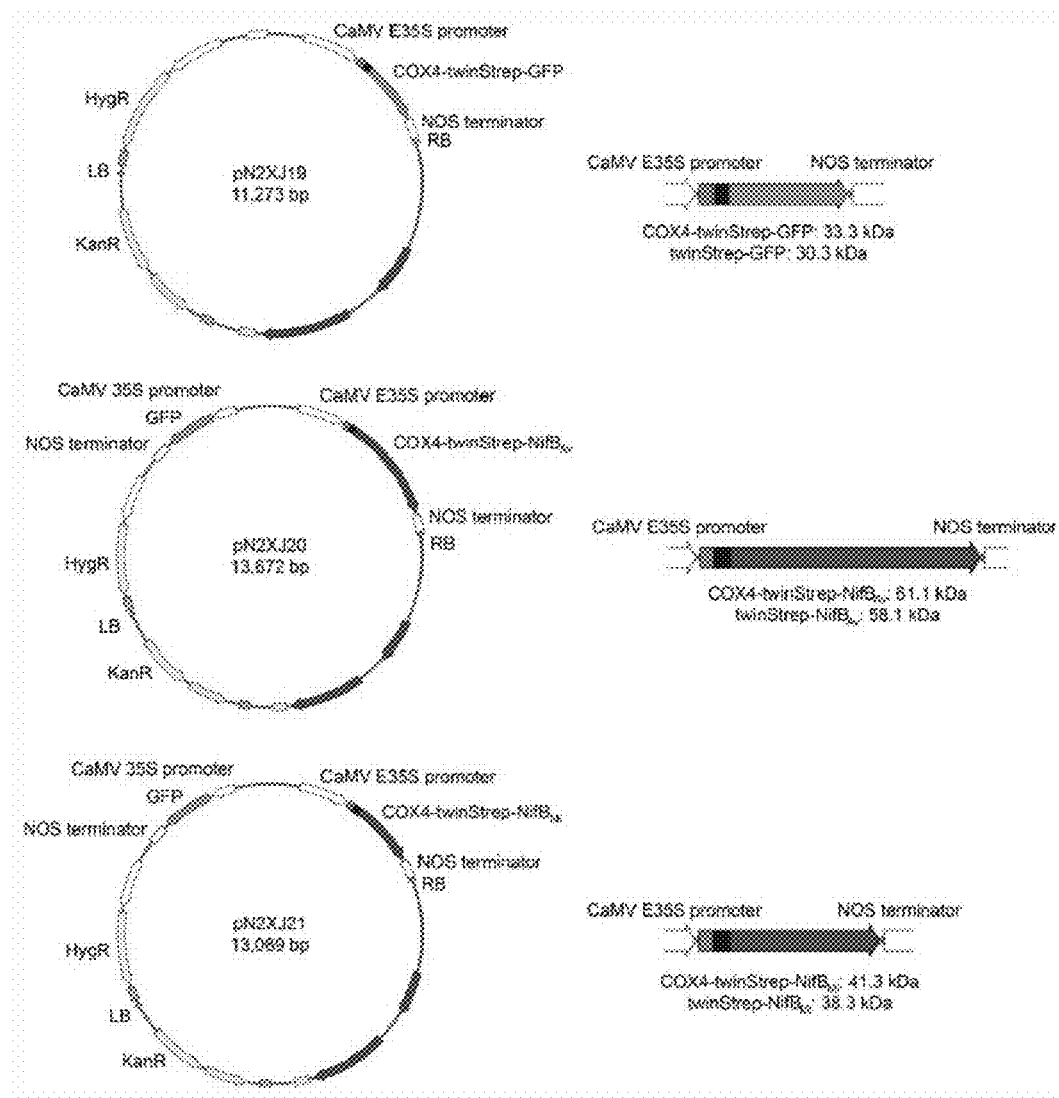

FIG. 9. Plant expression vectors with COX4 leader sequence. Schematic overview of plant expression vectors for expression of COX4-twinStrep-GFP, COX4-twinStrep-NifBAv and COX4-twinStrep-NifBMi. See Supplementary FIG. 8 for detailed information about DNA and protein sequences.

Figure 10:
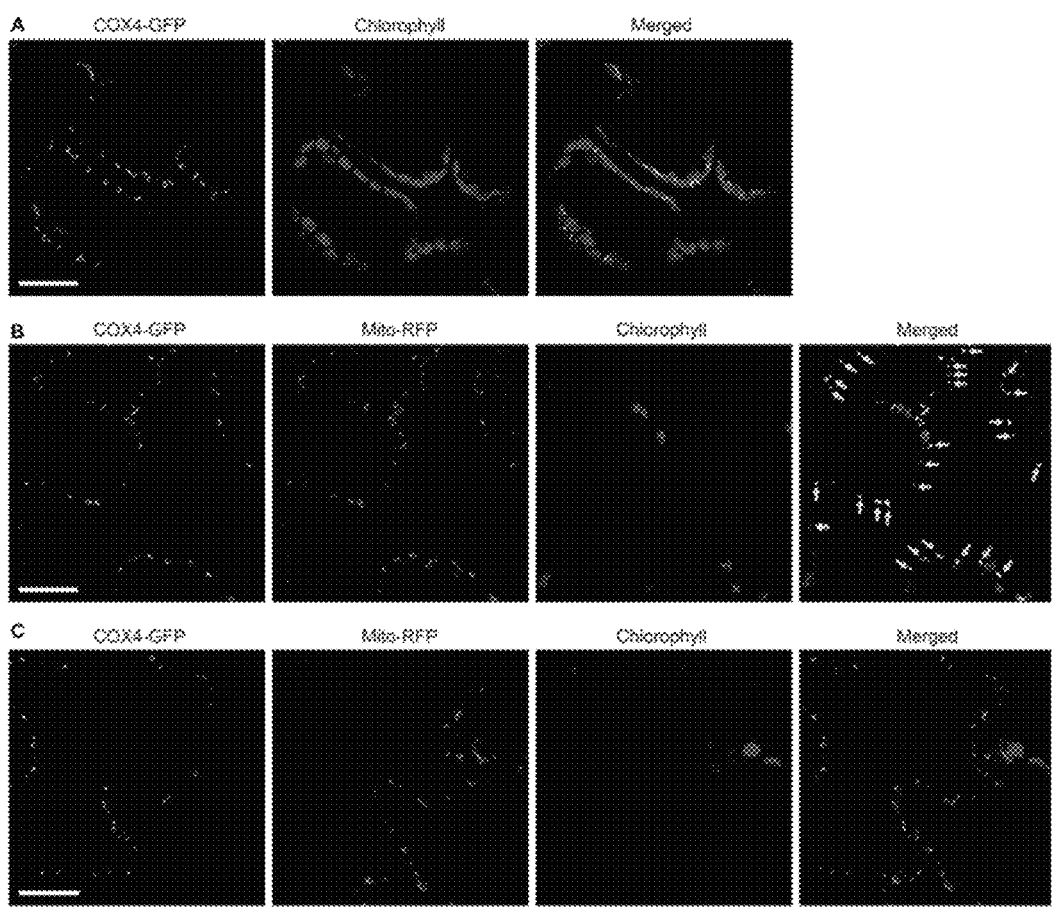

FIG. 10. Functionality of COX4 leader sequence for mitochondria targeting of GFP in *N. benthamiana* leaves. (A) Mesophyll cells expressing COX4-twinStrep-GFP. GFP (green) and chlorophyll autofluorescence (red) of chloroplasts is shown. (B,C) Epidermal cells expressing COX4-twinStrep-GFP together with a fluorescent mitochondria marker (Mito-RFP). GFP (green), Mito-RFP (magenta) and chlorophyll autofluorescence (red) of chloroplasts is shown. Co-localization of COX4-twinStrep-GFP with Mito-RFP labeled structures (B) is shown as white in the merged image, and highlighted with yellow arrows. Adjacent cells expressing COX4-twinStrep-GFP or Mito-RFP (C) are shown as control to verify the specificity of the signal recorded in each channel. Scale bars show 30 um.

Figure 11:
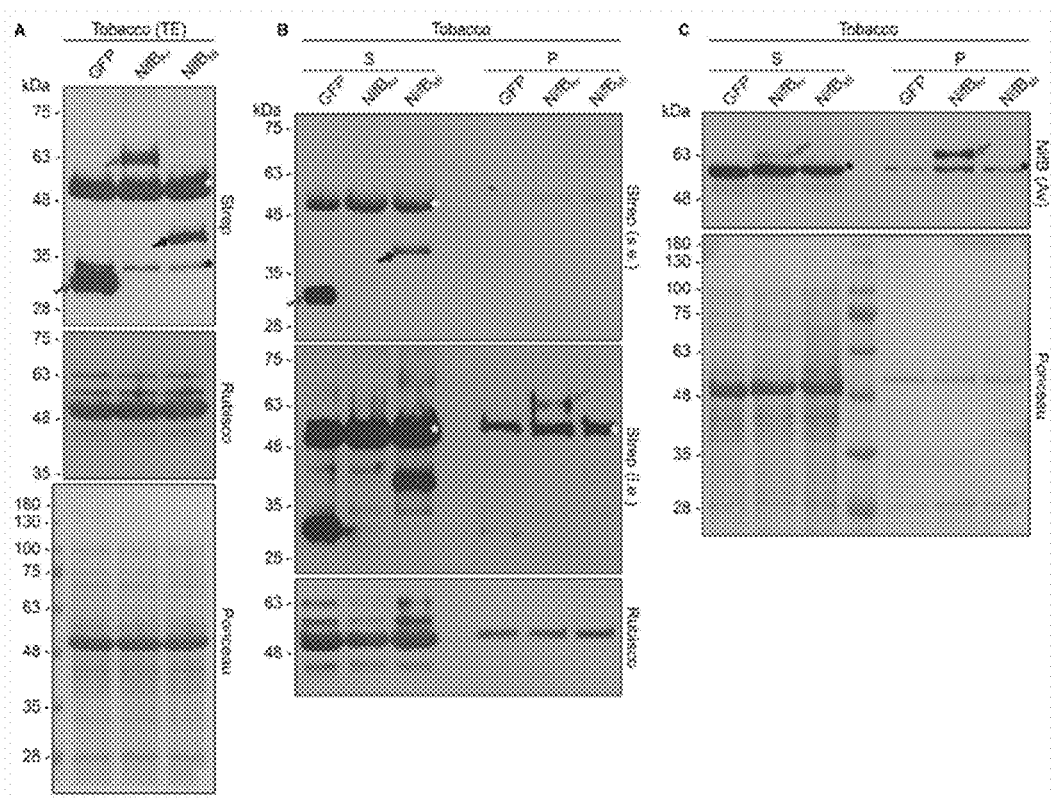

FIG. 11. Expression and solubility of mitochondria targeted (COX4) NifBAv and NifBMi in *N. benthamiana* leaves. (A) Western blot analysis of total protein extracts (TE) prepared from infiltrated *N. benthamiana* leaves expressing COX4-twinStrep-GFP (GFP), COX4-twinStrep-NifBAv (NifBAv) or COX4-twinStrep-NifBMi (NifBMi) and separated by SDS-PAGE. The COX4-twinStrep-GFP (green arrow), COX4-twinStrep-NifBAv (blue arrow), COX4-twinStrep-NifBMi (red arrow) proteins are highlighted. A pronounced non-specific polypeptide detected using the Strep-tag antibodies (white star) co-migrated with the large subunit of Rubisco. The membrane probed with antibodies against Rubisco was also stained with Ponceau and is included as loading control. (B,C) Western blot analysis of the soluble (S) and non-soluble pellet (P) fractions of *N. benthamiana* leaf total extracts used in (A), using Strep-tag antibodies (B) or NifB$_{Av}$ antibodies (C). The COX4-twinStrep-GFP (green arrow), COX4-twinStrep-NifB$_{Av}$ (blue arrow), COX4-twinStrep-NifB$_{Mi}$ (red arrow) proteins are highlighted. Non-specific bands detected using the Strep-tag antibodies (white stars) co-migrated with Rubisco (B). Non-specific bands detected with NifBAv antibodies (black stars) are also indicated (C). Short (s.e.) and long (l.e.) film exposures of the Strep-tag antibody probed membrane are shown (B). Ponceau staining of the NifBAv antibody probed membrane is shown as loading control (C).

Figure 12:
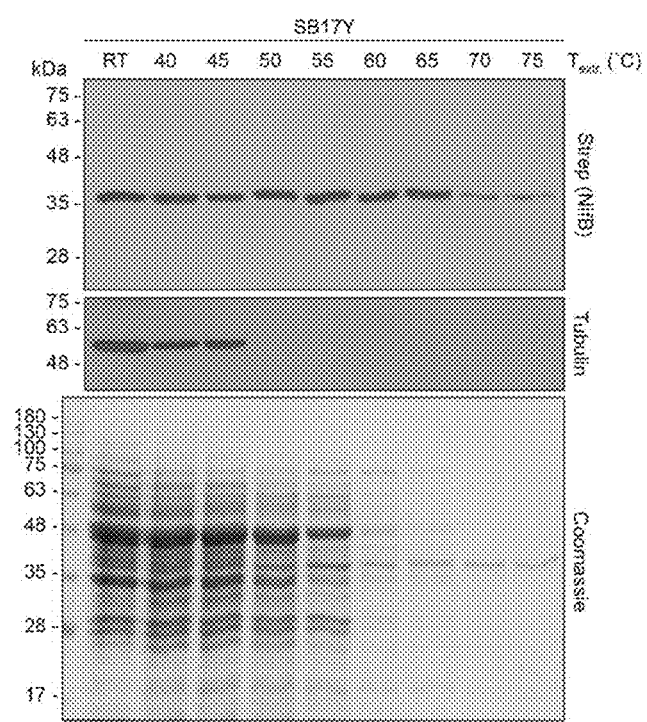

FIG. 12. Immunoblot analysis of soluble TS-NifB in SB17Y protein extracts upon heat-treatment at increasing temperatures. Heat-induced precipitation of yeast proteins in the extract at the different temperatures is shown using antibodies recognizing tubulin, as well as by Coomassie staining of proteins from the extract resolved by SDS-PAGE.

Figure 13:
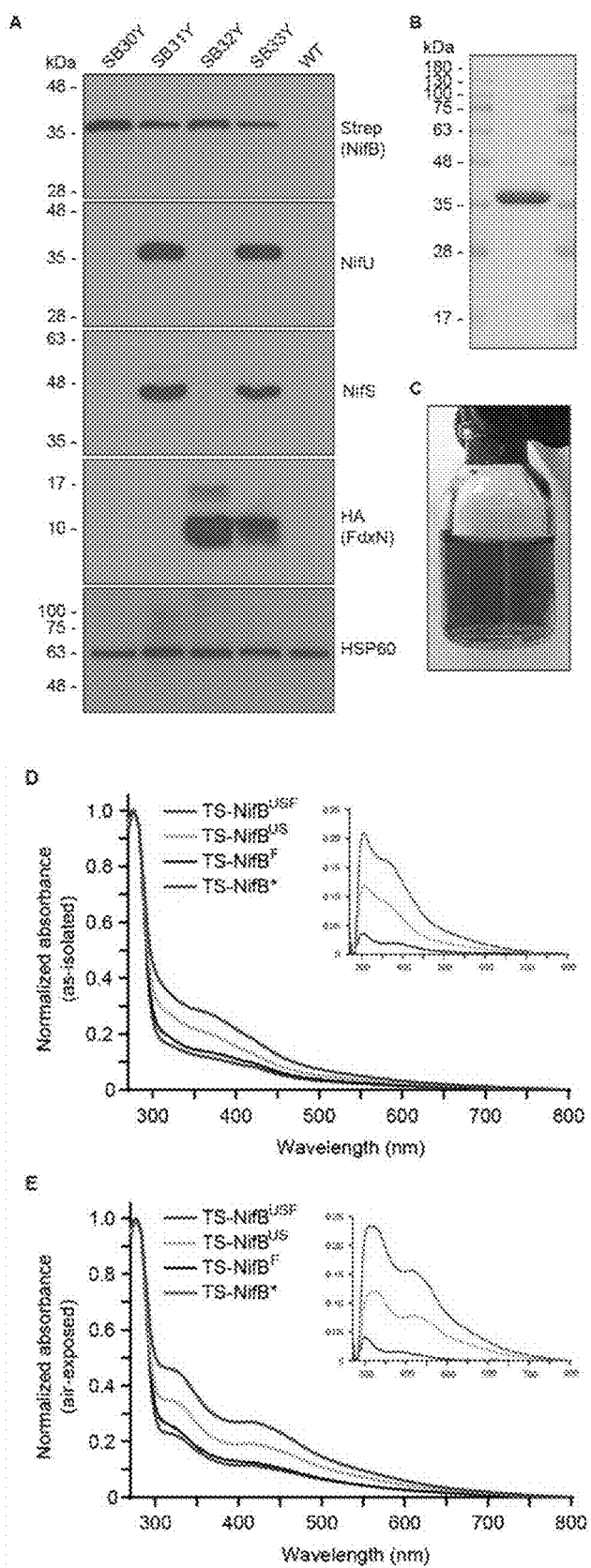

FIG. 13. Expression and purification of TS-NifB carrying [Fe—S] clusters from yeast (A). Immunoblot analysis of protein expression in total extracts of *S. cerevisiae* strains used for TS-NifB purifications. (B, C) Coomassie staining (B) and appearance (C) of TS-NifBUSF (purification 13, Table S2) obtained from 315 g yeast cells following elution and desalting (total volume about 13 ml). (D, E) As-isolated (D) and air-exposed (E) UV-visible spectra of TS-NifB$^{US}$ (purple), TS-Nif Bus (green), TS-NifB$^F$ (blue) and TS-NifB$^{USF}$ (red). Inserts show UV-visible spectra normalized to TS-NifB*.

Figure 14:
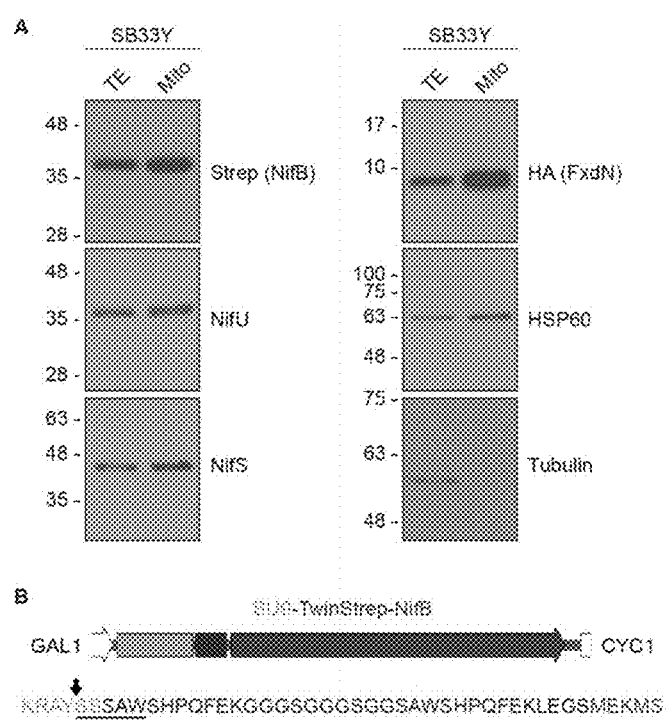

FIG. 14. (A) Immunoblot analysis of total extracts (TE) and mitochondria isolations (Mito) showing mitochondria targeting of TS-NifB, NifU, NifS and FdxN-HA in SB33Y. Antibodies recognizing cytoplasmic (tubulin) and mitochondria (HSP60) control proteins are included. (B) SU9 processing site (black arrow) of TS-NifB. Underlined sequence indicates the N-terminal amino acids identified by Edman degradation.

Figure 15:
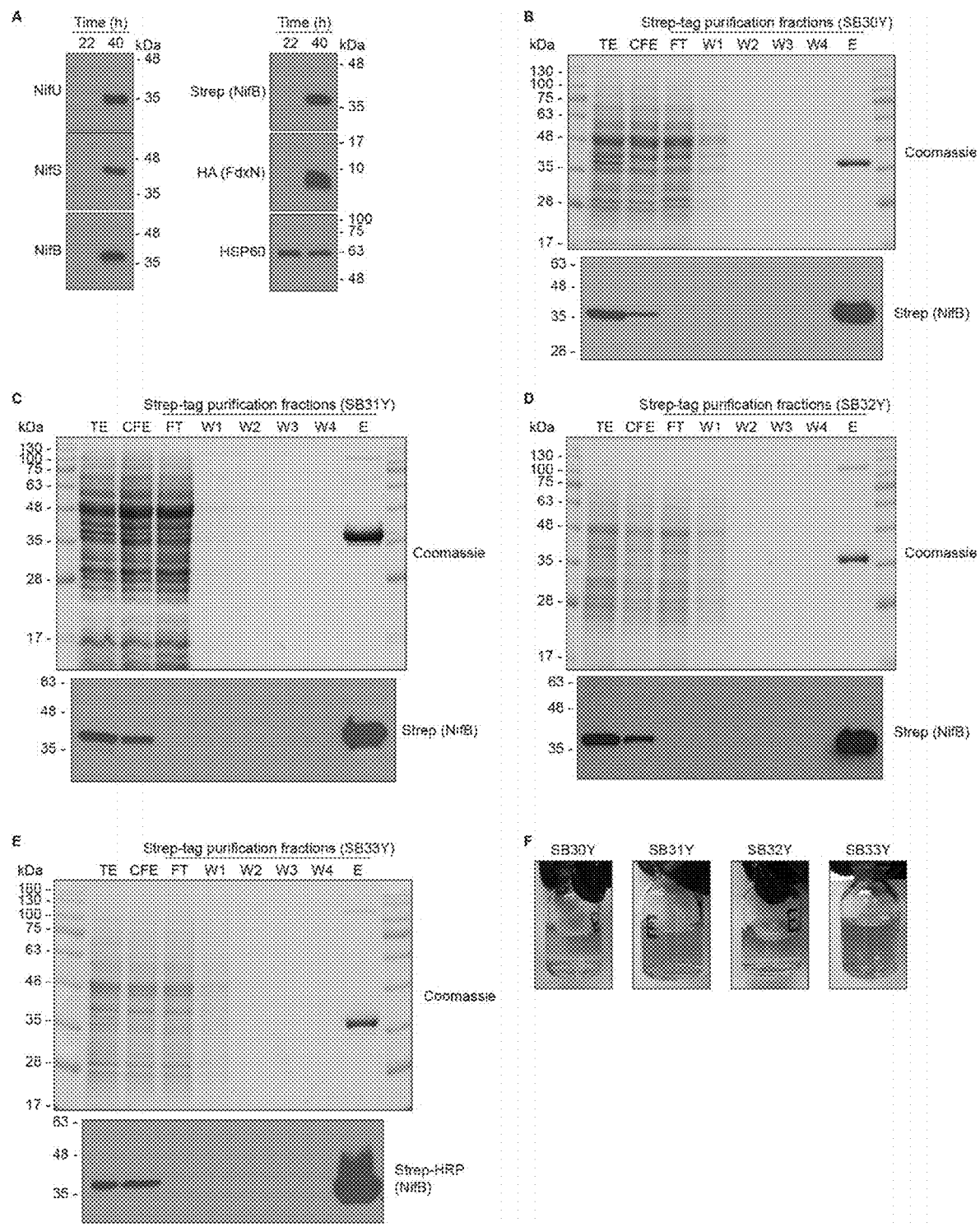

FIG. 15. (A) Example of protein expression in SB33Y before (22 h) and after (40 h) galactose induction. Galactose was added at t=22.5 h and fermenter harvested at t=40 h. (B-F) Coomassie staining and immunoblot analysis of representative TS-NifB purifications from SB30Y (B), SB31Y (C), SB32Y (D), SB33Y (E). TE, total extract; CFE, cell-free extract after removing debris; FT, flow through chromatographic resin; W1-W4, chromatographic wash fractions; E, protein eluted by applying biotin. Molecular mass markers are indicated to the left and primary antibody to the right of each panel. Typical appearance of the TS-NifB proteins purified from 100 g yeast cells following elution and desalting (total volume about 13 ml) (F).

Figure 16:
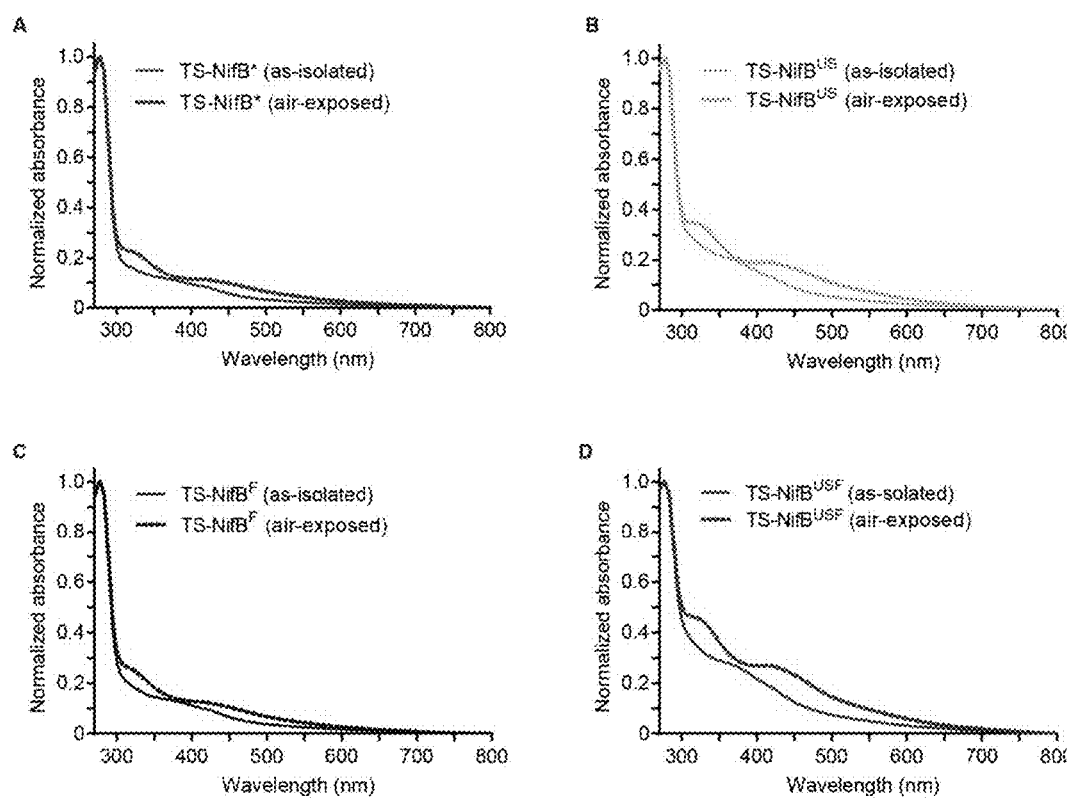

FIG. 16. (A-D) As-isolated and air-exposed UV-visible spectra of TS-NifB purified anaerobically from TS-NifB* (A), TS-NifB$^{US}$ (B), TS-NifB$^F$ (C) and TS-NifB$^{USF}$ (D)

Figure 17:
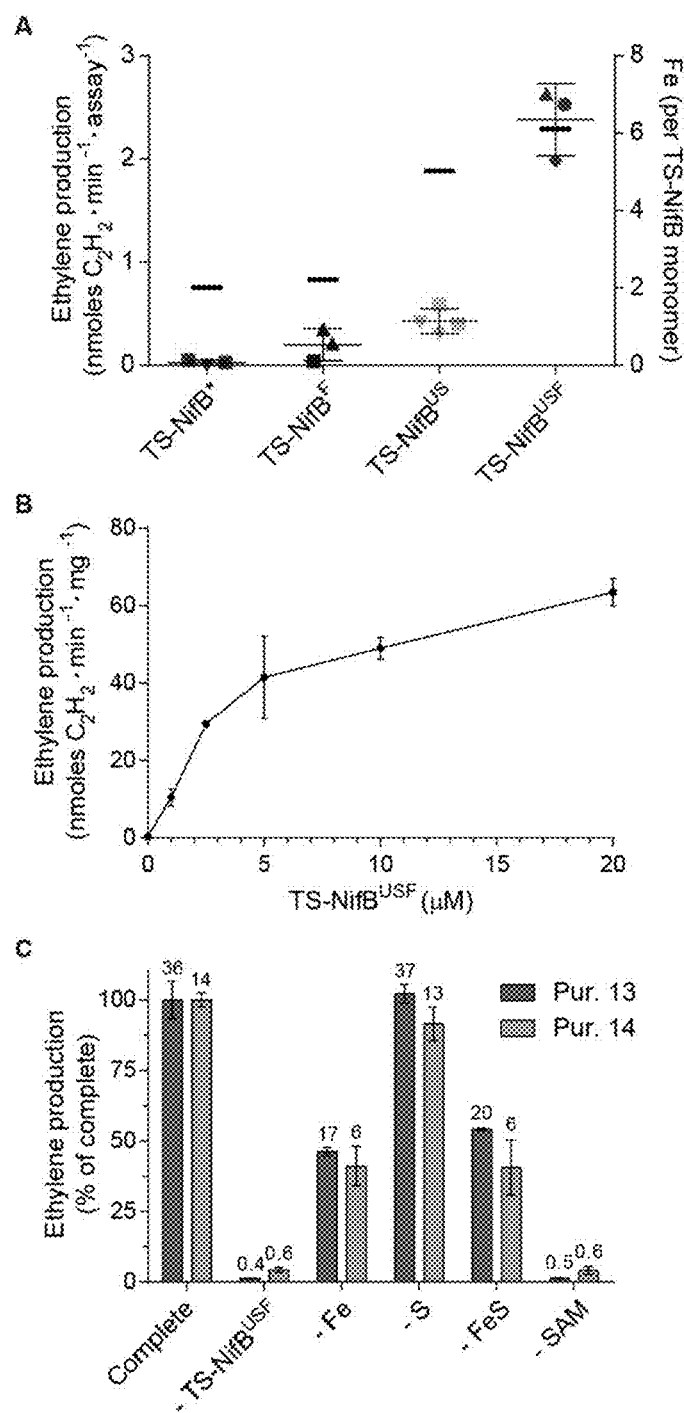

FIG. 17. Genetic and biochemical requirements for TS-NifB functionality. (A) In vitro synthesis of FeMo-co and apo-NifDK reconstitution assay using ΔnifB *A. vinelandii* (UW140) cell-free extracts and 12.5 µM of as-isolated TS-NifB* (purple), TS-NifB$^{US}$ (green), TS-NifB$^F$ (blue) or TS-NifB$^{USF}$ (red). Activity is represented as nmol ethylene produced per min and assay (left y-axis). Error bars represent mean±standard deviation (n=3, TS-NifB*, TS-NifB$^F$ and TS-NifB$^{USF}$; n=4, TS-NifB$^{US}$). Shape of symbols for each yeast strain indicate whether TS-NifB was purified from cells originating from same or different fermenters. Average Fe content of each TS-NifB is indicated with a dash (right y-axis, Table S2). (B) Titration of in vitro FeMo-co synthesis and apo-NifDK reconstitution using purified apo-NifEN, NifX, NifH, apo-NifDK, and as-isolated TS-NifB$^{USF}$ (purification 13, Table S2). Activity is represented as nmol ethylene produced per min and mg NifDK. Error bars represent mean±standard deviation (n=2). Specific activities of holo-NifDK and NifB-co-dependent activated apo-NifDK determined under the same reaction conditions were 1,331 and 260 nmol ethylene formed per min and mg NifDK protein, respectively. (C) Requirements for TS-NifB$^{USF}$ dependent in vitro FeMo-co synthesis and apo-NifDK reconstitution in a completely defined assay. Five µM TS-NifB$^{USF}$ were used per assay (purifications 13 and 14, Table S2). Activities are normalized to complete conditions (containing Mo$_4^{2-}$, R-homocitrate, Fe$^{2+}$, S$^{2-}$, SAM, DTH, apo-NifEN, apo-NifDK, NifX and NifH). Values above bars represent average nmol ethylene produced per min and mg apo-NifDK. Error bars represent mean±standard deviation (n=2). Specific activity of holo-NifDK and NifB-co-dependent activated apo-NifDK determined under the same reaction conditions was 1,137 and 202 nmol ethylene formed per min and mg NifDK protein, respectively.

Figure 18:
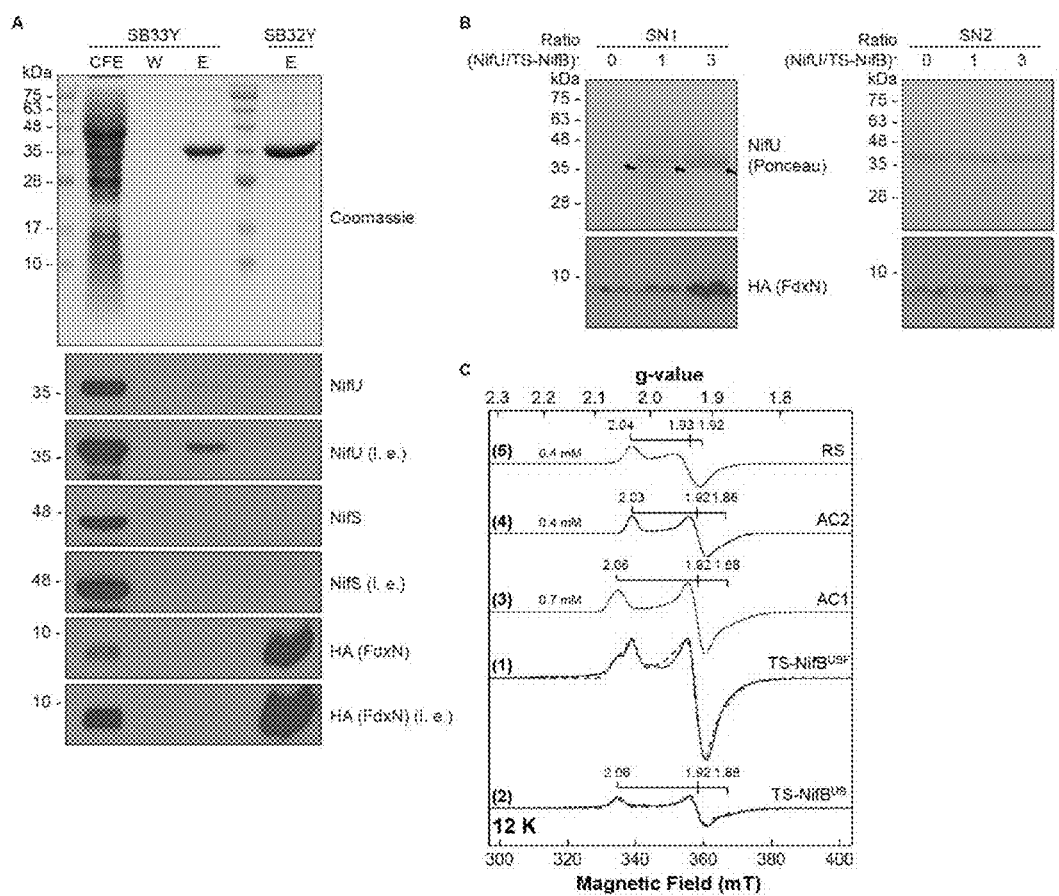

FIG. 18. FdxN is essential for incorporation of RS and AC2 [4Fe-4S] clusters into TS-NifB. (A) Coomassie staining and immunoblot analysis of proteins interacting with TS-NifBUSF and TS-NifBF. Long (l.e.) and short (s.e.) exposures are indicated. CFE, cell-free extract; W, wash fraction; E, biotin eluted fraction. (B) NifU-dependent release of TS-NifBF associated FdxN-HA. SN1 and SN2 represent protein present in the soluble fraction before (SN1) and after (SN2) addition of biotin to Strep-Tactin-immobilized TS-NifBF previously incubated with Nif U. Black arrows indicate a fraction TS-NifBF not bound to the Streptactin resin. (C) X-band EPR spectra of TS-NifBUSF (purification 14, Table S2) and TS-Nif BUS (purification 8+9, Table S2). EPR spectra of (1) TS-NifBUSF and (2) TS-NifBUS; (3)-(5) subcomponents of spectral simulation for TS-NifBUSF. Experimental data are shown in black solid lines while overall spectral simulations are shown in red dotted lines. The g values of each species, spin concentration of the subcomponents, and cluster nomenclature are indicated in the figure.

Figure 19:
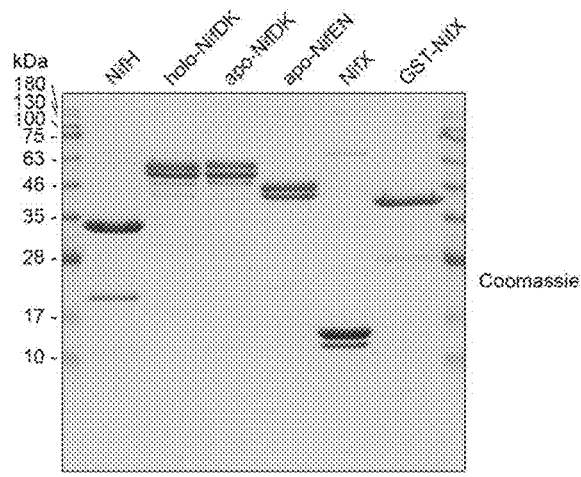

FIG. 19. Proteins used for NifB-dependent in vitro FeMo-co synthesis and apo-NifDK activation assays.

Figure 20:
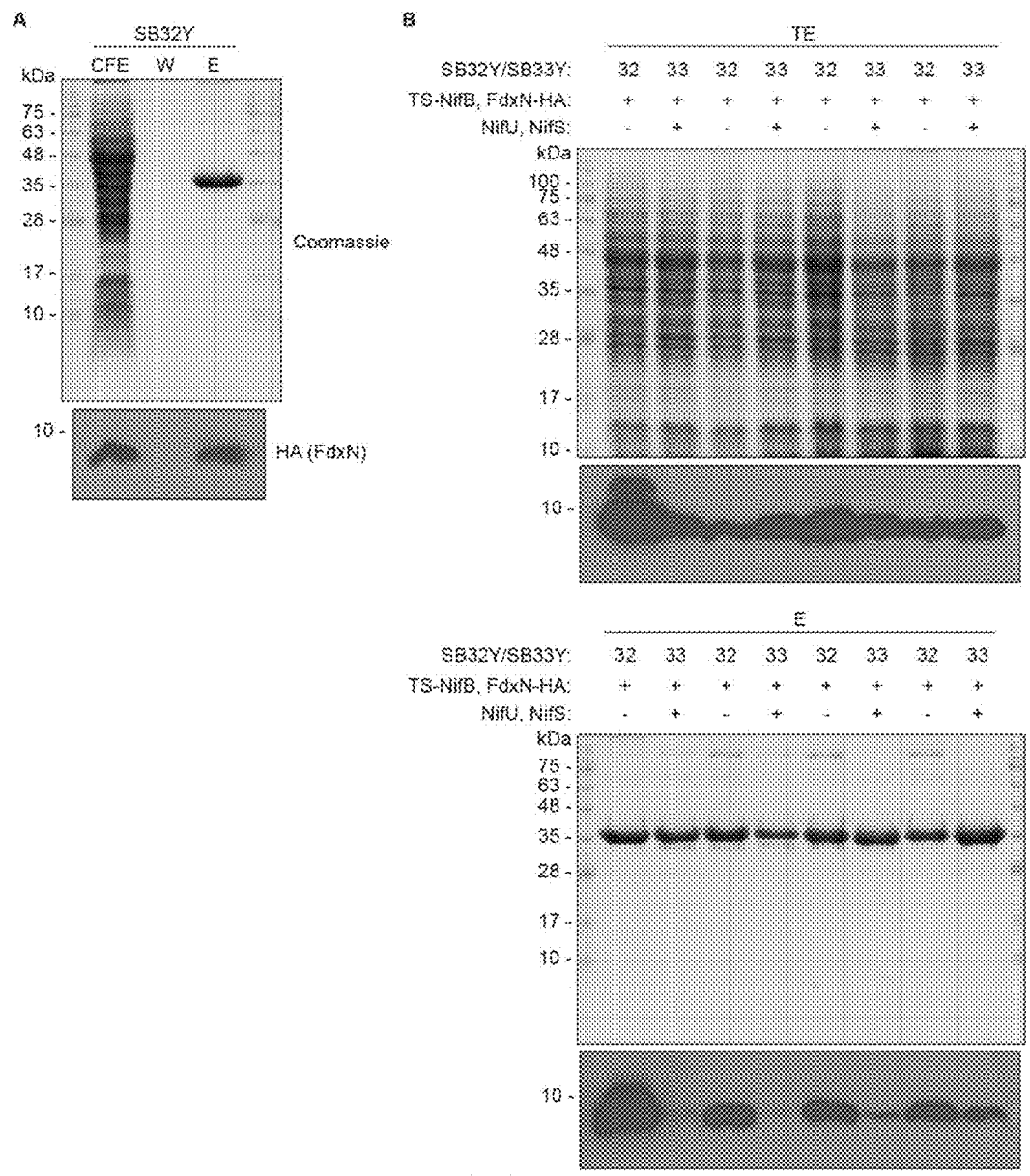

FIG. 20. Interaction between FdxN-HA and TS-NifB in presence (SB33Y) or absence (SB32Y) of NifU and NifS. (A) Coomassie staining and immunoblot analysis of FdxN-HA interacting with TS-NifBF (purified from SB32Y). CFE, cell-free extract; W, last wash fraction; E, biotin eluted fraction. (B) Coomassie staining and immunoblot analysis of FdxN-HA interacting with TS-NifBF (purified from SB32Y) and TS-NifBUSF (purified from SB33Y). TE, total extact; E, biotin eluted fraction.

Figure 21:
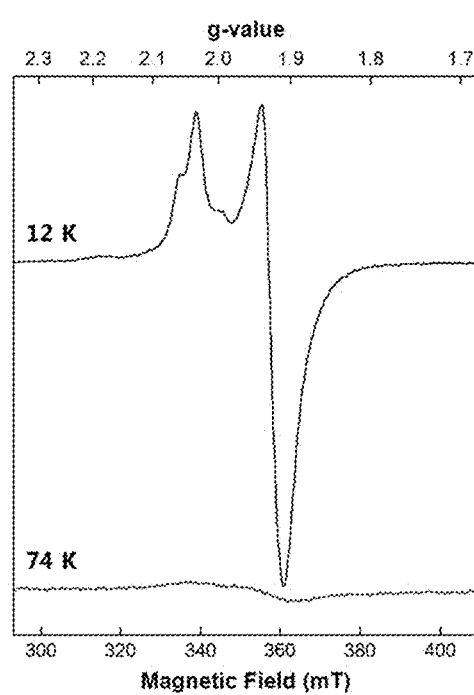

FIG. 21. X-band EPR spectra of TS-NifBUSF measured at two different temperatures.

Figure 22:
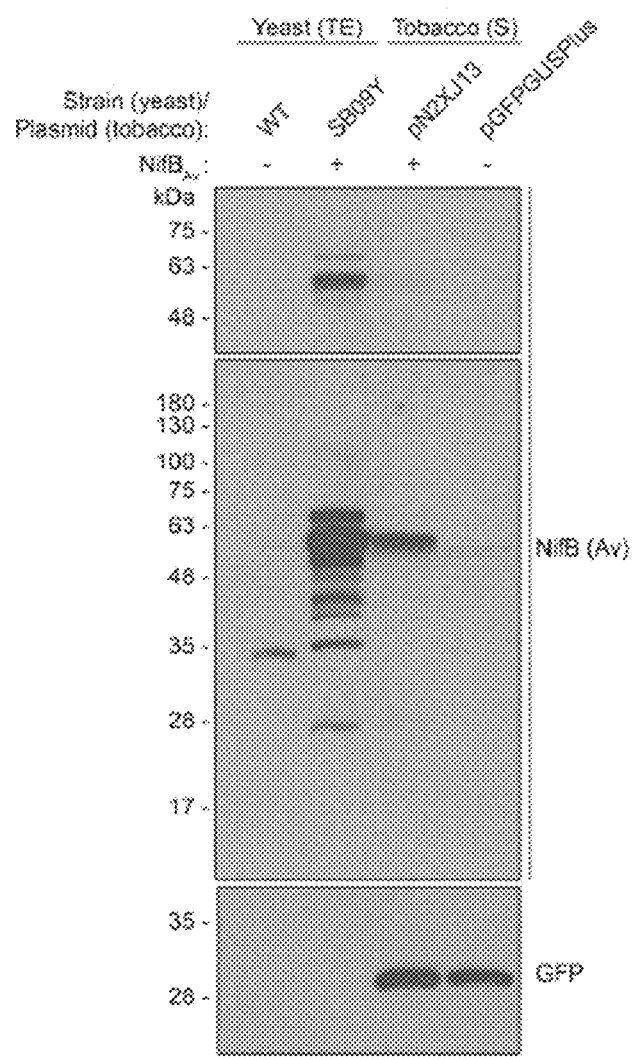

FIG. 22. 12 K X-band EPR spectra of two independently prepared TS-NifBUSF and TS-NifBUS showing identical EPR signals. The asterisk indicates a g=2 signal belonging to minor organic radical with unknown origin.

DETAILED DESCRIPTION OF THE INVENTION

The authors of the present invention have developed an efficient protein expression system that allows the expression of an active form of the protein NifB in eukaryotic cells under aerobic conditions. This expression system is based on the expression of the NifB protein in yeast and plant mitochondria together with NifU, NifS and FdxN proteins. The authors of the present invention have observed that using this expression system it is possible to express NifB in the yeast mitochondria and recover the protein in an active form. Thus, as shown in the examples of the present invention, the NifB protein obtained using the method developed by the inventors allows the in vitro synthesis of the FeMo cofactor (FeMo-co) which allows subsequent apo-NifDK activation and generation of active nitrogenase.

First Polynucleotide of the Invention

In a first aspect the invention relates to a polynucleotide encoding a fusion protein comprising NifB protein and a mitochondrial targeting peptide.

The term "polynucleotide" as used herein relates to a polymer formed by a variable number of monomers wherein the monomers are nucleotides, including ribonucleotides as well as deoxyribonucleotides. The polynucleotides include monomers modified by methylation as well as unmodified forms. The terms "polynucleotide" and "nucleic acid" are used indiscriminately in the present invention and include mRNA, cDNA and recombinant polynucleotides. As used in the present invention, polynucleotides are not limited to polynucleotides as they appear in nature, and also include polynucleotides where unnatural nucleotide analogues and inter-nucleotide bonds appear. Non-limitative examples of this type of unnatural structures include polynucleotides wherein the sugar is different from ribose, polynucleotides wherein the phosphodiester bonds 3'-5' and 2'-5' appear, polynucleotides wherein inverted bonds (3'-3' and 5'-5') appear and branched structures. Also, the polynucleotides of the invention include unnatural inter-nucleotide bonds such as peptide nucleic acids (PNA), locked nucleic acids (LNA), C1-C4 alkylphosphonate bonds of the methylphosphonate, phosphoramidate, C1-C6 alkylphosphotriester, phosphorothioate and phosphorodithioate type. In any case, the polynucleotides of the invention maintain the capacity to hybridize with target nucleic acids in a similar way to natural polynucleotides.

The term "fusion protein" as used herein, relates to proteins generated by gene technology which consist of two or more functional domains derived from different proteins. A fusion protein may be obtained by conventional means (e.g. by means of gene expression of the nucleotide sequence encoding for said fusion protein in a suitable cell). The fusion protein of the invention comprises NifB protein and a mitochondrial targeting peptide.

The term "NifB protein" or "NifB polypeptide" as used herein, refers to a polypeptide which naturally occurs in bacteria and which is involved in FeMo—Co synthesis by converting [4Fe-4S] clusters into NifB-co, an Fe—S cluster of higher nuclearity with a central C atom that serves as a precursor of FeMo—Co. NifB therefore catalyses the first committed step in the FeMo—Co synthesis pathway. The NifB-co product of NifB is able to bind to the NifE-NifN complex and can be shuttled from NifB to NifE-NifN by the metallocluster carrier protein NifX. As used herein, a "NifB protein" or a "NifB polypeptide" means a polypeptide comprising one or more of the conserved domain TIGR01290, the NifB conserved domain cd00852, the NifX-NifB superfamily conserved domain cl00252 and the Radical_SAM conserved domain cd01335. As used herein, NifB polypeptides include naturally occurring polypeptides which have been annotated as having NifB function but which do not have one of these domains. A naturally occurring NifB polypeptide typically has a length of between 440 and 500 amino acids and the natural monomer has a molecular weight of about 50 kDa. A great number of NifB polypeptides have been identified and numerous sequences are available in publically available databases. For example, NifB polypeptides have been reported from *Raoultella ornithinolytica* (Accession No. WP 041145602.1), *Kosakonia radicincitans* (WP_043953592.1), *Dickeya chrysanthemi* (WP_040003311.1), *Pectobacterium atrosepticum* (WP_011094468.1), *Brenneria goodwinii* (WP_048638849.1), *Halorhodospira halophila* (WP_011813098.1), *Methanosarcina barkeri* (WP_048108879.1), *Clostridium purinilyticum* (WP_050355163.1), *Geofilum rubicundum* (GA028552.1), *Gluconacetobacter diazotrophicus* PAl 5 (A9H5T3), *Roseiflexus* sp. RS-1 (A5USK4), *Cyanothece* sp. ATCC 51142 (A1KYD1), *Geobacter sulfurreducens* PCA (Q749E4), *Pseudomonas stutzeri* A1501 (Q93JV6), *Anabaena variabilis* ATCC 29413 (Q44481), *Ruminococcus albus* SY3 (A0A011U198), *Paenibacillus sabinae* (E1ABV1), *Syntrophobacter fumaroxidans* MPOB (AOLH03), *Clostridium pasteurianum* BC1 (NifNB) (R4KF67), *Rhodopseudomonas palustris* (Q6N0X9), *Desulfovibrio vulgaris* DSM19637

(B8DJB4), *Chlorobium tepidum* (Q8KC85), *Methanocaldococcus infernus* (D5VRM1), *Methanosarcina acetivorans* (Q8TIF7), *Methanobacterium thermoautotrophicum* (O27899), *Geobacter metallireducens* GS-15 (Q39XV1), *Synechococcus* sp. JA-3-3Ab (Q2JTL3), *Anabaena azollae*, '*Nostoc azollae*' 0708 (D7E3U6), *Cyanothece* sp. PCC 7425 (B8HWE0), *Rhodobacter capsulatus* SB 1003 (D5ANH7), Fusion of NifN and NifB from *Methanosarcina acetivorans* C2A (AAM07252.1 and AAM07541.1) and *Desulfovibrio salexigens* (WP_015850328.1). As used herein, a "functional NifB polypeptide" is a NifB polypeptide which is capable of forming NifB-co from [4Fe-4S] clusters.

The term "mitochondrial targeting peptide or mitochondrial targeting signal (MTS) or mitochondrial localization signal (MLS)" refers to a 10-60 amino acid long peptide that directs a target protein to the mitochondria. It consists of an alternating pattern of hydrophobic and positively charged amino acids to form what is called amphipathic helix. Mitochondrial targeting signal can contain additional signals that subsequently target the protein to different regions of the mitochondria, such as the mitochondrial matrix. In a preferred embodiment, mitochondrial targeting peptide is N-terminal (amino terminus) to the NifB protein. Non limiting examples of mitochondrial targeting peptides are the mitochondrial targeting peptides defined in Table I of von Heijne (supra.) as well as mitochondrial targeting peptides of a mitochondrial polypeptide selected from the group consisting of human cytochrome c oxidase subunit VIII, the P1 isoform of subunit c of human ATP synthase, aldehyde dehydrogenase targeting sequence, Glutaredoxin 5, Pyruvate dehydrogenase, Peptidyl-prolyl isomerase, Acetyltransferase, Isocitrate dehydrogenase, cytochrome oxidase, and the subunits of the FA portion of ATP synthase. In an embodiment, the mitochondrial targeting peptide is the mitochondrial targeting peptide of *Saccharomyces cerevisiae* (*S. cerevisiae*) superoxide dismutase (SOD).

Additional mitochondrial targeting peptides are shown below.

| ORF | Gene | Sequence |
|---|---|---|
| YBL022C | PIM1 | MLRTRTTKTLSTVARTTRAIQYYRSIAKTAAVSQRRF (SEQ ID NO: 9) |
| YBR037C | SCO1 | MLKLSRSANLRLVQLPAARLSGNGAKLLTQRGFFTVTRLW (SEQ ID NO: 10) |
| YBR039W | ATP3 | MLSRIVSNNATRSVMCHQAQVGILYKTNPVRTY (SEQ ID NO: 11) |
| YBR221C | PDB1 | MFSRLPTSLARNVARRAPTSFVRPSAAAAALRF (SEQ ID NO: 12) |
| YCR003W | MRPL32 | MNSLIFGKQLAFHKIVPTTAIGWLVPLGNPSLQIPGQK QLGSIHRWLREKLQQDHKDTEDKDFFSNNGILL (SEQ ID NO: 13) |
| YDL202W | MRPL11 | MLQLRFMPGWVPRNGFFGLKETIGTVHKRFY (SEQ ID NO: 14) |
| YDR298C | ATP5 | MFNRVFTRSFASSLRAA (SEQ ID NO: 15) |
| YDR337W | MRPS28 | MSIVGRNAILNLRISLCPLFMGKRSFVSSPVSN (SEQ ID NO: 16) |
| YIL070C | MAM33 | MFLRSVNRAVTRSILTTPKPAVVKSSWRVFTVANSKRCFTPAAIMR (SEQ ID NO: 17) |
| YKL192C | ACP1 | MFRSVCRISSRVAPSAYRTIMGRSVMSNTILAQRFY (SEQ ID NO: 18) |
| YLR395C | COX8 | MLCQQMIRTTAKRSSNIMTRPIIMKRS (SEQ ID NO: 19) |
| YNL052W | COX5A | MLRNTFTRAGGLSRITSVRFAQTHALS (SEQ ID NO: 20) |
| YNR001C | CIT1 | MSAILSTTSKSFLSRGSTRQCQNMQKALFALLNARHY (SEQ ID NO: 21) |
| YOR136W | IDH2 | MLRNTFFRNTSRRFL (SEQ ID NO: 22) |
| YPL059W | GRX5 | MFLPKFNPIRSFSPILRAKTLLRYQNRMY (SEQ ID NO: 23) |

In a preferred embodiment, the MTP is located N-terminally with respect to the NifB protein. In another embodiment, the MTP is located C-terminally with respect to the NifB protein.

In a preferred embodiment, the mitochondrial targeting peptide is formed by the first 69 amino acids of subunit 9 of the $F_0$ ATPase of *Neurospora crassa* (SU9) having the sequence (SEQ ID NO: 1)
1 MASTRVLASR LASQMAASAK VARPAVRVAQ VSKRTIQTGS PLQTLKRTQM

51 TSIVNATTRQ AFQKRAYSS.

In another preferred embodiment, the mitochondrial targeting peptide is formed by the first 29 amino acids of the yeast cytochrome c oxidase IV (COX4) protein having the sequence

```
                                    (SEQ ID NO: 2)
     1    MLSLRQSIRF FKPATRTLCS SRYLLQQKP.
```

In a preferred embodiment, the mitochondrial targeting peptide is formed by a functionally equivalent variant of the sequences SEQ ID NO: 1 or 2. Functionally equivalent variant" is understood to mean all those peptides derived from the sequences SEQ ID NO: 1 or 2, by modification, substitution, insertion and/or deletion of one or more amino acids, whenever the function is substantially maintained.

It may be useful in some embodiments of this invention to use multiple tandem copies of a chosen mitochondrial targeting peptide. The coding sequence for a duplicated o multiplied targeting peptide may be obtained through genetic engineering from an existing mitochondrial targeting peptide. The amount of mitochondrially-targeted peptide can be measured by cellular fractionation, followed by, for example, quantitative immunoblot analysis. Thus, in the present invention mitochondrial targeting peptide encompass one or more copies of one amino acid peptide that directs a target protein to the mitochondria. In a preferred embodiment, the mitochondrial targeting peptide comprises two copies of a chosen mitochondrial targeting peptide. In another embodiment, the mitochondrial targeting peptide comprises three copies of a chosen mitochondrial targeting peptide. In another embodiment, the mitochondrial targeting peptide comprises four copies or more of a chosen mitochondrial targeting peptide.

In a particular embodiment, the mitochondrial targeting peptide comprises a two tandem copies of the mitochondrial targeting peptide of *Saccharomyces cerevisiae* (*S. cerevisiae*) superoxide dismutase (SOD), or of sequences SEQ ID NO: 1 or 2.

In a particular embodiment, the polynucleotide of the invention further comprises at least one peptide tag adequate for detection, purification or solubilization of the fusion protein. The peptide tag may be bound to the C-terminal or N-terminal domain of said fusion protein. In a preferred embodiment, said tag is N-terminal to the NifB protein. In a still more preferred embodiment the peptide tag is N-terminal to NifB and the mitochondrial targeting peptide is N-terminal to said peptide tag.

Said tag is generally a peptide or amino acid sequence which can be used in the isolation or purification of said fusion protein. Thus, said tag is capable of binding to one or more ligands, for example, one or more ligands of an affinity matrix such as a chromatography support or bead with high affinity. The skilled person will understand that the tag is located in the fusion protein at a location which does not result in the removal of the tag from the NifB protein once the mitochondrial targeting signal is cleaved off after import into the mitochondria. Moreover, the tag has to be located so that it does not interfere with the mitochondria import machinery. Thus, in a preferred embodiment, the polynucleotide of the invention encodes a fusion protein that comprises, in the N- to C-terminal order, an N-terminal mitochondrial targeting peptide, the detection/purification tag and the NifB protein. In other embodiment, the polynucleotide of the invention encodes a fusion protein that comprises, in the N- to C-terminal order, an N-terminal mitochondrial targeting peptide, the NifB protein and the detection/purification tag.

In a more preferred embodiment, in the polynucleotide encoding the fusion protein of the invention, the peptide tag is N-terminal to NifB and the mitochondrial targeting peptide is N-terminal to said peptide tag An example of said tag is a histidine tag (His-tag or HT), such as a tag comprising several residues of histidine (for example 6 residues [His6 or H6]; 8 residues [His8 or H8]); 10 residues [His10 or H10], which can bind to a column of nickel ($Ni^{2+}$) or cobalt ($Co^{2+}$) with high affinity. His-tag has the desirable feature that it can bind its ligands under conditions that are denaturing to most proteins and disruptive to most protein-protein interactions. Thus, it can be used to remove the bait protein tagged with H6 following the disruption of protein-protein interactions with which the bait has participated.

In a preferred embodiment, the tag is the Twin-Strep tag having the sequence

```
                                    (SEQ ID NO: 3)
     1    WSHPQFEKGG GSGGGSGGSA WSHPQFEK.
```

The Twin-Strep tag makes reference to an improved version of the eight amino acid Strep-tag II (Witte et al 2004) or a variant of the same. In another embodiment the peptide tag is the polypeptide of sequence SEQ ID NO: 4 (WSHPQFEK).

Additional illustrative, non-limitative, examples of tags useful for detecting, isolating or purifying a fusion protein include fluorescent tags such as fluorescein, resourfin and derivatives thereof, Arg-tag, FLAG-tag, Strep-tag, an epitope capable of being recognized by an antibody, such as c-myc-tag (recognized by an anti-c-myc antibody), SBP-tag, S-tag, calmodulin binding peptide, cellulose binding domain, chitin binding domain, glutathione S-transferase-tag, maltose binding protein, Glutathione S-Transferase tag, Maltose Binding Protein, Calmodulin Binding Peptide, Intein-Chitin Binding Domain tag, FLAG epitope tag, c-Myc epitope tagan amino acid sequence such as Ala-His-Gly-His-Arg-Pro (SEQ ID NO: 5); Pro-Ile-His-Asp-His-Asp-His-Pro-His-Leu-Val-Ile-His-Ser (SEQ ID NO: 6); Gly-Met-Thr-Cys-X-X-Cys (SEQ ID NO: 7); 3-galactosidase and the like.

In another embodiment, the fusion protein comprising the NifB protein and a mitochondrial targeting peptide also comprises a fluorescent protein. By "fluorescent protein" is meant any protein capable of emitting light when excited with appropriate electromagnetic radiation/light (i.e. light of an appropriate wavelength). The fluorescent protein will absorb energy of a specific wavelength and re-emit energy at a different (but equally specific) wavelength. The fluorescent protein can be N or C terminus to the NifB protein. Fluorescent proteins that can be used include biological and chemical fluorophores. Exemplary biological fluorophores comprise T-sapphire, Cerulean, mCFPm, CyPet, EGFP, PA-EGFP, Emerald, EYFP, Venus, mCitrine, mKO1 (monomeric Kusabira orange 1) mOrange, DSRed, JRed, mStrawberry, mCherry, PA-mCherry, mRuby, Tomato, mPlum, mKate, mKatushka, Kaede, Halotag, and superecliptic fluorine. Exemplary chemical fluorophores comprise Alexafluor, Rhodamine, BODIPY, Tetramethylrhodamine, Cyanin dyes, Fluorescein, Quantum dots, IR dyes, FM dyes, ATTO dye. In another embodiment, the detection tag is a tetracysteine motif. As uses herein, "tetracysteine motif" refers to a short amino acid sequence containing four cysteines (CCXXCC) (SEQ ID NO: 8) encoded at the N or C terminal of the NifB protein which binds to biarsenical dyes, ReAsH (red fluorescent) and FlAsh (green fluorescent), with high specificity even in live cells. FlAsH is a fluorescein derivative, modified to contain two arsenic atoms at a set distance from each other. ReAsH is based on resoruf in and has been similarly modified.

The skilled person will understand that it may be desirable that fusion protein further comprises a flexible peptide that binds the NifB protein, and the purification/detection tag or/and the mitochondrial targeting peptide.

As used herein, the term "flexible peptide", "spacer peptide" or "linker peptide" refers to a peptide that covalently binds the NifB protein to the peptide tag/mitochondrial targeting peptide and/or that covalently binds the peptide tag and the mitochondrial targeting peptide, which is not part of neither the NifB protein nor the mitochondrial targeting peptide or the peptide tag, allowing movement of one with respect to the other, without causing a substantial detrimental effect on the function of either the protein or the moiety. In a preferred embodiment, said flexible peptide binds the NifB protein and the mitochondrial targeting peptide or the NifB protein and the peptide tag, substantially without causing a detrimental effect on the function of neither the NifB protein nor the mitochondrial targeting peptide or the peptide tag. It is not necessary that the NifB protein and the mitochondrial targeting peptide are arranged in that order and, in this case, the invention contemplates fusion proteins in which the NifB protein is located at amino-terminal position relative to the mitochondrial targeting peptide, and wherein the NifB protein is located at carboxyl-terminal position relative to the cell penetrating peptide, and wherein the peptide tag is linked to the mitochondrial targeting peptide. In addition, the invention contemplates fusion proteins in which NifB protein is located at amino-terminal position relative to the peptide tag, and wherein the NifB protein is located at carboxyl-terminal position relative to the peptide tag, and wherein the mitochondrial targeting peptide is linked to the peptide tag.

The flexible peptide comprises at least one amino acid, at least two amino acids, at least three amino acids, at least four amino acids, at least five amino acids, at least six amino acids, at least seven amino acids, at least eight amino acids, at least nine amino acids, the least 10 amino acids, at least 12 amino acids, at least 14 amino acids, at least 16 amino acids, at least 18 amino acids, at least 20 amino acids, at least 25 amino acids, at least 30 amino acids, at least 35 amino acids, at least 40 amino acids, the least 45 amino acids, at least 50 amino acids, at least 60 amino acids, at least 70 amino acids, at least 80 amino acids, at least 90 amino acids, or about 100 amino acids. In some embodiments the flexible peptide will permit the movement of one protein with respect to the other in order to increase solubility of the protein and/or to improve its CPP activity. If desired, the flexible peptide can encompass either repetitions of polyglycine or combinations of glycine, proline and alanine residues.

In a still more preferred embodiment, the polynucleotide of the invention is operatively linked to suitable transcriptional or translational regulatory elements.

As used herein, the terms "operatively linked" or "operably linked" mean that a sequence which functions as a promoter is connected or linked to a coding region in such a way that the transcription of that coding region is controlled and regulated by that promoter. Means for operatively linking a promoter to a coding region to regulate both upstream and downstream are well known in the art.

The transcriptional or translational regulatory elements can be derived from, for example, mammalian, microbial, viral, or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. The regulatory sequences useful for the present invention can be nuclear promoter sequences or, alternatively, enhancer sequences and/or regulatory sequences which increase the expression of the nucleotide sequence, suppressor sequences, transcriptional start sites, transcriptional stops sites, polyadenilation sites and the like. A great number of expression control sequences are known in the art and may be utilized according to the present invention. In the case of eukaryotic cells they comprise normally promoters ensuring initiation of transcription and optionally poly-A signals ensuring termination of transcription and stabilization of the transcript, for example, those of the 35S RNA from Cauliflower Mosaic Virus (CaMV). Others promoters commonly used are the Figwort Mosaic virus promoter, the polyubiquitin promoter and the actin promoter for ubiquitous expression. Possible regulatory elements permitting expression in eukaryotic host cells comprise e.g. SV40 promoter, Rous Sarcoma virus promoter, CMV enhancer, SV40 enhancer. The regulatory sequences useful for the present invention also encompass eukaryotic translational enhancers such as the CAMV omega sequences or the inclusion of introns which can increase the expression level by up to 100-fold (Maiti et al., 1997, Transgenic Research 6: 143-156). The promoter can be constitutive or inducible. If the constant expression of the polynucleotide is desired, then a constitutive promoter is used. An "inducible" promoter is used when is desired a regulated expression of the polynucleotide depending on physiological or developmental conditions. Typical promoters suitable for expression in yeast cells such include, but are not limited to:

Constitutive promoters such as, for example, the alcohol dehydrogenase (ADH1) promoter, the 1-α elongation factor (TEF) promoter and the promoter of the gene which encodes triose phosphate isomerase (TPI), the glyceraldehyde 3-phosphate dehydrogenase (GPD) promoter and the 3-phosphoglycerate kinase (GPK) promoter, the MRP7 promoter and the alcohol oxidase (AOX1) promoter.

Inducible promoters such as, for example, the metallothionein (CUP1) promoter, the expression of which is regulated by means of adding copper to the culture medium, the promoter of the gene which encodes the FUS1 gene or the FUS2 gene, the expression of which is activated in the presence of pheromones (the a factor) as described in U.S. Pat. No. 5,063,154, the TET promoter, the expression of which is regulated in the presence of tetracyclines, the GAL1-10, GALL, GALS promoters which are activated in the presence of galactose, the VP16-ER promoter, inducible by estrogens, and the phosphatase (PH05) promoter the expression of which is activated in the presence of phosphate and the HSP150 heat shock protein promoter, the expression of which is activated at a high temperature.

Repressible promoters such as, for example, the *S. cerevisiae* enolase (ENO-1) gene promoter, the expression of which can be repressed when the microorganism is grown in a non-fermentable carbon source, as well as promoters the expression of which is subject to glucose repression such that the expression will be repressed when part of the lactose has been hydrolyzed and the concentration of glucose in the medium starts to increase, the *S. cerevisiae* glyceraldehyde-3-phosphate dehydrogenase (ADH2/GAP) promoter and the galactokinase (GAL I) promoter.

Preferably, in those cases in which the heterologous protein is suspected of being toxic to the host cell, the promoter used to regulate its expression is advisably an inducible promoter such that the expression of the protein of interest can be delayed until sufficient biomass levels have been achieved.

In a preferred embodiment, the expression of nifB gene is directed from GAL1 promoter. Optimal conditions for cell grown and NifB expression under GAL1 promoter are for example, those wherein transformants are grown under aerobic conditions to saturation in minimal selective medium containing high levels of glucose, such as 2% glucose at 30° C. Once the glucose is consumed 2% galactose can be added to the cell culture to induce NifB protein expression. After induction of NifB expression, cells can be cultured for 24-72 hours allowing maximum protein production.

Typical promoters suitable for expression in plants have been described in the literature. Such promoters may be obtained from plants, plant viruses, or plant commensal, saprophytic, symbiotic, or pathogenic microbes and include, but are not limited to, the nopaline synthase (NOS) and octopine synthase (OCS) promoters (which are carried on tumor-inducing plasmids of *Agrobacterium tumefaciens*), the cauliflower mosaic virus (CaMV) 19S and 35S promoters, the light-inducible promoter from the small subunit of ribulose 1,5-bisphosphate carboxylase (ssRUBISCO, a very abundant plant polypeptide), the rice Acti promoter, the Figwort Mosaic Virus (FMV) 35S promoter, the sugar cane bacilliform DNA virus promoter, the ubiquitin promoter, the peanut chlorotic streak virus promoter, the comalina yellow virus promoter, the chlorophyll a/b binding protein promoter, and meristem enhanced promoters Act2, Act8, Act11 and EF1a and the like. All of these promoters have been used to create various types of DNA constructs which have been expressed in plants (see e.g., McElroy et al., 1990; Barry and Kishore, U.S. Pat. No. 5,463,175) and which are within the scope of the present invention. Chloroplast and plastid specific promoters, chloroplast or plastid functional promoters, and chloroplast or plastid operable promoters are also envisioned.

One set of preferred promoters are constitutive promoters such as the CaMV35S or FMV35S promoters that yield high levels of expression in most plant organs. Enhanced or duplicated versions of the CaMV35S and FMV35S promoters may be particularly useful in the practice of this invention (Kay et al, 1987; Rogers, U.S. Pat. No. 5,378,619), In addition, it may also be preferred to bring about expression of the NifB protein in specific tissues of the plant, such as leaf, stem, root, tuber, seed, fruit, etc., and the promoter chosen should have the desired tissue and developmental specificity.

Therefore, promoter function should be optimized by selecting a promoter with the desired tissue expression capabilities.

In a preferred embodiment, the sequences which encode the fusion protein of the polynucleotide of the invention are codon optimized for expression in a eukaryotic cell. The term "codon optimized", as used herein, refers to the alteration of codons in nucleic acid molecules to reflect the typical codon optimization. See Narum D, et al., Infect. Immun. 2001; 69(12):7250-7253), Outchkourov N, et al., Protein Expr. Purif. 2002; 24(1):18-24, Feng L, et al., Biochemistry 2000; 39(50):15399-15409, and Humphreys D, et al., Protein Expr. Purif. 2000; 20(2):252-264.

In a more preferred embodiment, said codon optimization is for expression in yeast or plants.

Yeast cells belong to facultative anaerobic organisms and they obtain energy (ATP) by aerobic respiration if oxygen is present but they are also capable of switching to fermentation. "Yeast" is understood as any eukaryotic organism belonging to the ascomycetes type which includes the organisms generally known as yeasts as well as those generally known as filamentous fungi. The yeasts and filamentous fungi include *Pichia* sp (for example, *P. pastoris, P. finlandica, P. trehalophila, P. koclamae, P. membranaefaciens, P. minuta, P. opuntiae, P. thermotolerans, P. salictaria, P. guercuum, P. pijperi, P. stiptis, P. methanolica*), *Saccharomyces* (*S. cerevisiae*), *Schizosaccharomyces pombe, Kluyveromyces* (for example, *K. lactis, K. fragilis, K. bulgaricus, K. wickeramii, K. waltii, K. drosophilarum, K. thernotolerans*, and *K. marxianus, K. yarrowia*), *Trichoderma reesia, Neurospora crassa, Schwanniomyces, Schwanniomyces occidentalis, Penicillium, Totypocladium, Aspergillus* (for example, *A. nidulans, A. niger, A. oryzae*), *Hansenula polymorpha, Candida, Kloeckera, Torulopsis*, and *Rhodotorula, Hansenula, Kluyveromyces* sp. (for example, *Kluyveromyces lactis*), *Candida albicans, Aspergillus* sp (for example, *Aspergillus nidulans, Aspergillum niger, Aspergillus oryzae*), *Trichoderma reesei, Chrysosporium luchiowense, Fusarium* sp. (for example, *Fusarium gramineum, Fusarium venenatum*), *Physcomitrella patens*.

Virtually any yeast can be considered in the present invention; however, in a particular embodiment, said yeast is yeast from the *Saccharomyces* genus, such as *S. cerevisiae*.

The term "plant" as used herein as a noun refers to whole plants and refers to any member of the Kingdom Plantae, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, cotyledons, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are cotyledon, embryo and embryo axis. The invention accordingly includes plants and plant parts and products comprising these.

Plants contemplated for use in the practice of the present invention include both monocotyledons and dicotyledons. Target plants include, but are not limited to, the following: cereals (for example, wheat, barley, rye, oats, rice, maize, sorghum and related crops); grapes; beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape or other Brassicas, mustard, poppy, olives, sunflowers, safflower, flax, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers).

Virtually any plant can be considered in the present invention; however, in a particular embodiment, said plant is *Nicotina benthamiana*.

In a still more preferred embodiment the codon optimization is for expression in *Saccharomyces cerevisae* or *Nicotiana benthamiana*.

In a preferred embodiment, the NifB protein is from a prokaryotic organism. In a more preferred embodiment, said bacteria belongs to nitrogen-fixing bacteria, including free living nitrogen fixing bacteria, associative nitrogen fixing bacteria and symbiotic nitrogen fixing bacteria. Free living nitrogen fixing bacteria are capable of fixing significant levels of nitrogen without the direct interaction with other organisms. Without limitation said free living nitrogen fixing bacteria include the members of the genera *Azotobacter, Beijerinckia, Klebsiella, Cyanobacteria* (classified as aerobic organisms) and the members of the genera *Clostridium, Desulfovibrio* and the named Purple sulphur bacteria, Purple non-sulphur bacteria and Green sulphur bacteria. Associative nitrogen fixing bacteria are those prokaryotic organisms that are able to form close associations with several members of the Poaceae (grasses). These bacteria fix appreciable amounts of nitrogen within the rhizosphere of the host plants. Members of the genera *Azospirillum* are representative of associative nitrogen fixing bacteria.

Symbiotic nitrogen fixation bacteria are those microorganisms which fix nitrogen symbiotically by partening with a host plant. The plant provides sugars from photosynthesis that are utilized by the nitrogen fixing microorganism for the energy it needs for nitrogen fixation. Members of the genera *Rhizobia* are representative of associative nitrogen fixing bacteria.

In a still more preferred embodiment, said NifB protein is from *Azotobacter vinelandii* (*A. vinelandii*) or *Methanocaldococcus infernus* (*M. infernus*). The term "is from" or "isolated from" means that said polynucleotide or encoded polypeptide is substantially separated or purified from other nucleic acid or encoded polypeptide in the cell of the organism in which the nucleic acid or encoded polypeptide naturally occurs. The term isolated thus encompasses nucleic acid purified by standard purification methods for nucleic acids or encoded polypeptide. The term also embraces nucleic acids or encoded polypeptide prepared by recombinant expression in a host cell as well as chemically synthesized nucleic acids or encoded polypeptide thereof.

A suitable polynucleotide for the expression of NifB has the following sequence, a sequence ending the SU9 mitochondrial targeting sequence (underlined) and a yeast optimized DNA encoding *A. vinelandii* NifB as shown below wherein the translated amino acid sequences (SEQ ID NO: 25) is shown below the nucleic acid sequence (SEQ ID NO: 24).

```
SU9-NifU
ATGGCCTCCACTCGTGTCCTCGCCTCTCGCCTGGCCTCCCAGATGGCTGCTTCCGCCAAG
 M   A   S   T   R   V   L   A   S   R   L   A   S   Q   M   A   A   S   A   K

GTTGCCCGCCCTGCTGTCCGCGTTGCTCAGGTCAGCAAGCGCACCATCCAGACTGGCTCC
 V   A   R   P   A   V   R   V   A   Q   V   S   K   R   T   I   Q   T   G   S

CCCCTCCAGACCCTCAAGCGCACCCAGATGACCTCCATCGTCAACGCCACCACCCGCCAG
 P   L   Q   T   L   K   R   T   Q   M   T   S   I   V   N   A   T   T   R   Q

GCTTTCCAGAAGCGCGCCTACTCTTCCAGGCCTTGGGACTACTCTGAAAAGGTTAAGGAA
 A   F   Q   K   R   A   Y   S   S   R   P   W   D   Y   S   E   K   V   K   E

CATTTCTACAATCCAAAGAACGCCGGTGCTGTAGAAGGTGCAAACGCCATTGGTGACGTT
 H   F   Y   N   P   K   N   A   G   A   V   E   G   A   N   A   I   G   D   V

GGTTCATTATCCTGTGGTGACGCTTTGAGATTAACATTGAAAGTTGACCCTGAAACCGAT
 G   S   L   S   C   G   D   A   L   R   L   T   L   K   V   D   P   E   T   D

GTCATCTTGGACGCAGGTTTTCAAACTTTCGGTTGCGGTTCTGCTATTGCATCTTCATCC
 V   I   L   D   A   G   F   Q   T   F   G   C   G   S   A   I   A   S   S   S

GCTTTGACTGAAATGGTTAAGGGTTTGACATTGGATGAAGCATTGAAAATCTCAAACCAA
 A   L   T   E   M   V   K   G   L   T   L   D   E   A   L   K   I   S   N   Q

GATATCGCTGACTATTTGGATGGTTTGCCACCTGAAAAGATGCATTGTTCCGTCATGGGT
 D   I   A   D   Y   L   D   G   L   P   P   E   K   M   H   C   S   V   M   G
```

```
AGAGAAGCCTTACAAGCTGCAGTAGCTAACTACAGAGGTGAAACCATTGAAGATGACCAC
 R   E   A   L   Q   A   A   V   A   N   Y   R   G   E   T   I   E   D   D   H

GAAGAAGGTGCATTGATATGTAAATGCTTTGCCGTTGATGAAGTTATGGTCAGAGATACC
 E   E   G   A   L   I   C   K   C   F   A   V   D   E   V   M   V   R   D   T

ATAAGAGCAAATAAGTTAAGTACTGTAGAAGATGTTACTAACTACACAAAAGCTGGTGGT
 I   R   A   N   K   L   S   T   V   E   D   V   T   N   Y   T   K   A   G   G

GGTTGTTCTGCTTGCCATGAAGCAATAGAAAGAGTTTTGACAGAAGAATTGGCCGCTAGA
 G   C   S   A   C   H   E   A   I   E   R   V   L   T   E   E   L   A   A   R

GGTGAAGTATTCGTTGCAGCCCCAATTAAAGCCAAAAAGAAAGTCAAGGTATTGGCTCCA
 G   E   V   F   V   A   A   P   I   K   A   K   K   K   V   K   V   L   A   P

GAACCTGCCCCAGCTCCTGTTGCAGAAGCCCCAGCTGCAGCCCCTAAGTTGTCAAATTTG
 E   P   A   P   A   P   V   A   E   A   P   A   A   A   P   K   L   S   N   L

CAAAGAATTAGAAGAATCGAAACAGTCTTGGCTGCAATAAGACCTACCTTGCAAAGAGAC
 Q   R   I   R   R   I   E   T   V   L   A   A   I   R   P   T   L   Q   R   D

AAAGGTGACGTCGAATTAATTGATGTAGACGGTAAAAATGTTTACGTCAAATTGACCGGT
 K   G   D   V   E   L   I   D   V   D   G   K   N   V   Y   V   K   L   T   G

GCTTGTACTGGTTGCCAAATGGCATCCATGACATTAGGTGGTATACAACAAAGATTGATC
 A   C   T   G   C   Q   M   A   S   M   T   L   G   G   I   Q   Q   R   L   I

GAAGAATTGGGTGAGTTCGTCAAAGTTATCCCAGTCTCCGCTGCCGCACACGCCCAAATG
 E   E   L   G   E   F   V   K   V   I   P   V   S   A   A   A   H   A   Q   M

GAAGTCTGA
 E   V   -
```

Another suitable polynucleotide for the expression of NifB comprises a sequence ending the SU9 mitochondrial targeting sequence (underlined), the Twin-Step tag (bold and underlined) and a yeast optimized DNA encoding *A. vinelandii* NifB (bold) and wherein the N-terminus for TS-NifB as deduced from N-terminal sequencing (SSSAW) is highlighted in grey. The sequence is shown below wherein the translated amino acid sequences (SEQ ID NO: 27) is shown below the nucleic acid sequence (SEQ ID NO: 26).

```
SU9-TwinStrep-NifB
ATGGCCTCCACTCGTGTCCTCGCCTCTCGCCTGGCCTCCCAGATGGCTGCTTCCGCCAAG
 M   A   S   T   R   V   L   A   S   R   L   A   S   Q   M   A   A   S   A   K GTTGCCCGCCCTGCTGTCCGCGTTGCTCAGGTCAGCAAGCGCACCATCCAGACTGGCTCC
 V   A   R   P   A   V   R   V   A   Q   V   S   K   R   T   I   Q   T   G   S CCCCTCCAGACCCTCAAGCGCACCCAGATGACCTCCATCGTCAACGCCACCACCCGCCAG
 P   L   Q   T   L   K   R   T   Q   M   T   S   I   V   N   A   T   T   R   Q GCTTTCCAGAAGCGCGCCTACTCTTCCTCAGCATGGAGTCATCCTCAGTTTGAGAAGGT
 A   F   Q   K   R   A   Y   S   S   S   A   W   S   H   P   Q   F   E   K   G GGAGGTTCAGGTGGTGGAAGCGGTGGATCTGCTTGGTCACATCCACAATTTGAAAAACTC
 G   G   S   G   G   S   G   G   S   A   W   S   H   P   Q   F   E   K   L GAAGGATCCATGGAAAAGATGTCCAAGTTCTCCCATTTGTTGAAAGCTCATCCATGCTTC
 E   G   S   M   E   K   M   S   K   F   S   H   L   L   K   A   H   P   C   F AACGAAAAGGTTCATGATAAGTACGGTAGAGTTCATTTGCCAGTTGCTCCAAGATGTAAC
 N   E   K   V   H   D   K   Y   G   R   V   H   L   P   V   A   P   R   C   N ATTGCTTGTAAGTTCTGCAAGAGGTCCGTTTCTAAAGAATGTTGTGAACATAGACCAGGT
 I   A   C   K   F   C   K   R   S   V   S   K   E   C   C   E   H   R   P   G GTTTCTTTGGGTGTTTTGAAACCAGAAGATGTTGAGGACTACCTGAAAAAGATCTTGAAA
 V   S   L   G   V   L   K   P   E   D   V   E   D   Y   L   K   K   I   L   K GAGATGCCAAACATCAAGGTTGTTGGTATTGCTGGTCCTGGTGATTCTCTGTTTAACAAA
 E   M   P   N   I   K   V   V   G   I   A   G   P   G   D   S   L   F   N   K GAAACTTTCGAAACCCTGAAGATCATCGACGAAAAGTTTCCCAACTTGATTAAGTGCATT
 E   T   F   E   T   L   K   I   I   D   E   K   F   P   N   L   I   K   C   I
```

```
TCCACCAACGGTCTGTTGTTGTCTAAGTACTACAAGGATTTGGCCAACTTGAACGTTAGA
 S  T  N  G  L  L  L  S  K  Y  Y  K  D  L  A  N  L  N  V  R

ACTATTACCGTTACTGTCAACGCCATTAAGCCAGAAATCTTGGAAAAAATCGTTGACTGG
 T  I  T  V  T  V  N  A  I  K  P  E  I  L  E  K  I  V  D  W

GTTTACTACGACAAGAAGTTGTATAGAGGTTTGGAAGGTGCCAAGTTGTTGATCGAAAAA
 V  Y  Y  D  K  K  L  Y  R  G  L  E  G  A  K  L  L  I  E  K

CAAATCGAAGGTATCAAGAAGGCCTCCGAAGAAGATTTCATTATCAAGATCAACACCGTC
 Q  I  E  G  I  K  K  A  S  E  E  D  F  I  I  K  I  N  T  V

TTGATCCCAGAAATCAACATGGATCACGTTGTTGAAATTGCCAAGTTCTTCAAGGATTAC
 L  I  P  E  I  N  M  D  H  V  V  E  I  A  K  F  F  K  D  Y

GCCTACGTTCAAAACATCATTCCATTGATTCCACAGTACAAGATGAAGGAATTGAGAGCA
 A  Y  V  Q  N  I  I  P  L  I  P  Q  Y  K  M  K  E  L  R  A

CCAACTTGCGAAGAAATCAAAAAGGTCAGAAAAGAGTGCGAGAAGTACATCCCACAATTC
 P  T  C  E  E  I  K  K  V  R  K  E  C  E  K  Y  I  P  Q  F

AGAGCTTGTGGTCAATGTAGAGCTGATGCTGTTGGTCTGATCAAAGAAAAAGAGCTGTTG
 R  A  C  G  Q  C  R  A  D  A  V  G  L  I  K  E  K  E  L  L

AAAGAGTTTTTCAAAGAGAAGAACAAAGAAAAGAACATCAAGCTGGAAGTGTTCGACTTG
 K  E  F  F  K  E  K  N  K  E  K  N  I  K  L  E  V  F  D  L

AAGCACTTCTCTCATTGA
 K  H  F  S  H  -
```

Expression Vectors and Cells of the Invention

In another aspect, the invention refers to an expression vector comprising the first polynucleotide of the invention.

The term "expression vector" refers to a replicative DNA construct used for expressing DNA which encodes the polypeptide of the invention and which includes a transcriptional unit comprising the assembly of (1) genetic element(s) which play a regulatory role in gene expression, for example promoters, operators or enhancers, operatively bound to (2) a DNA sequence encoding the polypeptide of the invention which is transcribed into messenger RNA and translated into protein and (3) suitable sequences to initiate and to terminate the transcription and translation.

The vectors that can be used in the context of the present invention normally include a genetic marker, a replication origin in bacteria or yeasts, multiple cloning sites, and a genetic marker. The genetic marker is usually a gene conferring resistance to an antibiotic or alternatively, an auxotrophic marker in the case of yeasts.

The yeast vectors suitable for the present invention can be based on the following types of plasmids:

Multicopy autonomous plasmids: These plasmids contain sequences which allow generating multiple copies of said vectors. These sequences can be the so-called 2μ such as the one which appears in episomal plasmids (YEp or yeast episomal plasmids) or ARS-type sequences such as those which appear in replication plasmids (YRps or yeast replication plasmids). Examples of vectors based on plasmids of this type are p426GPD, p416GPD, p426TEF, p423GPD, p425GPD, p424GPD or p426GAL, YEp24 and YEplac.

Single copy autonomous plasmids: Plasmids which contain the autonomous replication sequence ARS1 and a centromere sequence (CEN4). Plasmids of this type include the centromere plasmids (YCps or yeast centromere plasmids).

Integrating plasmids: Plasmids which are capable of being integrated into the host cell genome. Plasmids of this type include integrating plasmids (YIPs or yeast integrating plasmids). Examples of vectors based on plasmids of this type are pRS303, pRS304, pRS305 or pRS306 and the like.

Generally, all the vectors mentioned by Sikorski ("Extrachromosomal cloning vectors of Saccharomyces cerevisiae", in Plasmid, A Practical Approach, Ed. K. G. Hardy, IRL Press, 1993) and by Ausubel et al. ("Yeast Cloning Vectors and Genes" Current Protocols in Molecular Biology, Section II, Unit 13.4, 1994) are useful in the context of the present invention.

Preferred plant transformation vectors include those derived from a Ti plasmid of Agrobacterium tumefaciens, as well as those disclosed, e.g., by Herrera-Estrella (1983), Bevan (1983), Klee (1985) and Eur. Pat. Appl. No. EP 0120516 (each specifically incorporated herein by reference). In addition, plant preferred transformation vectors directed to chloroplast or plastid transformation include those disclosed in U.S. Pat. No. 5,693,507 (1997), U.S. Pat. No. 5,451,513 (1995), McBride et al, (1995), Staub et al. (1995a), Staub et al. (1995b), and WO 95/24492.

In another aspect, the invention relates to a eukaryotic cell containing the polynucleotide according to the invention or the expression vector containing the polynucleotide according to the invention.

In another preferred embodiment, said eukaryotic cell grows under aerobic conditions. The term "aerobic conditions" as used herein refers to an oxygenated environment. Eukaryotic cells which grow under aerobic conditions include: facultative anaerobes organisms, which include organisms which can use oxygen, but also have anaerobic methods of energy production; obligate aerobes organisms, which require oxygen for aerobic cellular respiration wherein said organisms use oxygen to oxidize substrates (i.e. sugars and fats) in order to obtain energy; microaerophiles organisms, which include organisms that may use oxygen but at low concentrations; and aerotolerant organisms, which are those organisms that can survive in the presence of oxygen, but they are anaerobic because they do not use oxygen as a terminal electron acceptor.

In a still more preferred embodiment, said eukaryotic cell is a yeast cell or a plant cell. Yeast and plants suitable for receiving the polynucleotide of the invention have been defined in the context of the first polynucleotide of the invention. In a still preferred embodiment the eukaryotic cell ins *Saccharomyces cerevisae* of *Nicotina benthamiana*.

In another aspect, the invention relates to the use of an expression vector according to the invention or of a cell according to the invention for expressing the NifB protein.

Method for Expressing the NifB Protein in a Eukaryotic Cell

In another aspect, the invention relates to a method for expressing the NifB protein in a eukaryotic cell comprising the steps of:
  (i) introducing into said cell a polynucleotide according to the first aspect of invention or a vector comprising said polynucleotide,
  (ii) growing said cell under conditions allowing the expression of said oxygen-sensitive protein and, if desired;
  (iii) purifying said oxygen-sensitive protein under anaerobic conditions.

In the first step the method to express the NifB protein in a eukaryotic cell (thereinafter, first method of the invention) comprises introducing into said eukaryotic cell the first polynucleotide or the first vector according to the invention.

The term "introducing into eukaryotic cell the polynucleotide of the invention or introducing into eukaryotic cell the expression vector of the invention" refers to a process for delivering said nucleic acid into said cell, preferably yeast or plant cells. In a preferred embodiment the polynucleotide or the expression vector in transiently introduced into the eukaryotic cell. In another embodiment polynucleotide or the expression vector are stably integrated in the genome of the eukaryotic cell. In a still further embodiment, the polynucleotide or the expression vector is is integrated into the nuclear genome of the cell.

Methods suitable for introducing a DNA molecule into a yeast cell include but are not limited to:
  Transformation of spheroplasts which entails removing the cell wall of the yeast and contacting the spheroplasts with the plasmid in the presence of PEG.
  Transformation with Li+, which entails the treatment of yeast cells with monovalent alkaline cations (Na+, K+, Rb+, Cs+ and Li+) in combination with PEG to stimulate DNA uptake by the intact cells.
  Gen gun which entails bombarding cells with microprojectiles coated with the exogenous DNA.
  Electroporation, which entails administering electrical pulses to the yeasts which results in the opening of pores in the membrane of the spheroplasts and intact yeast cells.

Transformants are grown in an appropriate nutrient medium, and, where appropriate, maintained under selective pressure to insure retention of endogenous DNA. Where expression is inducible, growth can be permitted of the yeast host to yield a high density of cells, and then expression is induced. The non-yeast protein can be harvested by any conventional means, and purified by chromatography, electrophoresis, dialysis, solvent-solvent extraction, and the like.

Methods suitable for introducing a DNA molecule into a plant cell include but are not limited to: (1) chemical methods (Graham et al., 1973); (2) physical methods such as microinjection (Capecchi, 1980); electroporation (see, for example, WO 87/06614, U.S. Pat. Nos. 5,472,869, 5,384,253, WO 92/09696 and WO 93/21335); and the gene gun (see, for example, U.S. Pat. Nos. 4,945,050 and 5,141,131); (3) viral vectors (Clapp, 1993; Lu et al., 1993; Eglitis et al., 1988); and (4) receptor-mediated mechanisms (Curiel et al., 1992; Wagner et al., 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to being an effective means of reproducibly transforming monocots, is that neither the isolation of protoplasts, nor the susceptibility of *Agrobacterium* infection are required. A particle delivery system suitable for use with the present invention is the helium acceleration PDS-1000/He gun is available from Bio-Rad Laboratories. For the bombardment, immature embryos or derived target cells such as scutella or calli from immature embryos may be arranged on solid culture medium.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. Nos. 5,451,513, 5,545,818, 5,877,402, 5,932,479, and WO 99/05265.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. Nos. 5,177,010, 5,104,310, 5,004,863, 5,159,135). Further, the integration of the T-DNA is a relatively precise process resulting in few rearrangements. The region of DNA to be transferred is defined by the border sequences, and intervening DNA is usually inserted into the plant genome.

*Agrobacterium* transformation vectors are capable of replication in *E. coli* as well as *Agrobacterium*, allowing for convenient manipulations as described (Klee et al., Plant DNA Infectious Agents, Hohn and Schell, (editors), Springer-Verlag, New York, (1985): 179-203). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, Breeding Methods for Cultivar Development, J. Wilcox (editor) American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al., 1985; Toriyama et al., 1986; Abdullah et al., 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., Methods for Plant Molecular Biology, Academic Press, San Diego, (1988)). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton; soybean; *Brassica*; peanut and pea.

Methods for transformation of cereal plants such as wheat and barley for introducing genetic variation into the plant by introduction of an exogenous nucleic acid and for regeneration of plants from protoplasts or immature plant embryos are well known in the art, see for example, CA 2,092,588, AU 61781/94, AU 667939, U.S. Pat. No. 6,100,447, WO 97/048814, U.S. Pat. Nos. 5,589,617, 6,541,257, and other methods are set out in WO 99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts. The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (M. J. McPherson and S. G Moller (editors), BIOS Scientific Publishers Ltd, Oxford, (2000)). PCR can be performed on cDNA obtained from reverse transcribing mRNA isolated from plant cells expressing a polynucleotide of the invention. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al., (supra) and Sambrook et al., (supra). Sequencing can be carried out by any suitable method, for example, dideoxy sequencing, chemical sequencing or variations thereof. Direct sequencing has the advantage of determining variation in any base pair of a particular sequence.

The second step of the first method of the invention comprises growing said transformed cells under conditions allowing the expression of the oxygen-sensitive protein according to the invention. Said conditions suitable for the expression of the NifB protein according to the invention include conditions to be those that allow an optimal growth of the cells and those that allow the protein expression in said cells.

Conditions for optimizing the culture of yeast cells and the expression of said heterologous protein will depend on the promoter which regulates the expression of the heterologous gene.

Taking into account that the first and the second step of the first method of the invention are intended to express and purify an oxygen-sensitive protein, it is desirable to test if anaerobic conditions have been maintained during said protein induction and purification. The fusion protein of the invention (or the polynucleotide which codes said fusion protein) is expressed in the mitochondria wherein anaerobiosis conditions occur. Thus, any test which allows the determination of mitochondrial activity would be useful to determine the lack of oxygen stress conditions during galactose induction. If desired, aconitase enzyme activity can be measured (see for example Kennedy et al., 1983, J. Biol. Chem, 258: 11098-11105).

The expression of the fusion protein during the second step of the first method of the invention can be monitored by methods well known in the art such western blot or immunofluorescence. Virtually any conventional method can be used within the frame of the invention to detect, and if desired, to quantify the oxygen-sensitive protein. By way of a non-limiting illustration, the expression levels can be determined by means of antibodies with the capacity for binding specifically to the assayed protein (or to fragments thereof containing the antigenic determinants) and subsequent quantification of the resulting antigen-antibody complexes.

There is a wide variety of known tests that can be used according to the present invention, such as combined application of non-labeled antibodies (primary antibodies) and labeled antibodies (secondary antibodies), Western blot or immunoblot, ELISA (enzyme-linked immunosorbent assay), RIA (radioimmunoassay), competitive EIA (enzyme immunoassay), DAS-ELISA (double antibody sandwich ELISA), immunofluorescence. Other forms of detecting and quantifying protein include, for instance, affinity chromatography techniques or ligand-binding assays. Since the mitochondrial targeting signal is cleaved upon entry of the fusion protein into the mitochondria, it is also possible to monitor the accumulation of the protein in the mitochondria by detecting the accumulation of the processed fusion protein using any technique which allows detecting the change in molecular weight that occurs following removal of the mitochondrial targeting signal. In a preferred embodiment, the detection of the mature protein is carried out by western blot of whole cell protein extracts using an antibody specific against the NifB protein or against any protein tag forming part of the fusion protein.

In a preferred embodiment of the invention, the determination of the levels of the fusion proteins is performed by quantitative immunofluorescence. Immunofluorescence (IF) is a technique based on fluorescent microscopy utilized primarily for testing biological samples. This technique uses the specificity of antibodies to their antigen to target fluorescent dyes to particular biomolecule targets within a cell, thus allowing the visualization of the distribution of the target molecule through the sample. IF can be used in cultured cell lines, or individual cells, and may be used to analyze the distribution of proteins, glycans, and small biological and non-biological molecules. In addition, IF could also be used in combination with other, non-antibody methods of fluorescent staining, such as, for example, DAPI to label DNA. More than one antibody can be used at the same time in order to detect, for example more than one protein. Several microscope designs can be used for analysis of IF samples, such as the epifluorescence microscope and the confocal microscope. Various super-resolution microscope designs that are capable of much higher resolution may also be used. In a still more preferred embodiment, a double staining is carried out. In said double staining the oxygen sensitive protein of the invention can be detected as well as the specific location of said protein in the cell. For example, yeast cells transfected with the polynucleotide or with the expression vector of the invention which encodes a fusion protein comprising the NifB protein, the SU9 peptide and the GFP protein can be fixed with a solution of paraformaldehyde (2-4%) and permeabilized with 0.1% TX-100. The mitochondrial localization of NifB can be confirmed by means of specifically stain. Mitochondria stain can be carried out by techniques well known in the art. Examples of said techniques include but are not limited to rhodamine 123 staining, tetramethylrosamine or mitotracker stain. In a preferred embodiment, mitochondrial are detected by mitrotracker stain. Briefly, this technique is based in using fluorescent dyes that stain mitochondria in live cells. Specific mitotracker probes are commercially available such as rosamine mitotracker dyes which include MitoTrackerR Orange CMTMRos, a derivative of tetramethylrosamine, and MitoTrackerR Red CMXRos (Invitrogen), a derivative of X-rosamine. Reduced MitoTrackerR dyes, MitoTrackerR Orange CM-H2TMRos and MitoTrackerR Red CM-H2XRos (Cat. no. M7513), which are derivatives of dihydrotetramethyl rosamine and dihydro-X-rosamine (Invitrogen). These reduced probes do not fluoresce until they enter live cells, where they are oxidized to the corresponding fluorescent mitochondrion-selective probe and then sequestered in the mitochondria.

If desired, the first method of the invention comprises an additional step which comprises the purification of said oxygen sensitive protein. In order to preserve the activity of the fusion protein, it is recommended that the purification is carried out under anaerobic conditions. As used herein, the term "anaerobic conditions" refers to conditions wherein the oxygen concentration is below 1 ppm. In a preferred embodiment, said oxygen sensitive protein is NifB from *A. vinelandii*.

The purification of the oxygen-sensitive protein requires that the cells in which the protein is expressed are lysed. The skilled person will understand that the purification can be carried out by applying a single lysis step so that all biological membranes are disrupted, including the cell membrane and the mitochondrial membranes, thereby obtaining a whole cell lysate which can then be further processed in order to purify the oxygen-sensitive protein. Alternatively, the purification may be carried out in isolated mitochondria, which are first obtained from cells by a first lysis step aimed at lysing the cell membrane and, as the case may be, the cell wall. The isolated mitochondrial are then lysed in order to obtain a mitochondrial lysate from which the oxygen-sensitive is purified.

If desired, the NifB producing *S. cerevisiae* cells are first lysed under anaerobic conditions in order to isolate said protein. Cells can be resuspended in anaerobic lysis buffer containing: 50 mM sodium phosphate pH 8.0, 0.5 M NaCl, 10 mM imidazole, 1 mM phenylmethylsulfonyl fluoride (PMSF), 1 mM leupeptin, 2 mM sodium dithionite (DTH), 5 µg/ml DNaseI and preferably, any protease inhibitor in order to evoke protein degradation. Cells can be lysed in a French Press cell at 1500 lb/in2. Cell-free extracts obtained after removing debris can be obtained by centrifugation at 17,000 rpm for 1 hour at 4° C. under anaerobic conditions.

In order to isolate and purify the NifB protein according to the invention, any technique known in the art for protein purification under anaerobic conditions can be used (see for example, Curatti et al., 2006, Proc. Natl. Acad. Sci. USA, 103: 5297-5301; Christiansen et al. 1998, Biochemistry 37:12611-12623). In one embodiment, the fusion protein according to the invention is isolated using antibodies which are capable of specifically binding to either the oxygen-sensitive protein or, as the case may be, to the purification tag. Antibodies suitable for the immuno-isolation of the fusion protein include, without limitation, monoclonal antibodies, polyclonal antibodies or fragment thereof, Fv, Fab, Fab' and F(ab')2, scFv, diabodies, triabodies, tetrabodies and humanized antibodies.

In a preferred embodiment, in those embodiments wherein the fusion protein further comprises a tag, purification of the NifB protein is carried out by affinity chromatography using a reagent which specifically binds to said tag. In this case, the tag in the fusion protein and the reagent showing affinity for said tag act as first and second members of a binding pair, respectively.

The term "first member of a binding pair", as used herein, refers to a molecule which has affinity for and "binds" to another (hereinafter known as "second member of the binding pair") under certain conditions, referred to as "binding conditions". The first member of the binding pair is a peptide (protein) whereas the second member of the binding pair may be a of peptide or non-peptide nature.

The term "binding pair" does not involve any particular size or any other technical structural characteristic other than that said binding pair can interact and bind to the other member of the binding pair resulting in a conjugate wherein the first and second components are bound to each other by means of the specific interaction between the first and second member of a binding pair. The binding pair includes any type of immune interaction such as antigen/antibody, antigen/antibody fragment, hapten/anti-hapten as well as non-immune interactions such as avidin/biotin, avidin/biotinylated molecules, folic acid/folate-binding protein, hormone/hormone receptor, lectin/carbohydrate, lectin/molecule modified with carbohydrates, enzyme/enzyme substrate, enzyme/enzyme inhibitor, protein A/antibody, protein G/antibody, complementary nucleic acids (including sequences of DNA, RNA and peptide nucleic acids (PNA)), polynucleotide/polynucleotide-binding protein and the like.

As used in the present invention, the expression "specific binding" refers to the capacity of a first molecule to bind specifically to a second molecule by means of the existence of complementarity between the three-dimensional structures of the two molecules with a substantially higher affinity for non-specific binding such that the binding between said first and second molecule preferably takes place before the binding of any of said molecules with respect to the other molecules present in the reaction mixture. It is understood that there is high affinity in the binding of two molecules when the complex resulting from said binding has a dissociation constant (KD) of less than 10-6 M, less than 10-7 M, less than 10-8 M, less than 10-9 M, less than 10-10 M, less than 10-11 M, less than 10-12 M, less than 10-13 M, less than 10-14 M or less than 10-15 M.

In an embodiment, NifB protein is expressed as fusion comprising a histidine tag, in which case the purification can be carried out using immobilized metal affinity chromatography (IMAC) This technique works by allowing proteins with affinity for metal ions (i.e. fusion protein comprising NifB fused to a histidine tag) to be retained in a column containing immobilized metal ions, such as cobalt, for the purification of histidine containing proteins or peptides. Eluted fractions can be then concentrated using a Vivaspin 500 concentrator (Sartorius) with cut-off pore size of 30 kDa as is shown in Example 3 of the present application.

Methods for expression of one or more nitrogenase components in plant cells are also contemplated. Such methods may comprise introducing a recombinant DNA construct as described above into a plant cell nucleus or chloroplast, and growing the plant cell in an environment resulting in expression of the one or more nitrogenase components. Manipulation of light intensity, day length, temperature, levels of available nutrients, and atmospheric oxygen content may facilitate nitrogenase activity.

The method may further comprise assaying for the presence of an introduced nifB gene in the genome of a plant cell, and/or the presence of a NifB protein in the cell. Thus, well known methods such as Southern blotting and western blotting may be used (Sambrook et al., 1989). The method may further comprise assaying for nitrogenase activity, including dinitrogenase-reductase and/or dinitrogenase activity (e.g. Stewart et al., PNAS 58:2071, 1967). The presence of an introduced nif gene may be transient, or the gene may be stably integrated into a nuclear or chloroplastic cell genome. Activity of nitrogenase or its components may thus be expressed in a transient or stable manner, and may occur in the plant cell nucleus, cytoplasm, mitochondria, or chloroplasts.

Measurement of nitrogenase activity, dinitrogenase activity, and/or dinitrogenase reductase activity may be performed for instance by an acetylene reduction assay (Stewart, PNAS 58:2071, 1967), or other assay known in the art such as by measuring ammonia production, or $N_2$ isotope incorporation, or by production of hydrogen gas ($H2$). Measurement may further comprise use of whole plants or plant cells, as well as partially isolated organelles and other cell fractions (e.g. Millar et al., Methods Cell Biol. 80:65-90, 2007). The oxygen content of the atmosphere in which the plants or plant cells are grown may also be manipulated to facilitate measurement of nitrogenase activity.

The purification of the protein NifB expressed in a eukaryotic cell may be performed by conventional means know in the art. In a preferred embodiment, the purification is performed at a pH between 5 and 9, between 6 and 8, between 7 and 8 or between 8 and 9 and a temperature between 30° C. and 70° C., between 35° C. and 65° C., most preferably between 40° C. and 65° C.

In a preferred embodiment the purification is performed at pH between 7 and 8 and temperature between 55 and 65° C.

In another aspect the invention relates to a protein obtained by the first method of the invention.

In a particular embodiment the isolated NifB protein has at least 3 Fe atoms per monomer of protein, at least 4 Fe atoms per monomer of protein, at least 5 Fe atoms per monomer of protein, most preferably the isolated protein as at least 6 Fe atoms per monomer of protein, at least 7 Fe atoms per monomer of protein, at least 8 Fe atoms per monomer of protein, at least 9 Fe atoms per monomer of protein, at least 10 Fe atoms per monomer of protein, at least 11 fe atoms per monomer of protein and at least 12 Fe atoms per monomer of protein.

Further Polynucleotides of the Invention

In further aspects the invention relates to polynucleotides encoding fusion proteins selected from the group consisting of NifU, NifS or FdxN proteins and a mitochondrial targeting peptide.

Many of the terms related to the second polynucleotide of the invention have been already defined in the context of the first polynucleotide of the invention.

A NifU polypeptide in naturally occurring bacteria is a molecular scaffold polypeptide involved in iron-sulfur (FeS) cluster biosynthesis for nitrogenase components. As used herein, a "NifU polypeptide" or "NifU protein" means a polypeptide comprising the domain TIGR02000. Members of the TIGR02000 domain protein family are specifically involved in nitrogenase maturation. NifU comprises an N-terminal domain (pfam01592) and a C-terminal domain (pfam01106). Three different but partially homologous Fe—S cluster assembly systems have been described: Isc, Suf, and Nif. The Nif system, of which NifU is a part, is associated with donation of an Fe—S cluster to nitrogenase in a number of nitrogen-fixing species. NifU, therefore, is specific for NifU polypeptides involved in nitrogenase maturation. Members of the related TIGR01999 domain protein family which are IscU proteins (from for example, *Escherichia, coli* and *Saccharomyces cerevisiae* and *Homo sapiens*) that comprise a homolog of the N-terminal region of NifU are also excluded from the definition of NifU herein. A naturally occurring NifU polypeptide typically has a length of between 260 and 310 amino acids and the natural monomer has a molecular weight of about 29 kDa. A great number of NifU polypeptides have been identified and numerous sequences are available in publically available databases. For example, NifU polypeptides have been reported from *Klebsiella michiganensis* (Accession No. WP 049136164.1), *Klebsiella variicola* (WP_050887862.1), *Dickeya solani* (WP_057084657.1), *Brenneria goodwinii* (WP_048638833.1), *Tolumonas auensis* (WP_012728889.1), *Agarivorans gilvus* (WP_055731596.1), *Desulfocurvus vexinensis* (WP_028587630.1), *Rhodopseudomonas palustris* (WP_044417303.1), *Helicobacter pylori* (WP_001051984.1) and *Sulfurovum* sp. PC08-66 (KFM05011.1). As used herein, a "functional NifU polypeptide" is a NifU polypeptide which is capable of functioning as a molecular scaffold polypeptide involved in iron-sulfur (FeS) cluster biosynthesis.

A NifS polypeptide in naturally occurring bacteria is a cysteine desulfurase involved in iron-sulfur (FeS) cluster biosynthesis e.g. which is involved in mobilisation of sulfur for Fe—S cluster synthesis and repair. As used herein, a "NifS polypeptide" or "NifS protein" means (i) a polypeptide comprising one or both of the conserved domains TIGR03402 and COG1104. The TIGR03402 domain protein family includes a clade nearly always found in extended nitrogen fixation systems plus a second clade more closely related to the first than to IscS and also part of NifS-like/NifU-like systems. The TIGR03402 domain protein family does not extend to a more distant clade found in the epsilon proteobacteria such as *Helicobacter pylori*, also named NifS in the literature, built instead in TIGR03403. The COG1104 domain protein family includes cysteine sulfinate desulfinase/cysteine desulfurase or related enzymes. Some NifS polypeptides include the asparate aminotransferase domain cl 18945. A naturally occurring NifS polypeptide typically has a length of between 370 and 440 amino acids and the natural monomer has a molecular weight of about 43 kDa. A great number of NifS polypeptides have been identified and numerous sequences are available in publically available databases. For example, NifS polypeptides have been reported from *Klebsiella michiganensis* (Accession No. WP_004138780.1), *Raoultella terrigena* (WP 045858151.1), *Kluyvera intermedia* (WP_047370265.1), *Rahnella aquatilis* (WP_014333911.1), *Agarivorans gilvus* (WP_055731597.1), *Azospirillum brasilense* (WP_014239770.1), *Desulfosarcina cetonica* (WP_054691765.1), *Clostridium intestinale* (WP_021802294.1), *Clostridiisalibacter paucivorans* (WP_026894054.1) and *Bacillus coagulans* (WP_061575621.1). As used herein, a "functional NifS polypeptide" is a NifS polypeptide which is capable of functioning in iron-sulfur (FeS) cluster biosynthesis and/or repair.

FdxN makes reference to a class of 2 [4Fe-4S] cluster ferredoxins. This class of ferredoxins presents two conserved motifs, Cys-X2-Cys-X2-Cys-X3-Cys (SEQ ID NO: 34) and Cys-X2-Cys-X79-Cys-X3-Cys-X35-Cys (SEQ ID NO: 35), which are also conserved in FdxN (except for the last Cys residue).

In a particular embodiment all three proteins or two of them are encoded by the same polynucleotide. In a further embodiment, each of NifU, NifS and FdxN proteins are encoded by a different polynucleotide. In a further embodiment the second polynucleotide of the invention may additionally encode other proteins such as NifB.

The mitochondrial targeting peptide may be N-terminal or C-terminal to each of the NifU, NifS and FdxN proteins. In a preferred embodiment the mitochondrial peptide target in N-terminal to each of NifU, NifS and FdxN proteins.

Suitable mitochondrial peptide tags have been described in the context of the first polynucleotide of the invention.

In a particular embodiment the second polynucleotide of the invention further comprises a peptide tag. Suitable peptide tags have been described in the context of the first polynucleotide of the invention. Additional peptide tags include without limitation Glutathione S-Transferase tag-Maltose Binding Protein, Calmodulin Binding Peptide, Intein-Chitin Binding Domain tag, FLAG epitope tag and c-Myc epitope tag.

In a preferred embodiment, the second polynucleotide of the invention encodes a fusion protein that comprises, in the N- to C-terminal order, an N-terminal mitochondrial targeting peptide, the detection/purification tag and any of the NifU, NifS and FdxN proteins. In other embodiment, the polynucleotide of the invention encodes a fusion protein that comprises, in the N- to C-terminal order, an N-terminal mitochondrial targeting peptide, any of NifU, NifS and FdxN proteins and the detection/purification tag.

In a preferred embodiment, the mitochondrial targeting peptide is formed by the first 69 amino acids of subunit 9 of the $F_0$ ATPase of *Neurospora crassa* (SU9) (SEQ ID NO:1).

In another preferred embodiment, the mitochondrial targeting peptide is formed by the first 29 amino acids of the yeast cytochrome c oxidase IV (COX4) protein (SEQ ID NO: 2).

In a preferred embodiment, the mitochondrial targeting peptide is formed by a functionally equivalent variant of the sequences SEQ ID NO: 1 or 2

In a preferred embodiment, the polynucleotide of the invention is operatively linked to suitable transcriptional or translational regulatory elements as those defined in the context of the first polynucleotide of the invention.

In a particular embodiment proteins NifU, NifS and FdxN are from a prokaryotic organism.

In a preferred embodiment the prokaryotic organism is *Azotobacter vinelandii*.

In another embodiment the second polynucleotide of the invention is codon optimized for expression in yeast or plants. The optimization process has already been described in the context of the first polynucleotide of the invention.

In a preferred embodiment the optimization is for expression in *Saccharomyces cerevisiae* or *Nicotiana benthamiana*.

A suitable nucleic acid (SEQ ID NO: 28) for expressing NifS comprises a nucleic acid encoding the SU9 mitochondrial targeting signal (underlined) and a yeast optimized nucleic acid sequence encoding *A. vinelandii* NifS (bold). The sequence shown below the nucleic acid sequence is the translated amino acid sequence (SEQ ID NO: 29).

The sequence is shown below:

```
SU9-NifS
ATGGCCTCCACTCGTGTCCTCGCCTCTCGCCTGGCCTCCCAGATGGCTGCTTCCGCCAAG
 M   A   S   T   R   V   L   A   S   R   L   A   S   Q   M   A   A   S   A   K

GTTGCCCGCCCTGCTGTCCGCGTTGCTCAGGTCAGCAAGCGCACCATCCAGACTGGCTCC
 V   A   R   P   A   V   R   V   A   Q   V   S   K   R   T   I   Q   T   G   S

CCCCTCCAGACCCTCAAGCGCACCCAGATGACCTCCATCGTCAACGCCACCACCCGCCAG
 P   L   Q   T   L   K   R   T   Q   M   T   S   I   V   N   A   T   T   R   Q

GCTTTCCAGAAGCGCGCCTACTCTTCCGCAGCCATGGCCGACGTTTACTTGGATAATAAC
 A   F   Q   K   R   A   Y   S   S   A   A   M   A   D   V   Y   L   D   N   N

GCTACTACAAGAGTCGATGACGAAATAGTACAAGCTATGTTGCCATTTTTCACAGAACAA
 A   T   T   R   V   D   D   E   I   V   Q   A   M   L   P   F   F   T   E   Q

TTCGGTAACCCTTCCAGTTTGCATTCCTTCGGTAACCAAGTTGGTATGGCCTTGAAGAAA
 F   G   N   P   S   S   L   H   S   F   G   N   Q   V   G   M   A   L   K   K

GCTAGACAATCTGTCCAAAAATTGTTAGGTGCAGAACACGATTCCGAAATCGTTTTTACC
 A   R   Q   S   V   Q   K   L   L   G   A   E   H   D   S   E   I   V   F   T

AGTTGTGGTACTGAATCTGACTCAACCGCCATTTTGTCTGCCTTAAAAGCTCAACCAGAA
 S   C   G   T   E   S   D   S   T   A   I   L   S   A   L   K   A   Q   P   E

AGAAAGACTGTCATAACCACTGTTGTCGAACATCCTGCAGTATTGTCTTTATGCGATTAT
 R   K   T   V   I   T   T   V   V   E   H   P   A   V   L   S   L   C   D   Y

TTGGCCTCAGAAGGTTACACTGTTCATAAGTTACCAGTCGATAAAAAGGGTAGATTGGAC
 L   A   S   E   G   Y   T   V   H   K   L   P   V   D   K   K   G   R   L   D

TTAGAACACTATGCTTCCTTGTTAACAGATGACGTAGCTGTAGTTAGTGTTATGTGGGCA
 L   E   H   Y   A   S   L   L   T   D   D   V   A   V   V   S   V   M   W   A

AATAACGAAACTGGTACATTGTTTCCAATTGAAGAAATGGCAAGATTAGCCGATGACGCT
 N   N   E   T   G   T   L   F   P   I   E   E   M   A   R   L   A   D   D   A

GGTATAATGTTCCATACTGATGCAGTACAAGCCGTTGGTAAAGTCCCTATAGACTTGAAG
 G   I   M   F   H   T   D   A   V   Q   A   V   G   K   V   P   I   D   L   K

AACTCGTCAATCCACATGTTGTCCTTAAGTGGTCATAAAATTGCACGCTCCAAAGGGTGTT
 N   S   S   I   H   M   L   S   L   S   G   H   K   L   H   A   P   K   G   V

GGTGTCTTGTACTTAAGAAGAGGTACAAGATTCAGACCTTTGTTAAGAGGTGGTCATCAA
 G   V   L   Y   L   R   R   G   T   R   F   R   P   L   L   R   G   G   H   Q

GAAAGAGGTAGAAGAGCCGGTACTGAAAATGCTGCATCTATTATAGGTTTGGGTGTTGCC
 E   R   G   R   R   A   G   T   E   N   A   A   S   I   I   G   L   G   V   A

GCTGAAAGAGCTTTACAATTCATGGAACATGAAAACACTGAAGTTAAGAGATTGCGTGAT
 A   E   R   A   L   Q   F   M   E   H   E   N   T   E   V   K   R   L   R   D

AAGTTAGAAGCAGGTATTTTGGCCGTCGTACCACACGCATTTGTTACTGGTGACCCAGAC
 K   L   E   A   G   I   L   A   V   V   P   H   A   F   V   T   G   D   P   D

AATAGATTACCTAACACAGCTAACATCGCATTCGAATACATCGAAGGTGAAGCTATCTTG
 N   R   L   P   N   T   A   N   I   A   F   E   Y   I   E   G   E   A   I   L

TTGTTGTTGAACAAAGTTGGTATAGCAGCCTCCAGTGGTTCTGCTTGTACATCTGGTTCA
 L   L   L   N   K   V   G   I   A   A   S   S   G   S   A   C   T   S   G   S

TTGGAACCATCACATGTTATGAGAGCAATGGATATTCCTTATACAGCTGCACACGGTACT
 L   E   P   S   H   V   M   R   A   M   D   I   P   Y   T   A   A   H   G   T

GTTAGATTTTCTTTGAGTAGATACACAACCGAAGAAGAAATTGATAGAGTCATTAGAGAA
 V   R   F   S   L   S   R   Y   T   T   E   E   E   I   D   R   V   I   R   E

GTACCACCTATTGTTGCTCAATTGAGAAAATTGTCTCCTTACTGGTCAGGTAATGGTCCT
 V   P   P   I   V   A   Q   L   R   K   L   S   P   Y   W   S   G   N   G   P

GTTGAAGACCCTGGTAAAGCCTTTGCTCCTGTCTATGGTTGA
 V   E   D   P   G   K   A   F   A   P   V   Y   G   -
```

A suitable nucleic acid (SEQ ID NO: 30) for expressing FdxN comprises a nucleic acid encoding the SU9 mitochondrial targeting signal (underlined) and a yeast optimized nucleic acid sequence encoding *A. vinelandii* FdxN (bold). The sequence shown under the nucleic acid sequence is the translated amino acid sequence (SEQ ID NO: 31).

The sequence is shown below:

```
SU9-FdxN
ATGGCCTCCACTCGTGTCCTCGCCTCTCGCCTGGCCTCCCAGATGGCTGCTTCCGCCAAG
 M   A   S   T   R   V   L   A   S   R   L   A   S   Q   M   A   A   S   A   K

GTTGCCCGCCCTGCTGTCCGCGTTGCTCAGGTCAGCAAGCGCACCATCCAGACTGGCTCC
 V   A   R   P   A   V   R   V   A   Q   V   S   K   R   T   I   Q   T   G   S

CCCCTCCAGACCCTCAAGCGCACCCAGATGACCTCCATCGTCAACGCCACCACCCGCCAG
 P   L   Q   T   L   K   R   T   Q   M   T   S   I   V   N   A   T   T   R   Q

GCTTTCCAGAAGCGCGCCTACTCTTCCATGGCTCTTAAGATAGTTGAGTCTTGTGTGAAC
 A   F   Q   K   R   A   Y   S   S   M   A   L   K   I   V   E   S   C   V   N

TGCTGGGCATGTGTTGATGTGTGCCCAAGTGAGGCTATATCCTTGGCAGGTCCTCATTTT
 C   W   A   C   V   D   V   C   P   S   E   A   I   S   L   A   G   P   H   F

GAAATTTCTGCTTCAAAATGCACCGAGTGTGATGGAGACTATGCTGAAAAGCAATGCGCA
 E   I   S   A   S   K   C   T   E   C   D   G   D   Y   A   E   K   Q   C   A

TCTATTTGTCCAGTTGAAGGTGCTATCTTGTTAGCAGACGGAACTCCTGCTAACCCACCT
 S   I   C   P   V   E   G   A   I   L   L   A   D   G   T   P   A   N   P   P

GGTTCACTTACAGGAATCCCACCTGAAAGATTGGCTGAGGCAATGAGAGAAATACAGGCA
 G   S   L   T   G   I   P   P   E   R   L   A   E   A   M   R   E   I   Q   A

AGGTAA
 R   -
```

Another suitable nucleic acid (SEQ ID NO: 32) for expressing FdxN comprises a nucleic acid encoding the SU9 mitochondrial targeting signal (underlined), a yeast optimized nucleic acid sequence encoding *A. vinelandii* FdxN (bold) and the HA tag (bold and underlined). The sequence shown below the nucleic acid sequence is the translated amino acid sequence (SEQ ID NO: 33).

The sequence is shown below:

```
SU9-FdxN-HA
ATGGCCTCCACTCGTGTCCTCGCCTCTCGCCTGGCCTCCCAGATGGCTGCTTCCGCCAAG
 M   A   S   T   R   V   L   A   S   R   L   A   S   Q   M   A   A   S   A   K

GTTGCCCGCCCTGCTGTCCGCGTTGCTCAGGTCAGCAAGCGCACCATCCAGACTGGCTCC
 V   A   R   P   A   V   R   V   A   Q   V   S   K   R   T   I   Q   T   G   S

CCCCTCCAGACCCTCAAGCGCACCCAGATGACCTCCATCGTCAACGCCACCACCCGCCAG
 P   L   Q   T   L   K   R   T   Q   M   T   S   I   V   N   A   T   T   R   Q

GCTTTCCAGAAGCGCGCCTACTCTTCCATGGCTCTTAAGATAGTTGAGTCTTGTGTGAAC
 A   F   Q   K   R   A   Y   S   S   M   A   L   K   I   V   E   S   C   V   N

TGCTGGGCATGTGTTGATGTGTGCCCAAGTGAGGCTATATCCTTGGCAGGTCCTCATTTT
 C   W   A   C   V   D   V   C   P   S   E   A   I   S   L   A   G   P   H   F

GAAATTTCTGCTTCAAAATGCACCGAGTGTGATGGAGACTATGCTGAAAAGCAATGCGCA
 E   I   S   A   S   K   C   T   E   C   D   G   D   Y   A   E   K   Q   C   A

TCTATTTGTCCAGTTGAAGGTGCTATCTTGTTAGCAGACGGAACTCCTGCTAACCCACCT
 S   I   C   P   V   E   G   A   I   L   L   A   D   G   T   P   A   N   P   P

GGTTCACTTACAGGAATCCCACCTGAAAGATTGGCTGAGGCAATGAGAGAAATACAGGCA
 G   S   L   T   G   I   P   P   E   R   L   A   E   A   M   R   E   I   Q   A

AGGTATCCATATGATGTTCCAGATTATGCTTAA
 R   Y   P   Y   D   V   P   D   Y   A   -
```

In another aspect the invention relates to a second expression vector comprising the second polynucleotide of the invention.

In a further aspect the invention relates to a second eukaryotic cell comprising the second polynucleotide/s or the second vector/s of the invention Vectors and cells suitable for the realization of the second vector of the invention or the cells comprising the second polynucleotide or the second vector of the invention have already been described in the context of the paragraphs related to expression vectors and cells of the invention.

In a preferred embodiment the second eukaryotic of the invention comprises at least one copy of a polynucleotide or expression vector encoding each of the proteins NifU, NifS and FdxN.

In another embodiment the second eukaryotic cell additionally comprises the first polynucleotide or the first vector of the invention.

In a further embodiment the second eukaryotic cell grows under aerobic conditions. The characteristics of the aerobic growing of the cells have been already described above.

Method for Expressing in Eukaryotic Cells the Further Polypeptides of the Invention In another aspect the invention relates to a method for expressing NifU, NifS or FdxN proteins in a eukaryotic cell comprising the steps of:
  i) introducing into said cell a polynucleotide as defined under the heading "further polynucleotides of the invention",
  ii) growing said cell under conditions allowing the expression of said protein and, if desired,
  iii) purifying said protein under anaerobic conditions.

Details for the realization of the second method of the invention have been described within the context of the first method of the invention and are equally applicable to the expression of polypeptides expressing NifU, NifS or FdxN.

In a further aspect the invention relates to a NifU, NifS or FdxN protein obtained by the second method of the invention.

Methods for the In Vitro Synthesis FeMo—Co According to the Invention

In another aspect the invention relates to a method for in vitro synthesis of FeMo-co using NifB using purified components comprising the steps of:
  i) mixing NifB, apo-NifEN, NifH proteins with SAM or SAM generating system, molybdate or a molybdenum donating protein, R-homocitrate or a R-homocitrate generating system, a reducing agent, an ATP regenerating system and Mg-ATP, and, if desired, one or more of NifX, $Fe^{2+}$, and $S^{2-}$,
  ii) incubating the mixture defined in (i) under conditions allowing the synthesis of FeMo-co.

In another aspect, the invention relates to a method for the in vitro synthesis of FeMo-co comprising the steps of:
  i) introducing into a cell a polynucleotide a polynucleotide encoding a fusion protein comprising NifB protein and a mitochondrial targeting peptide,
  ii) growing said cell under conditions allowing the expression of said NifB protein,
  iii) purifying said protein under anaerobic conditions,
  iv) mixing the NifB protein obtained in step iii), apo-NifEN, NifH proteins with SAM or SAM generating system, molybdate or a molybdenum donating protein, R-homocitrate or a R-homocitrate generating system, a reducing agent, an ATP regenerating system and Mg-ATP, and, if desired, one or more of NifX, $Fe^{2+}$, and $S^{2-}$, and
  v) incubating the mixture defined in (i) under conditions allowing the synthesis of FeMo-co.

"FeMo-co" (FeMo cofactor) refers to the primary cofactor of nitrogenase. Nitrogenase is the enzyme that catalyzes the conversion of atmospheric $N_2$ into ammonia ($NH_3$) through the process known as nitrogen fixation. Containing iron and molybdenum, the cofactor is called FeMoco. The FeMo cofactor is a cluster with composition $Fe_7MoS_9C$.

This large cluster can be viewed as two subunits composed of one $Fe_4S_3$ cluster and one $MoFe_3S_3$ cluster. The two clusters are linked by three sulfide ligands.

The NifEN complex is a scaffold complex that is required for the correct assembly of dinitrogenase and is also structurally similar to the dinitrogenase. The NifEN complex is comprised of 2 subunits of each of NifE and NifN, respectively, forming a heterotetramer, here termed $ENa_2B_2$. A NifE polypeptide in naturally occurring bacteria is a polypeptide which is the a subunit of the $ENa_2B_2$ tetramer with the NifN polypeptide, and this $ENa_2B_2$ tetramer is required for FeMo—Co synthesis and is proposed to function as a scaffold on which FeMo—Co is synthesized.

As used herein, a "NifE polypeptide" or "NifE protein" means a polypeptide which comprises one or both of the domains TIGR01283 and PRK14478. Members of TIGR01283 domain protein family are also members of the superfamily cl02775. A naturally occurring NifE polypeptide typically has a length of between 440 and 490 amino acids and the natural monomer has a molecular weight of about 50 kDa. A great number of NifE polypeptides have been identified and numerous sequences are available in publically available databases. For example, NifE polypeptides have been reported from *Klebsiella michiganensis* (Accession No. WP 049114606.1), *Klebsiella variicola* (SBM87755.1), *Dickeya paradisiaca* (WP_012764127.1), *Tolumonas auensis* (WP_012728883.1), *Pseudomonas stutzeri* (WP_003297989.1), *Azotobacter vinelandii* (WP_012698965.1), *Trichormus azollae* (WP_013190624.1), *Paenibacillus durus* (WP_025698318.1), *Sulfuricurvum kujiense* (WP_013460149.1), *Methanobacterium formicicum* (AIS31022.11), *Anaeromusa acidaminophila* (WP_018701501.11) and *Megasphaera cerevisiae* (WP_048514099.1). As used herein, a "functional NifE polypeptide" is a NifE polypeptide which is capable of forming a functional tetramer together with NifN such that the complex is capable of synthesizing FeMo—Co.

A NifH polypeptide in naturally occurring bacteria is a structural component of nitrogenase complex and is often termed the iron (Fe) protein. It forms a homodimer, with a $Fe_4S_4$ cluster bound between the subunits and two ATP-binding domains. NifH is the obligate electron donor to the MoFe protein (NifD/NifK heterotetramer) and therefore functions as the nitrogenase reductase (EC 1.18.6.1). NifH is also involved in FeMo—Co biosynthesis and apo-MoFe protein maturation. As used herein, a "NifH polypeptide" or "NifH protein" means a polypeptide comprising one or more of the domains TIGR01287, PRK13236, PRK13233 and cd02040. The TIGR01287 domain is present in each of molybdenum-iron nitrogenase reductase (NifH), vanadium-iron nitrogenase reductase (VnfH), and iron-iron nitrogenase reductase (AnfH) but excludes the homologous protein from the light-independent protochlorophyllide reductase. A naturally occurring NifH polypeptide typically has a length of between 260 and 300 amino acids and the natural monomer has a molecular weight of about 30 kDa. A great number of NifH polypeptides have been identified and numerous sequences are available in publically available databases. For example, NifH polypeptides have been reported from *Klebsiella michiganensis* (Accession No.

WP_049123239.1), Brenneria goodwinii (WP_048638817.1), Sideroxydans lithotrophicus (WP_013029017.1), Denitrovibrio acetiphilus (WP_013010353.1), Desulfovibrio africanus (WP_014258951.1), Chlorobium phaeobacteroides (WP_011744626.11), Methanosaeta concilii (WP_013718497.1), Rhodobacter (WP_009565928.11), *Methanocaldococcus infernus* (WP_013099472.1) and *Desulfosporosinus youngiae* (WP_007781874.11).

As used herein, a functional NifH polypeptide is a NifH polypeptide which is capable of forming a functional nitrogenase protein complex together with the other required subunits, for example, NifD and NifK, and the FeMo or other cofactor.

The term "SAM" refers to S-adenosylmethionine synthetase (EC 2.5.1.6) (also known as methionine adenosyltransferase (MAT)), SAM is an enzyme that creates S-adenosylmethionine (a.k.a. AdoMet, SAM or SAMe) by reacting methionine (a non-polar amino acid) and ATP (the basic currency of energy). Within the context of the third method of the invention the activity of the S-adenosylmethionine synthetase could be replaced by a SAM syntethase, methionine and ATP.

The molibdate is a compound containing an oxoanion with molybdenum in its highest oxidation state of 6. Molybdenum can form a very large range of such oxoanions which can be discrete structures or polymeric extended structures, although the latter are only found in the solid state. The larger oxoanions are members of group of compounds termed polyoxometalates, and because they contain only one type of metal atom are often called isopolymetalates.

Molybdenum donating protein refer to proteins with the capacity donate molibdate to the reaction mixture. Suitable molybdenum donating proteins include without limitation the protein NifQ protein or MoSto protein (Molybdenum Storage Protein). MoSto protein is related to the Mo-dependent nitrogenase: it supplies the nitrogenase cofactor with Mo to ensure nitrogenase functionality under molybdenum-deficient conditions.

The NifQ polypeptide or protein makes reference to a polypeptide involved in FeMo—Co synthesis.

R-homocitric acid or R homocitrate refer to organic compound with the formula HOC(CO$_2$H)(CH$_2$CO$_2$H)(C$_2$H$_4$CO$_2$H) which occurs naturally as a component of the iron-molybdenum cofactor of certain nitrogenase proteins. R-homocitrate may be replaced in the reaction by a R-homocitrate generating system comprised of homocitrate synthase, acetyl-CoA, and 2-oxoglutarate.

A NifX polypeptide in naturally occurring bacteria is a polypeptide which is involved in FeMo—Co synthesis, at least assisting in transferring FeMo—Co precursors from NifB to NifE-NifN. As used herein, a "NifX polypeptide" or "NifX protein" means a polypeptide c which comprises one or both of the conserved domains TIGR02663 and cd00853. NifX is included in a larger family of iron-molybdenum cluster-binding proteins that includes NifB and NifY, in that NifX, NafY and the C-terminal region of NifB all comprise the pfam02579 domain, and each are involved in the synthesis of FeMo—Co. Therefore, some NifX polypeptides have been annotated in databases as NifY, and vice versa. A naturally occurring NifX polypeptide typically has a length of between 110 and 160 amino acids and the natural monomer has a molecular weight of about 15 kDa. A great number of NifX polypeptides have been identified and numerous sequences are available in publically available databases. For example, NifX polypeptides have been reported from *Klebsiella michiganensis* (Accession No. WP 049070199.1), *Klebsiella oxytoca* (WP_064342937.1), *Raoultella ornithinolytica* (WP_044347173.1), *Klebsiella variicola* (WP_044612922.1), *Kosakonia radicincitans* (WP_043953583.1), *Dickeya chrysanthemi* (WP 039999416.1), *Rahnella aquatilis* (WP_047608097.1), *Azotobacter chroococcum* (WP_039800848.1), *Beggiatoa leptomitiform* is (WP_062149047.11) and *Methyloversatilis discipulorum* (WP_020165972.1). As used herein, a "functional NifX polypeptide" is a NifX polypeptide which is capable of transferring FeMo—Co precursors from NifB to NifE-NifN.

ATP regenerating systems and reducing agents are those known in the art.

The methods defined above require a step wherein the mixture is incubated under conditions allowing the synthesis of FeMo-co. The conditions will be evident to a person skilled in the art and could be easily identified by routine experimentation. By way of an example, the step wherein the mixture is incubated under conditions allowing the synthesis of FeMo-co is carried out in an N$_2$ atmosphere or in an Argon (Ar), at a temperature of between 10 and 40°, preferably at about 30° C. and during 5 min to 1 h, preferably for about 30 or 34 min.

In another aspect the invention relates to a method for in vitro synthesis of FeMo-co using cell-free extracts from strains carrying a deleted or inactivated Nifb gene comprising the steps of:
  i) Mixing NifB with a cell-free-extract from an *Azotobacter vinelandii* strain carrying a disrupted nifB gene, R-homocitrate or R-homocitrate generating system, molybdate or molybdenum donating protein, a reducing agent, an ATP regenerating system and ATP, and, if desired, NifH, SAM or SAM generating system, Fe$^{2+}$, and S$^{2-}$ and
  ii) incubating the mixture defined in (i) under conditions allowing the synthesis of FeMo-co.

In another aspect, the invention also comprises a method for in vitro synthesis of FeMo-co using NifB using cell-free extracts from strains carrying a deleted or inactivated Nifb gene comprising the steps of:
  i) introducing into a cell a polynucleotide a polynucleotide encoding a fusion protein comprising NifB protein and a mitochondrial targeting peptide,
  ii) growing said cell under conditions allowing the expression of said NifB protein,
  iii) purifying said NifB protein under anaerobic conditions,
  iv) mixing NifB obtained in step (iii) with a cell-free-extract from an *Azotobacter vinelandii* strain carrying an inactive or deleted nifB gene, R-homocitrate or R-homocitrate generating system, molybdate or molybdenum donating protein, a reducing agent, an ATP regenerating system and ATP, and, if desired, Nif H, SAM or SAM generating system, Fe$^{2+}$, and S$^{2-}$ and
  v) incubating the mixture defined in (i) under conditions allowing the synthesis of FeMo-co.

Most of the components of the fourth method of the invention have been described in the context of the third method of the invention.

Methods and conditions for growing *A. vinelandii* are well known in the art. Cells can be grown on limiting concentration of NH$^{4+}$ (100 µg as ammonium acetate) at 30° C. *A. vinelandii* is derepressed for nitrogenase in medium free of nitrogen source. Cells can be harvested at 2 hours after exhaustion of the ammonium. Once, the nitrogenase complex has been derepressed, said NifDK complex form *A. vinelandii* can be purified under anaerobic conditions by means of techniques well known in the skill in the art (Christiansen et al. 1998, Biochemistry 37:12611-12623). NifDK can be purified from cell-free extracts of *A. vinelandii* by affinity chromatography to a Co2+ resin under anaerobic conditions inside a glove box. In order to maintain anaerobic conditions buffers for protein purification and analysis are sparged with purified N2 for 20-30 min.

The *A. vinelandii* cell-free extracts can be prepared by osmotic shock followed by centrifugation at 30,000×g for 1 h to remove cell debris. Cell-free extracts are loaded onto a 20-ml $Co^{2+}$-affinity column equilibrated in 10 mM sodium phosphate, 1.8 mM potassium phosphate buffer (pH 7.3), 140 mM NaCl, 2.7 mM KCl, 10% glycerol. The column is washed with 200 ml of 50 mM Tris-HCl buffer (pH 7.9), 500 mM NaCl, 25 mM imidazole, and the NifDK protein complex is eluted from the column by applying 40 ml of 50 mM Tris-HCl buffer (pH 7.9), 150 mM NaCl, 300 mM imidazole.

The *A. vinelandii* used in the present method contains an inactivated or a deleted NifB gene. Methods for inactivating or deleting a gene of interest in *A. vinelandii* are well known in the art. In a preferred embodiment, the *A. vinelandii* containing an inactivated or a deleted NifB gene is the UW140 strain The methods defined above require a step wherein the mixture is incubated under conditions allowing the synthesis of FeMo-co. The conditions will be evident to a person skilled in the art and could be easily identified by routine experimentation. By way of an example, the step wherein the mixture is incubated under conditions allowing the synthesis of FeMo-co is carried out in an $N_2$ atmosphere or in an Argon (Ar), at a temperature of between 10 and 40°, preferably at about 30° C. and during 5 min to 1 h, preferably for about 30 or 34 min.

Method for In Vitro Activation of Apo-NifDK According to the Invention

In a further aspect the invention relates to a method for in vitro activation of apo-NifDK comprising the steps of:
  i) contacting the FeMo-co obtained by any of the methods described above with apo-NifDK and,
  ii) incubating the mixture defined in (i) under conditions allowing the activation of apo-NifDK.

In an additional aspect, the invention further comprises a method for in vitro activation of apo-NifDK comprising the steps of:
  i) mixing NifB, apo-NifEN, NifH proteins with SAM or SAM generating system, molybdate or a molybdenum donating protein, R-homocitrate or a R-homocitrate generating system, a reducing agent, an ATP regenerating system and Mg-ATP, and, if desired, one or more of NifX, $Fe^{2+}$, and $S^{2-}$,
  ii) incubating the mixture defined in (i) under conditions allowing the synthesis of FeMo-co,
  iii) contacting the FeMo-co obtained in step ii) with apo-NifDK and,
  iv) incubating the mixture defined in (i) under conditions allowing the activation of apo-NifDK.

In an additional aspect, the invention further comprises a method for in vitro activation of apo-NifDK comprising the steps of:
  i) introducing into a cell a polynucleotide A polynucleotide encoding a fusion protein comprising NifB protein and a mitochondrial targeting peptide,
  ii) growing said cell under conditions allowing the expression of said NifB protein,
  iii) purifying said protein under anaerobic conditions,
  iv) mixing the NifB protein obtained in step iii), apo-NifEN, NifH proteins with SAM or SAM generating system, molybdate or a molybdenum donating protein, R-homocitrate or a R-homocitrate generating system, a reducing agent, an ATP regenerating system and Mg-ATP, and, if desired, one or more of NifX, $Fe^{2+}$, and $S^{2-}$, and
  v) incubating the mixture defined in (i) under conditions allowing the synthesis of FeMo-co,
  vi) contacting the FeMo-co obtained in step ii) with apo-NifDK and,
  vii) incubating the mixture defined in (i) under conditions allowing the activation of apo-NifDK.

In an additional aspect, the invention further comprises a method for in vitro activation of apo-NifDK comprising the steps of:
  i) Mixing NifB with a cell-free-extract from an *Azotobacter vinelandii* strain carrying a disrupted nifB gene, R-homocitrate or R-homocitrate generating system, molybdate or molybdenum donating protein, a reducing agent, an ATP regenerating system and ATP, and, if desired, Nif H, SAM or SAM generating system, $Fe^{2+}$, and $S^{2-}$,
  ii) incubating the mixture defined in (i) under conditions allowing the synthesis of FeMo-co,
  iii) contacting the FeMo-co obtained in step iii) with apo-NifDK and,
  iv) incubating the mixture defined in (i) under conditions allowing the activation of apo-NifDK.

In an additional aspect, the invention further comprises a method for in vitro activation of apo-NifDK comprising the steps of:
  i) introducing into a cell a polynucleotide a polynucleotide encoding a fusion protein comprising NifB protein and a mitochondrial targeting peptide,
  ii) growing said cell under conditions allowing the expression of said NifB protein,
  iii) purifying said NifB protein under anaerobic conditions,
  iv) mixing NifB obtained in step (iii) with a cell-free-extract from an *Azotobacter vinelandii* strain carrying a disrupted nifB gene, R-homocitrate or R-homocitrate generating system, molybdate or molybdenum donating protein, a reducing agent, an ATP regenerating system and ATP, and, if desired, Nif H, SAM or SAM generating system, $Fe^{2+}$, and $S^{2-}$ and
  v) incubating the mixture defined in (i) under conditions allowing the synthesis of FeMo-co,
  vi) contacting the FeMo-co obtained in step ii) with apo-NifDK and,
  viii) incubating the mixture defined in (i) under conditions allowing the activation of apo-NifDK.

Measurement of nitrogenase activity, may be performed for instance by an acetylene reduction assay, as shown in the examples of the invention, or other assay known in the art such as by measuring ammonia production, or $N_2$ isotope incorporation, or by production of hydrogen gas ($H_2$).

Kit of the Invention

In a final aspect the invention relates to a kit comprising:
(i) first polynucleotide or a first vector of the invention,
(ii) second polynucleotide or second expression vector or the invention encoding each of NifU, NifS or FdxN proteins.

(iii) reagents adequate for carrying out a method according to any of the aspects of the invention.

In the present invention a "kit" is understood as a product containing the different reagents and material to express an oxygen-sensitive protein in a eukaryotic cell according to the method of the invention. The term kit also encompasses a product containing the different agents and material to in vitro reconstitution of an active nitrogenase protein complex in a eukaryotic cell according to the invention. Illustrative examples of reagents useful to carry out the methods of the invention are medium to keep cells, buffers, saline, etc. In a preferred embodiment, the kit according to the invention further comprises a nitrogenase substrate. As used herein the term "nitrogenase substrate" is understood as the reactant which is consumed during the reaction catalyzed by the nitrogenase enzyme. Examples of nitrogenase substrates are without limitation, nitrogen gas (N2), nitrous oxide (N2O), cyanure, carbon monoxide, methyl isocyanate, azide, acetylene, cyclopropane, cyanamide, diazirine. In a still more preferred embodiment, said nitrogenase substrate is acetylene. In another still more preferred embodiment, said nitrogenase substrate is nitrogen gas (N2).

Another component which can be present in the kit is a packing which allows maintaining the agents properly stored. Suitable materials for preparing such packagings include glass, plastic (polyethylene, polypropylene, polycarbonate and the like), bottles, vials, paper, sachets and the like. The kit of the invention can additionally contain instructions for using the agents in the method to express an oxygen-sensitive protein in a eukaryotic cell of the invention and/or instructions for using agents in the method to reconstitute in vitro an active nitrogenase protein complex. Said instructions can be found in the form of printed material or in the form of an electronic support which can store instructions such that they can be read by a subject, such as electronic storage media (magnetic disks, tapes and the like), optical media (CD-ROM, DVD) and the like. The media can additionally or alternatively contain internet websites providing said instructions.

The invention is defined herein by the following aspects:
1. A polynucleotide encoding a fusion protein comprising NifB protein and a mitochondrial targeting peptide.
2. The polynucleotide according to aspect 1 further comprising at least one peptide tag adequate for detection or purification of the fusion protein.
3. The polynucleotide according to aspect 2 wherein the peptide tag is N-terminal to NifB and wherein the mitochondrial targeting peptide is N-terminal to said peptide tag.
4. The polynucleotide according to any of aspects 1 to 3 wherein the mitochondrial targeting peptide is the polypeptide of sequence SEQ ID NO:1 or SEQ ID NO:2.
5. The polynucleotide according to any of aspects 2 to 4 wherein the tag peptide is the polypeptide of sequence SEQ ID:3.
6. The polynucleotide according to any of aspects 1 to 5 wherein the sequences encoding the fusion protein have been codon optimized for expression in a eukaryotic cell.
7. The polynucleotide according to aspect 6 wherein the codon optimization is for expression in yeast or plants.
8. The polynucleotide according to aspect 7 wherein the codon optimization is for expression in *Saccharomyces cerevisiae* or *Nicotiana benthamiana*.
9. The polynucleotide according to any of aspects 1 to 8, wherein said NifB is from a prokaryotic organism.
10. The polynucleotide according to aspect 9, wherein said prokaryotic organism is *Azotobacter vinelandii* or *Methanocaldococcus infernus*.
11. An expression vector comprising the polynucleotide according to any of aspects 1 to 10.
12. A eukaryotic cell comprising the polynucleotide according to any of aspects 1 to 10 or an expression vector according to aspect 11.
13. The eukaryotic cell according to aspect 12, which grows under aerobic conditions.
14. The eukaryotic cell according to aspects 12 or 13, wherein said eukaryotic cell is a yeast or a plant cell.
15. Method for expressing NifB protein in a eukaryotic cell comprising the steps of:
   iv) introducing into said cell a polynucleotide according to any of aspects 1 to 10 or a vector according to aspect 11,
   v) growing said cell under conditions allowing the expression of said protein and, if desired,
   vi) purifying said protein under anaerobic conditions.
16. The method according to aspect 15 wherein the purification step is performed at pH between 7 and 8 and a temperature between 55 and 65° C.
17. A NifB protein obtained by the method of any of aspects 15 or 16.
18. The NifB protein according to aspect 17 wherein said protein has at least 6 Fe atoms per monomer of protein.
19. A polynucleotide encoding a fusion protein comprising any of NifU, NifS or FdxN proteins and a mitochondrial targeting peptide.
20. The polynucleotide according to aspect 19 further comprising a peptide tag.
21. The polynucleotide according to any of aspects 19 or 20, wherein the mitochondrial targeting peptide is the peptide of sequence SEQ ID:1 or SEQ ID NO:2, and wherein the peptide tag is selected from hemagglutinin peptide, the peptide of sequence SEQ ID NO:3 and polyhistidine.
22. The polynucleotide according to any of aspects 19 to 21, wherein NifU, NifS or FdxN proteins are from a prokaryotic organism.
23. The polynucleotide according to aspect 22 wherein the prokaryotic organism is *Azotobacter vinelandii*.
24. The polynucleotide according to any of aspects 19 to 23 wherein the sequences encoding the fusion protein have been codon optimized for expression in a eukaryotic cell.
25. The polynucleotide to aspect 24 wherein the codon optimization is for expression in yeast or plants.
26. The polynucleotide according to aspect 25 wherein the codon optimization is for expression in *Saccharomyces cerevisiae* or *Nicotiana benthamiana*.
27. An expression vector comprising the polynucleotide according to any of aspects 19 to 26.
28. A eukaryotic cell comprising the polynucleotides according to any of aspects 19 to 26, or the expression vector according to aspect 27.
29. The eukaryotic cell according to aspect 28, wherein the cell comprises at least one copy of a polynucleotide or expression vector encoding each of the proteins NifU, NifS and FdxN.
30. The eukaryotic cell according to aspect 29 additionally comprising a polynucleotide according to any of aspects 1 to 10 or an expression vector according to aspect 11.
31. The eukaryotic cell according to any of aspects 28 to 30, which grows under aerobic conditions.

32. Method for expressing NifU, NifS or FdxN proteins in a eukaryotic cell comprising the steps of:
   i) introducing into said cell a polynucleotide according to any of aspects 19 to 26 or a vector according to aspect 27,
   ii) growing said cell under conditions allowing the expression of said protein and, if desired,
   iii) purifying said protein under anaerobic conditions.
33. A NifU, NifS or FdxN protein obtained by the method of aspect 32.
34. Method for in vitro synthesis of FeMo-co using NifB comprising the steps of:
   i) mixing NifB, apo-NifEN, NifH proteins with SAM or SAM generating system, molybdate or molybdenum donating protein, R-homocitrate or R-homocitrate generating system, a reducing agent, an ATP regenerating system and Mg-ATP, and, if desired, any or all of these components NifX, $Fe^{2+}$, and $S^{2-}$,
   iii) incubating the mixture defined in (i) under conditions allowing the synthesis of FeMo-co.
35. Method for in vitro synthesis of FeMo-co comprising the steps of:
   iii) mixing NifB with a cell-free-extract from an *Azotobacter vinelandii* strain carrying a disrupted nifB gene, R-homocitrate or R-homocitrate generating system, molybdate or molybdenum donating protein, a reducing agent, an ATP regenerating system and ATP, and, if desired, NifH, SAM or SAM generating system, $Fe^{2+}$, and $S^{2-}$,
   iv) incubating the mixture defined in (i) under conditions allowing the synthesis of FeMo-co.
36. Method for in vitro activation of apo-NifDK comprising the steps of:
   iii) contacting the product obtained in any of aspects 34 or 35 with apo-NifDK and,
   iv) incubating the mixture defined in (i) under conditions allowing the activation of apo-NifDK.
37. A kit comprising:
   i) a polynucleotide according to any of aspects 1 to 10 or an expression vector according to aspect 11,
   ii) polynucleotides according to any of aspects 19 to 26 or expression vectors according to aspect 26 encoding each of NifU, NifS or FdxN proteins.
   iii) reagents adequate for carrying out a method according to any of aspects 34 to 35.

The invention is described herein by way of the following examples which are to be construed as merely illustrative and not limitative of the scope of protection.

EXAMPLES

Materials and Methods

Generation of Plasmid for Galactose-Induce Yeast Expression

*E. coli* DH5a was used for storage and amplification of yeast expression pESC vectors (Agilent Technologies). *E. coli* was grown at 37° C. in Luria-Bertani (LB) medium supplemented with appropriate antibiotics. Yeast optimized coding sequences for nifU, nifS, nifB (*A. vinelandii* and *M. infernus*) and fdxN with in-frame SU9 leader sequences (Westermann and Neupert, 2000) were generated by GenScript, or by overlapping PCR reactions as specified below, and cloned into pESC vectors (Agilent Technologies) using standard techniques. SU9-nifU and SU9-nifS were cloned into pESC-URA using BamHI/HindIII and EcoRI/BgIII, respectively, generating pN2GLT4. SU9-fdxN and SU9-His10-nifBAv were cloned into pESC-TRP using NotI/ClaI and BamHI/SalI, respectively, generating pN2GLT18. SU9-nifBAv-His10 and SU9-nifBMi-His10 were created using overlapping PCR, to add su9 and Nis10 at the 5% and 3% termini of nifBAv (from *Azotobacter vinelandii*) and nifBMi (from *Methanocaldococcus infernus*). Primers used for generating SU9-nifBAv-His10 were 5% ATTTCGGTTTGTATTACTTC-3' (SEQ ID NO: 36) and 5% CATG-GAAGAGTAGGCGC-3' (SEQ ID NO: 37) (using pN2GLT18 as template), 5% GCGCCTACTCTTCCATG-GAATTGTCTGTTTTGGGT-3' (SEQ ID NO: 38) and 5% ATGATGGTGGTGGTGATGATGATGAGCCT-TAGCTTGCAAC-3' (SEQ ID NO: 39) (using pN2GLT18 as template), 5% ATCACCACCACCATCATCACCAT-TAAGTCGACATGGAACA-3' (SEQ ID NO: 40) and 5'-GTACACGCGTCTGTACAGAA-3' (SEQ ID NO: 41) (using pN2GLT18 as template), to amplify SU9, nifBAv and Nis10, respectively. 5% ATTTTCGGTTTGTATTACTTC-3' (SEQ ID NO: 36) and 5'-GTACACGCGTCTGTACAGAA-3' (SEQ ID NO: 41) were used for the overlapping PCR reaction. Primers used for generating SU9-nifBMi-His10 were 5% ATTTTCGGTTTGTATTACTTC-3' (SEQ ID NO: 36) and 5% CATGGAAGAGTAGGCGC-3' (SEQ ID NO: 37) (using pN2GLT18 as template), 5% GCGCC-TACTCTTCCATGGAGAAAATGTCTAAATTT-3' (SEQ ID NO: 42) and 5'-ATGATGGTGGTGGTGATGAT-GATGGTGTGAGAAATGCTTC-3' (SEQ ID NO: 43) (using nifBMi as template), 5% ATCACCACCACCATCAT-CACCATTAAGTCGACATGGAACA-3' (SEQ ID NO: 40) and 5'-GTACACGCGTCTGTACAGAA-3' (SEQ ID NO: 41) (using pN2GLT18 as template), to amplify su9, nifBMi and Nis10, respectively. 5'-ATTTTCGGTTTGTAT-TACTTC-3' (SEQ ID NO: 36) and 5'-GTA-CACGCGTCTGTACAGAA-3' (SEQ ID NO: 41) were used for the overlapping PCR reaction. SU9-nifBAv-His10 and SU9-nifBMi-His10 were cloned into pN2GLT18, replacing SU9-His10-nifBAv using BamHI/SalI, and generating pN2SB22 and pN2SB24, respectively. su9-fdxN-HA was created using overlapping PCR, to add HA at the 3'-terminus of su9-fdxN. Primers used for generating su9-fdxN-HA were 5'-GGTGGTAATGCCATGTAATATG-3' (SEQ ID NO: 44) and 5% GCATAATCTGGAACATCATATGGA-TACCTTGCCTGTATTT-3' (SEQ ID NO: 45) (using pN2SB22 as template), 5% GATGTTCCAGATTATGCT-TAAGAGCTCTTAATTAACAATT-3' (SEQ ID NO: 46) and 5'-AAAGTTTAAACCGCATCAGGAAATTGTAA-3' (SEQ ID NO: 47) (using pN2SB22 as template), to amplify su9-fdxN and HA, respectively. 5'-GGTGGTAATGC-CATGTAATATG-3' (SEQ ID NO: 44) and 5"-AAAGTT-TAAACCGCATCAGGAAATTGTAA-3' (SEQ ID NO: 47) were used for the overlapping PCR reaction. su9-fdxN-HA was cloned into pN2SB24, replacing su9-fdxN using NotI/PacI, generating pN2SB39. To make pN2GLT18 (su9-fdxN and su9-His10-nifBAv) compatible with transformation into prototrophic *S. cerevisiae* CEN.PK113-7D clone DOE56, the LEU2 auxotrophic marker was replaced with the hygromycin marker hphMX4 (Buren et al 2017), generating pN2SB15.

Yeast optimized coding sequence for twinstrep with in-frame su9 leader sequence was generated by GenScript. Yeast optimized coding sequence for *M. infernus* nifB (nifBMi) was generated by ThermoFisher. Sequence coding for su9-twinstrep-nifBMi was created by overlapping PCR reactions as specified below, and cloned into pN2SB22 using standard techniques. Primers used for generating su9-twinstrep-nifBMi were 5'-AAAAAGATCTATGGCCTC-CACTCGTGT-3' (SEQ ID NO: 48) and 5'-TTTTCCATG- GATCCTTCGAGTTTTTCAAATTGTGGATGTG-3' (SEQ ID NO: 49) (using GenScript su9-twinstrep fragment as template), 5'-TTGAAAAACTCGAAGGATCCATGGAAAAGATGTCCAA-3' (SEQ ID NO: 50) and 5'-TTTTTCTCGAGGTCACCTCAATGAGA-3' (SEQ ID NO: 51) (using ThermoFisher nifBMi fragment as template), to amplify su9-twinstrep and nifBMi, respectively. 5'-AAAAAGATCTATGGCCTCCACTCGTGT-3' (SEQ ID NO: 48) and 5'-TTTTTCTCGAGGTCACCTCAATGAGA-3' (SEQ ID NO: 51) were used for the overlapping PCR reaction. su9-twinstrep-nifBMi was digested with BglII/XhoI and cloned into pN2SB22, digested with BamHI/XhoI, replacing su9-nifBAv-His10 and generating pN2SB44. su9-twinstrep-nifBMi was cloned into pESC-LEU using AgeI/NheI, generating pN2XJ154. su9-twinstrep-nifBMi was cloned into pN2SB39 using AgeI/NheI, replacing su9-nifBAv-His10 and generating pN2XJ155.

Generation of Yeast Strains, Growth, Protein Expression and Mitochondria Isolation

*Saccharomyces cerevisiae* W303-1a (MATa leu2-3,112 trp1-1 can1-100 ura3-1 ade2-1 his3-11,15) was the host strain for expression vectors pN2GLT4 and pN2SB22 (to generate strain SB09Y), pN2GLT4 and pN2SB24 (to generate strain SB10Y), and pN2GLT4 and pN2SB39 (to generate strain SB12Y). CEN.PK113-7D (MATa URA3 TRP1 LEU2 HIS3 MAL2-8c SUC2) strain DOE56 (having constitutive expression of mitochondria targeted NifU and NifS) (Buren et al., 2017) was the host strain for expression vector pN2SB15 (to generate strain SB03Y). *Saccharomyces cerevisiae* W303-1a (MATa leu2-3,112 trp1-1 can1-100 ura3-1 ade2-1 his3-11,15) was the host strain for expression vectors pN2GLT4 and pN2SB44 (to generate strain SB17Y), pN2XJ154 (to generate strain SB30Y), pN2GLT4 and pN2XJ154 (to generate strain SB31Y), pN2XJ155 (to generate strain SB32Y), and pN2GLT4 and pN2XJ155 (to generate strain SB33Y). Yeast transformations were carried out according to the lithium acetate method (Gietz and Schiestl, 2007). See table 1 for details about recombinant yeast strains.

TABLE 1

Yeast expression plasmids and yeast strains

| Strain | Plasmids | Expressed proteins | Full-length (kDa) | Processed (kDa) |
|---|---|---|---|---|
| SB09Y | pN2GLT4 | SU9-NifU | 40.6 | 33.6 |
|  |  | SU9-NifS | 51.0 | 44.0 |
|  | pN2SB22 | SU9-FdxN | 17.1 | 9.8 |
|  |  | SU9-NifB$_{Av}$-His10 | 63.6 | 56.3 |
| SB10Y | pN2GLT4 | SU9-NifU | 40.6 | 33.6 |
|  |  | SU9-NifS | 51.0 | 44.0 |
|  | pN2SB24 | SU9-FdxN | 17.1 | 9.8 |
|  |  | SU9-NifB$_{Mi}$-His10 | 43.8 | 36.4 |
| SB03Y | pN2SB15 | SU9-FdxN | 17.1 | 9.8 |
|  |  | SU9-His10-NifB$_{Av}$ | 63.6 | 56.3 |
| SB12Y | pN2GLT4 | SU9-NifU | 40.6 | 33.6 |
|  |  | SU9-NifS | 51.0 | 44.0 |
|  | pN2SB39 | SU9-FdxN-HA | 18.2 | 10.9 |
|  |  | SU9-NifB$_{Mi}$-His10 | 43.8 | 36.4 |
| SB17Y | pN2GLT4 | SU9-NifU | 40.6 | 33.6 |
|  |  | SU9-NifS | 51.1 | 44.0 |
|  | pN2SB44 | SU9-TS-NifB$_{Mi}$ | 45.3 | 38.6 |
|  |  | SU9-FdxN | 17.1 | 9.8 |
| SB30Y | pN2XJ154 | SU9-TS-NifB$_{Mi}$ | 45.3 | 38.6 |
| SB31Y | pN2GLT4 | SU9-NifU | 40.6 | 33.6 |
|  |  | SU9-NifS | 51.1 | 44.0 |
|  | pN2XJ154 | SU9-TS-NifB$_{Mi}$ | 45.3 | 38.6 |
| SB32Y | pN2XJ155 | SU9-TS-NifB$_{Mi}$ | 45.3 | 38.6 |
|  |  | SU9-FdxN-HA | 18.2 | 10.9 |
| SB33Y | pN2GLT4 | SU9-NifU | 40.6 | 33.6 |
|  |  | SU9-NifS | 51.1 | 44.0 |
|  | pN2XJ155 | SU9-TS-NifB$_{Mi}$ | 45.3 | 38.6 |
|  |  | SU9-FdxN-HA | 18.2 | 10.9 |

*Saccharomyces cerevisiae* were grown in flasks at 28° C. and 200 rpm in synthetic drop-out (SD) medium (1.9 g/l yeast nitrogen base, 5 g/l ammonium sulfate, 20 g/l glucose, and Kaiser drop-out mixture (Kaiser et al., 1994) (SC-His-Leu-Trp-Ura, FORMEDIUM) supplemented with 20 mg/l adenine and 40 mg/l tryptophan, 40 mg/l histidine, 20 mg/l uracil, 60 mg/l leucine, depending on auxotrophic requirements).

Plasmid for the inducible expression of SU9-FdxN and SU9-His10-NifBAv in transformed DOE56 (SB03Y) was maintained by supplementing the inoculum growth media with 300 mg/l hygromycin. Galactose induction for small-scale protein extracts was performed in the above-described SD medium in which glucose was replaced by 20 g/l galactose, and additionally supplemented with 0.1% yeast extract and 1% peptone.

Total yeast protein extracts to verify protein expression were prepared in order to retain small proteins (2). Typically, pellets of 1-2 ml cultures were resuspended in 20 µl lysis buffer (100 mM NaOH, 50 mM EDTA, 2% SDS, 2% β-mercaptoethanol (β-ME), 1 mM phenyl-methylsulfonyl fluoride (PMSF)) per ODxml culture and heated at 90° C. for 10 min. Subsequently, 10 µl 1 M acetic acid was added per 100 µl lysis buffer and samples were vortexed for 30 sec. Double concentrated Laemmli buffer (2xLB) was added and samples were again heated at 90° C. for 10 min. Finally, the supernatant following centrifugation using a bench-top centrifuge operating at full speed was analyzed by SDS-PAGE. Total yeast protein extracts of strain SB17Y were used to analyze temperature-dependent solubility of TS-NifB as previously described (1). Similar loading on SDS-PAGE experiments was obtained by preparing samples according to optical density, and was confirmed by using either Commassie staining of polyacrylamide gels or Ponceau staining of nitrocellulose membranes. Additionally, immunoblotting with antibodies against tubulin or HSP60 were used as control of gel loading and sample precipitation. Mitochondria isolations were performed as previously described (Diekert K, et al 2001, Methods Cell Biol. 65, 37-51)). Enrichment was verified using tubulin (cytoplasmic) and HSP60 (mitochondria) marker proteins. Mitochondria isolations were performed as described in Diekert K et al (Methods cell Biol, 2001, 65, 37-51). Enrichment was verified using tubulin (cytoplasmic and HSP60 (mitochondria) marker proteins.

Cultures for yeast expressed NifB purifications were grown in a 4 l fermenter (BIO-STAT). Cultures were grown at 30° C. in selective SD-medium for 16 h, followed by 8 h in rich medium (0.25% yeast extract, 0.25% bactopeptone, 0.25% bactotryptone, 2.5% sucrose), supplemented with 25 mg/l ammonium iron(III) citrate, 0.225 mM iron (II) sulfate, 1.25 mM magnesium sulfate, 1.5 mM calcium chloride and trace element solution (Lopez-Torrejón et al Nat, Commun 7, 11426, 2016). Finally, protein expression was induced for 16 h by addition of 2.25% galactose, 0.25% bactopeptone, 0.25% bactotryptone and vitamin solution (Lopez-Torrejón et al Nat, Commun 7, 11426, 2016). The pH was automatically maintained around 5 using 0.8 M ammonium hydroxide. Air flow was maintained at 2.5 l air/min per 4 l culture, at 250 rpm. Dissolved oxygen dropped to zero (as measured by oxygen sensor, Mettler Toledo) before addition of galactose, and remained at zero during the rest of the process.

Solubility of Yeast-Expressed NifB

*Saccharomyces cerevisiae* cells expressing yNifBAv and yNifBMi were resuspended in 5 volumes of lysis buffer (100 mMTris-HCl, 400 mM NaCl, 5 mM b-mercaptoethanol (b-ME), 1 mM phenylmethylsulfonyl fluoride (PMSF)), at pH 7 or 8 with 10% or 30% glycerol. Cells were broken in 2 ml tubes using 0.5 mmglass beads (BioSpec Products) in a mixer mill (Retsch MM300) operating at 30 Hz in 3 cycles of 1 min at 4° C. Lysates were incubated at room temperature (RT), or heated at 5° C. temperature intervals from 40° C. to 75° C., for 30 min. The supernatant after 20 min centrifugation at 20,000×g and 4° C. containing soluble proteins was analyzed by SDS-PAGE and immunoblot analysis.

Preparation of Yeast Anaerobic Cell-Free Extracts and His Tagged NifB Purifications

*S. cerevisiae* cells expressing His-tagged Nif proteins and SU9-Twin-Strep-NifBMi (TS-Nif B) were resuspended in anaerobic buffer A (100 mM Tris-HCl pH 8.8, 300 mM NaCl, 10% glycerol) supplemented with 2 mM dithionite (DTH), 5 mM □-ME, 1 mM PMSF, 1 µg/ml leupeptin and 5 µg/ml DNAse I. The cells were lysed in an Emulsiflex-05 homogenizer (Avestin Inc.) at 25,000 lb per square inch. Cell-free extracts (CFE) were obtained by removal of cell debris and precipitated yeast proteins by centrifugation (50,000×g for 1 h at 4° C.) and filtration through a 0.2 µM pore size filter (Nalgene Rapid-Flow, Thermo Scientific). All procedures were performed under anaerobic conditions.

*Saccharomyces cerevisiae* cells expressing SU9-His10-NifBAv were lysed as described above, in buffer with detergents (50 mM Tris-HCl pH 8, 200 mM KCl, 10% glycerol, 5 mM b-ME, 0.05% n-dodecyl-b-D-maltopyranoside, 0.1% triton X-100 and 0.1% Tween 20) as previously described for purification of NifBMi from *E. coli* (Wilcoxen et al., 2016).

His-tagged yNifBMi was purified by Co2+ affinity chromatography under anaerobic conditions (<0.1 ppm of 02) using an AKTA Prime FPLC system (GE Healthcare) inside a glovebox (MBraun). All buffers were previously made anaerobic by sparging with N2. Before loading the affinity column, the cell-free extract was diluted to reach 50 mM Tris-HCl, while maintaining other buffer components. Typically, anaerobic cell-free extract from 100 g of cell paste was loaded at 2 ml/min onto a column filled with 5 ml of IMAC resin (GE Healthcare) equilibrated with buffer A (50 mM Tris-HCl pH 8, 400 mM NaCl, 10% glycerol, 2 mM DTH, 5 mM b-ME) and washed with four successive washes of buffer A supplemented with 0, 10, 40 and 100 mM imidazole (10-15 column volumes per wash), respectively. Bound protein was eluted in two steps, with buffer A containing 200 and 500 mM imidazole, respectively. Eluted fractions showing the desired purity were pooled and concentrated using a 100 kDa cutoff pore centrifugal membrane device (Amicon Ultra-15, Millipore), and then desalted in PD10 columns (GE Healthcare) equilibrated with buffer A. Pure yNifBMi was frozen and stored in liquid N2.

TS-NifB was purified by Strep-tag binding chromatography using a 5 ml Strep-Tactin XT Superflow Cartridge (IBA Lifesciences) under anaerobic conditions (<0.1 ppm of O2) using an AKTA Prime FPLC system (GE Healthcare) inside a glovebox (MBraun). All buffers were previously made anaerobic by sparging with N2. Before loading the cell-free extract, the Strep-Tactin column was equilibrated with buffer B (100 mM Tris-HCl pH 8.0, 300 mM NaCl, 10% glycerol, 2 mM DTH, 5 mM β-ME). pH above 7.5 of the cell-free extract was ensured before loading. Typically, anaerobic cell-free extract from 100 g of cell paste was loaded at 2 ml/min and washed with five successive washes of 15 ml buffer B. Bound protein was typically eluted with 12 ml buffer B supplemented with 50 mM biotin and desalted using a HiPrep 26/10 Desalting column (GE Healthcare) equilibrated with buffer C (50 mM Tris-HCl pH 8.0, 300 mM NaCl, 10% glycerol, 5 mM β-ME). Purity of the TS-NifB protein was verified by SDS-PAGE and Coomassie staining, concentrated using a 10 kDa cutoff pore centrifugal membrane device (Amicon Ultra-15, Millipore) and analyzed by UV-visible spectroscopy. Finally, pure TS-NifB was supplemented with 2 mM DTH, frozen and stored in liquid $N_2$.

UV-Visible Spectroscopy, N-Terminal Sequencing and Protein Methods

As-isolated TS-NifB preparations were used for colorimetric Fe determination (5), in vitro FeMo-co synthesis and nitrogenase activity assays (see sections below), and UV-visible spectroscopy. UV-visible absorption spectra were recorded under anaerobic conditions in septum-sealed cuvettes using a Shimadzu UV-2600 spectrophotometer. When indicated, anaerobic samples were exposed to air during 5 min. UV-visible absorption spectra were recorded against buffer C as baseline. Absorbance at 800 nm was subtracted and spectra were then normalized to 279 nm. The N-terminal amino acid sequence of purified TS-NifB was determined by Edman degradation (Proteome Factory AG). Protein concentrations were measured using the BCA protein assay (PIERCE). Samples were pre-treated with iodoacetamide before performing the BCA assay to eliminate the interfering effect of DTH.

In Vitro Reconstitution of yNifBMi Fe—S Clusters, US-Visible Spectroscopy, N-Terminal Sequencing and Protein Methods In vitro reconstitution of purified yNifBMi was performed as previously described with modifications (Curatti et al., 2006). Pure yNifBMi stored in buffer A was buffer-exchanged to buffer B (50 mM Tris-HCl pH 8, 400 mM NaCl, 10% glycerol, 5 mM b ME) by using a PD10 column to recover "as isolated" protein. The desalted sample (20 mMNifB monomer) was incubated with 10 mM DTT at room temperature inside a glovebox (MBraun) for 10 min. (NH4)2Fe(SO4)2 and Na2S were then added at 20-fold molar excess ratio and incubated at 35° C. overnight. yNifBMi was again desalted in buffer B to recover "reconstituted" protein. As isolated and reconstituted proteins were used for colorimetric Fe (Fish, 1988) and S (Beinert, 1983) determination, in vitro FeMo-co synthesis and nitrogenase activity assays, and UV-visible spectroscopy. UV-visible absorption spectra were recorded under anaerobic conditions in septum-sealed cuvettes using a Shimadzu UV-2600 spectrophotometer. When indicated, 5 mM DTH was added to reconstituted yNifBMi. UV-visible absorption spectra were recorded against buffer B as baseline. Absorbance at 800 nm was subtracted and spectra were then normalized to 279 nm. The N-terminal amino acid sequence of purified yNifBMi was determined by Edman degradation (Proteome Factory AG). Protein concentrations were measured using the BCA protein assay (PIERCE). NifB samples were pre-treated with iodoacetamide before performing the BCA assay to eliminate the interfering effect of DTH (Hill and Straka, 1988).

In Vitro Synthesis of FeMo—Co and Apo-NifDK Reconstitution Assay Using *Azotobacter vinelandii* ΔnifB Strain Cell-Free Extract and His-Tagged NifB Protein In vitro yNifBMi dependent FeMo-co synthesis and nitrogenase reconstitution reactions were performed in 9-ml serum vials sealed with serum stoppers (Curatti et al., 2006). Complete reactions contained 17.5 mM Na2MoO4, 175 mM homocitrate, 1.75 mM (NH4)2FeSO4, 1.75 mM Na2S, 880 mM SAM, 1.23 mM ATP, 18 mM phosphocreatine, 2.2 mM MgCl2, 3 mM DTH, 40 mg/ml creatine phosphokinase, 2.2 mM NifH (dimer), 2.9 mg/ml UW140 (*A. vinelandii* 1nifB) proteins, 5 mM (or 0-10 mM titration) reconstituted yNifBMi (monomer) in 22 mM Tris-HCl (pH 7.5). The reactions (total volume of 500 ml) were incubated at 30° C. for 35 min to allow for FeMo-co synthesis and insertion reactions. NifB-co-dependent in vitro FeMo-co synthesis assays were performed using 2 mM NifB-co isolated from *K. oxytoca* (Shah et al., 1994). Following in vitro synthesis of FeMo-co, activation of apo-MoFe nitrogenase present in UW140 extract was analyzed following addition of excess NifH and ATP-regenerating mixture (total volume 1 ml) by acetylene reduction assay at 30° C. for 30 min following standard procedures (Shah and Brill, 1973). Positive control reactions for acetylene reduction were carried out with pure preparations of *A. vinelandii* Fe protein and MoFe protein incubated with ATP-regenerating mixture at 30° C. during 30 min.

In Vitro Synthesis of FeMo—Co and Apo-NifDK Reconstitution Assay Using *Azotobacter vinelandii* ΔnifB Strain Cell-Free Extract and TS-NifB Proteins Assays were performed as described by Curatti et al. (7), with slight modifications. Reactions were prepared inside a glovebox (CoyLabs) using 9 ml serum vials previously washed with 1 ml anaerobic buffer. The in vitro FeMo-co synthesis and insertion reactions were performed in 400 μl total volume that included 50 μl reaction buffer (25 mM Tris-HCl pH 7.8, 17.5 μM Na2MoO4, 175 μM R-homocitrate, 880 μM SAM, 3 mM DTH, 2 μM NifH), 100 μl ATP mix (3.6 mM ATP, 59 mM phosphocreatine disodium salt, 7.5 mM MgCl2, 7.5 mM DTH, 500 μg/ml creatine phosphokinase), 2 μM NifH and 200 μl of UW140 (*A. vinelandii* ΔnifB) cell-free-extract (at 14.64 mg/ml total protein concentration). Finally, 50 μl buffer (25 mM Tris-HCl pH 7.8), or buffer supplemented with TS-NifB (12.5 μM final concentration), or NifB-co as positive control reaction, (10 μM Fe final concentration) was added. The N2 atmosphere was changed to argon (Ar) and vials were incubated for FeMo-co synthesis and insertion at 30° C. for 35 min.

Following in vitro synthesis of FeMo-co, activation of apo-NifDK present in UW140 extract was analyzed following addition of excess NifH and ATP-regenerating mixture (total volume 0.8 ml) by acetylene reduction assay at 30° C. for 15 min following standard procedures (8). Positive control reactions included *A. vinelandii* DJ (wild-type) cell-free extract, *A. vinelandii* UW140 cell-free extract complemented with NifB-co from *K. pneumoniae* strain UC32 [UN1217, nifN::mu, Ptac::gst-nifX] (9), or [Fe—S] cluster reconstituted yeast NifBMi-His10.

In Vitro FeMo—Co Synthesis and Insertion Assays in Defined System with Purified Proteins Assays were performed as described by Curatti et al. (10), with slight modifications. Unless specified, NifB-dependent FeMo-co synthesis assays were performed in 100 μl reactions containing 17.5 μM Na2MoO4, 175 μM R-homocitrate, 125 μM FeSO4, 125 μM Na2S, 125 μM SAM, 1.23 mM ATP, 18 mM phosphocreatine disodium salt, 2.2 mM MgCl2, 3 mM DTH, 40 μg/ml creatine phosphokinase, 5.0 μM TS-NifB, 3.0 μM NifX, 1.5 μM apo-Nif EN, 3.0 μM NifH, 0.6 μM apo-NifDK and 1 mg/ml BSA in 22 mM Tris-HCl buffer pH 7.5. FeMo-co synthesis and insertion into apo-NifDK was performed under N2 atmosphere at 30° C. for 45 min.

Following in vitro synthesis of FeMo-co, activation of apo-NifDK was analyzed by addition of 500 μl of 2.0 μM NifH and ATP-regenerating mixture (1.23 mM ATP, 18 mM phosphocreatine disodium salt, 2.2 mM MgCl2, 3 mM DTH, 40 μg/ml creatine phosphokinase, final concentrations in 22 mM Tris-HCl pH 7.5 buffer) in 9 ml vials under Ar atmosphere. Acetylene reduction assays were performed at 30° C. for 15 min following standard procedures (8). Positive control reactions for acetylene reduction were carried out with pure preparations of *A. vinelandii* holo-NifDK, or apo-NifDK activated using apo-Nif EN supplemented with NifB-co (25 μM Fe final concentration) (9). The purification of other proteins used in the assay has been previously described (11).

Generation of Plant Expression Vectors and Protein Expression in Leaves of *N. Benthamiana Escherichia coli* DH5a was used for storage and amplification of plant expression vectors. *E. coli* was grown at 37_C in LB medium supplemented with appropriate antibiotics. su9-nifBAv-His10 and su9-nifBMi-His10 were PCR amplified using primers 5'AAAAGGATCCAATGGCCTC-CACTCGTGTCCTCG-3' (SEQ ID NO: 52) and 5% TTTT-CACGTGTTAATGGTGATGATGGTGGTG-3' (SEQ ID NO: 53), with pN2SB22 and pN2SB24 as templates, respectively. su9-nifBAv-His10 and su9-nifBMi-His10 were digested with BamHI and PmlI, and inserted into pGFP-GUSPlus vector (Vickers et al., 2007) (Addgene plasmid #64401) digested with BglII and PmlI, replacing GUS and generating pN2XJ13 (su9-nifBAv-His10) and pN2XJ14 (su9-nifBMi-His10), respectively. su9-nifBAv was PCR amplified using primers 5' AAAAGCTAGCATGGCCTC-CACTCGTGTCCTCG-3' (SEQ ID NO: 54) and 5% TTTTGCTAGCGCCTTAGCTTGCAACAAAGC-3' (SEQ ID NO: 55), with pN2SB22 as template. su9-nifBAv was digested with NheI and inserted into pGFPGUSPlus vector digested with XbaI, generating pN2XJ15 for expression of su9-nifBAv-gfp. su9-nifBMi was PCR amplified using primers 5% AAAAGCTAGCATGGCCTC-CACTCGTGTCCTCG-3' (SEQ ID NO: 54) and 5% TTTTGCTAGCGCGTGTGAGAAATGCTTCAAGTCG-3' (SEQ ID NO: 56), with pN2SB24 as template. su9-nifBMi was digested with NheI and inserted into pGFPGUSPlus vector digested with XbaI, generating pN2XJ16 for expression of su9-nifBMi-gfp. DNA sequence encoding the enhanced 35S promoter and an in-frame fusión of the cox4 mitochondria leader sequence (Köhler et al., 1997) with the 28 amino acid Twin-Strep-tag was generated by ThermoFisher. The E35S-cox4-twinStrep DNA sequence was flanked by HindIII and BglII, with a BamHI site additionally added 50 of the BglII site. E35S-cox4-twinStrep was digested with HindIII and BglII, and inserted into pGFP-GUSPlus vector also digested with HindIII and BglII, to generate pN2SB41. DNA sequence encoding egfp was PCR amplified using primers 5% AAAAAGGATCCATGGT-GAGCAAGGGCGA-3' (SEQ ID NO: 57) and 5% AAAAAGGTCACCTTACTTGTACAGCTCGTCCATG-3' (SEQ ID NO: 58), and pGFPGUSPlus as template. egfp was digested with BamHI and BstEII, and inserted into pN2SB41 also digested with BamHI and BstEII, creating pN2XJ17. pN2XJ17 was digested with PstI to remove the non-targeted EGFP, to generate pN2XJ19 (cox4-twinStrep-gfp). DNA sequences encoding nifBAv and nifBMi, flanked by BamHI and BstEII, were generated by ThermoFisher. nifBAv and nifBMi were digested with BamHI and BstEII, and inserted into pN2SB41 also digested with BamHI and BstEII, to generate pN2XJ20 (cox4-twinStrep-nifBAv) and pN2XJ21 (cox4-twinStrep-nifBMi). DNA and protein sequences of all constructs are listed in Supplementary FIG. S8. Agrobacterium tumefaciens strain GV3101(pMP90) was transformed with plasmids pN2XJ13, pN2XJ14, pN2XJ15, pN2XJ16, pN2XJ19, pN2XJ20, pN2XJ21 and the silencing suppressor p19 (Huang et al., 2009). The pDCL-mito-mRFP1 mitochondria marker (Mito-RFP) in A. tumefaciens strain C58 (Candat et al., 2014) was kindly provided by Prof. Macherel and Prof. Logan at the Angers University (France). A. tumefaciens mediated infiltration of N. benthamiana leaves was essentially performed as described by Leuzinger and colleagues (Leuzinger et al., 2013). Three to four days post infiltration, plant tissue was used for protein extraction or confocal microscopy. Protein extracts were prepared from infiltrated N. benthamiana leaf tissue in lysis buffer (100 mM Tris-Cl pH 8, 150 mM NaCl, 10 mM MgCl2, 0.2% NP-40, 5% glycerol, 5 mM b-ME and 5 mM ethylenediaminetetraacetic acid (EDTA)). Two hours before use, 5% polyvinylpolypyrrolidone (PVPP) was added to lysis buffer and, just before use, 1 mM PMSF, 1 mg/ml leupeptin and 1× protease inhibitor cocktail (P8215, Sigma) were added. Extraction was performed at a 2:1 ratio of buffer to tissue. Ten leaf discs of 5 mm diameter each (approximate weight of 200 mg) were added to a 2-ml Eppendorf tuve containing a 7-mm diameter steel ball. Tubes were kept in liquid N2 until use. Leaf tissue was broken using mixer mill (Retsch MM300) operating at 30 Hz for 1 min at 4_C. The dry tissue powder was supplemented with 400 ml lysis buffer and mixed for another 1 min at 30 Hz and 4_C. The broken tissue in lysis buffer was further incubated on an orbital shaker for 30 min at 4_C. One hundred ml extract were added to 100 ml 2× Laemmli buffer (2×LB) and heated for 10 min at 95_C to obtain the "total extract". The rest of the extract was centrifuged at 20,000×g for 30 min at 4_C to separate pellet from supernatant. The supernatant "soluble extract (S)" was mixed with 2×LB and heated for 10 min at 95_C. The pellet (P) was resuspended in 1 ml lysis buffer (no additional PVPP added) and centrifuged at 20,000×g for 10 min at 4_C. Finally, the pellet was resuspended in 800 ml 2×LB and heated for 10 min at 95_C. Ten ml of each fraction were used for SDS-PAGE and immunoblot analysis. Similar sample loading on SDS-PAGE lanes was assessed either by Commassie staining of polyacrylamide gels, by Ponceau staining of transferred nitrocellulose membranes, or by immunoblotting with antibodies against Rubisco. See table 2 for details about plasmids for protein expression in plants.

TABLE 2

Nicotina benthamiana expressed nitrogenase realated proteins and their expected sizes

| Plasmids (kDa) | Expressed proteins | Full-length (kDa) | Processed (kDa) |
|---|---|---|---|
| pN2XJ13 | SU9-NifB$_{Av}$-His10 | 64.0 | 56.7 |
| pN2XJ14 | SU9-NifB$_{Mi}$-His10 | 44.3 | 37 |
| pN2XJ15 | SU9-NifB$_{Av}$-GFP | 90.0 | 82.7 |
| pN2XJ16 | SU9-NifB$_{Mi}$-GFP | 70.3 | 63 |
| pN2XJ19 | COX4-twinStrep-GFP | 33.3 | 30.3 |
| pN2XJ20 | COX4-twinStrep- NifB$_{Av}$ | 61.1 | 58.1 |
| pN2XJ21 | COX4-twinStrep- NifB$_{Mi}$ | 41.3 | 38.3 |

Confocal Microscopy of N. Benthamiana in Leaf Tissue

Subcellular localization of fluorescent protein tagged proteins was examined in leaves of A. tumefaciens infiltrated N. Benthamiana using a Leica TCS SP8 laser scanning confocal microscope with a 40×/1.10 water immersion objective equipped with LAS X software (Leica). EGFP, RFP, and chlorophyll were excited with 488-, 561-, or 638-nm laser lines, respectively, with an emission band of 500 to 537 nm for EGFP detection, 585 to 620 nm for RFP detection, and 652 to 727 nm for chlorophyll autofluorescence. EGFP and chlorophyll was recorded simultaneously, while RFP was detected in a separate scan. Laser intensity and gain was maintained during each experiment. For each experiment, specificity of the recorded signals was verified using single transformed cells.

Electron Paramagnetic Resonance Analysis of TS-NifB

TS-NifB preparations in 50 mM Tris-HCl pH 8.0, 300 mM NaCl, 10% glycerol, 2 mM DTH and 5 mM β-ME were prepared for EPR analysis. X-band (9.64 GHz) EPR spectra were recorded on a Bruker E500A spectrometer equipped with an Oxford ESR 910 cryostat for low-temperature measurements. The microwave frequency was calibrated with a frequency counter and the magnetic field with an NMR gaussmeter. The temperature of the X-band cryostat was calibrated with a carbon-glass resistor temperature probe (CGR-1-1000 LakeShore Cryotronics). For all EPR spectra, a modulation frequency and amplitude of 100 kHz and 1 mT were used. The EPR spectra of FIG. 3C and FIG. S9 were recorded at 12K. EPR spectral simulations were performed using the simulation software Spin Count (12). 1 mM Cu(II)EDTA solution is used as spin standard for spin quantification. Two EPR samples independently prepared from two different purifications TS-NifB$^{US}$ and TS-NifB$^{USF}$ were measured. Both purifications yielded identical EPR signals. One set of data are presented in FIG. 3C, and the both sets are presented in FIG. S9.

FdxN and NifU Interaction Assays

NifUAv was expressed and purified from E. coli cells and loaded with [4Fe-4S] cluster as previously described (4). Briefly, 6.0 μM TS-NifBF purified from SB32Y was incubated with NifU (0, 1 or 3 NifU/TS-NifBF molar ratio) in 300 μl reaction mixtures containing 50 mM Tris-HCl pH 8.0, 300 mM NaCl, 10% glycerol, 2 mM DTH and 5 mM β-ME at 30° C. for 30 min. Following NifU incubation, 25 μl Strep-Tactin XT resin (IBA Lifesciences) was added and samples were incubated at 30° C. for additional 60 min. Non-bound proteins were collected from the supernatant following centrifugation at 1,500×g for 2 min. Strep-Tactin bound proteins were washed five times using 1 ml buffer (50 mM Tris-HCl pH 8.0, 300 mM NaCl, 10% glycerol and 5 mM β-ME) and finally eluted using 320 μl buffer supplemented with 50 mM biotin.

Antibodies

Antibodies used in this study and their dilutions for immunoblotting were as follows: polyclonal antibodies detecting NifUAv (used at 1:2,000 in 5% BSA), NifSAv (used at 1:1,000 in 5% BSA), NifBMi (used at 1:2,000 in 5% BSA) were raised against purified preparations of the corresponding A. vinelandii or M. infernus proteins. HA-tag (3F10, 12013819001, Roche, 1:1,000 in 2% non-fat dry milk), Strep-tag II (StrepMAB-Classic, 2-1507-001, IBA Lifesciences, 1:2,000 in 5% BSA), Strep-Tactin conjutaged to HRP (2-1502-001, IBA Lifesciences, 1:50,000 in TBS-T), HSP60 (LK-2, ab59458, Abcam, 1:1,000 in 5% BSA), and Tubulin (3H3087, sc-69971, Santa Cruz Biotechnology, 1:500 in 5% BSA), His-tag (H-3, sc-8036, Santa Cruz), GFP (B-2, sc-9996, Santa Cruz) specific antibodies are commercially available.

Results

NifB His-Tagged Expression, Mitochondria Targeting and Solubility.

Figure 1:
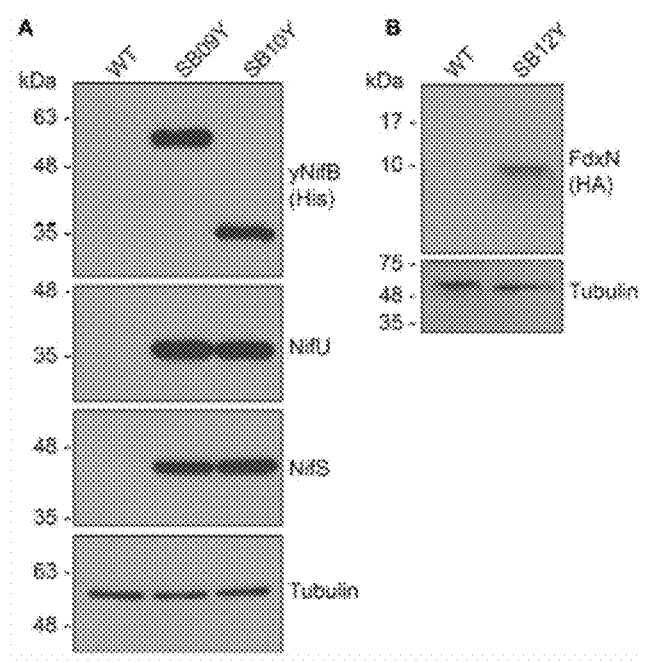
FIG. 1. Expression of NifB, NifU and FdxN proteins in *S. cerevisiae*. (A) Western blot analysis of $NifB_{Av}$ and $NifB_{Mi}$, as well as NifU and NifS, in total protein extracts from strains SB09Y and SB10Y. (B) Western blot analysis of C-terminally HA-tagged FdxN in total protein extract from SB12Y strain. Extracts in (A) and (B) were prepared from aerobically grown cells following galactose induction, and proteins in the extract separated by SDS-PAGE before transferred to membranes. Antibodies recognizing $NifU_{Av}$, $NifS_{Av}$, His epitope, HA epitope, and tubulin were used. Tubulin immunoblot signal intensity is used as loading control.

Western blot analysis of yeast cell-free extracts using antibodies specifically recognizing NifU, NifS, and histidine-tag (for yNifBAv or yNifBMi) confirmed expression of all these proteins in SB09Y and SB10Y strains grown aerobically with galactose as inducer. Protein migrations in SDS-PAGE were consistent with efficient mitochondria leader sequence processing (Table 1 and FIG. 1A). Detection of FdxN in SB09Y and SB10Y was difficult, presumably due to the small size of FdxN (10 kDa) and/or to weak binding of FdxN antibodies generated for this study. An epitope-tagged version of the protein where a C-terminal HA-tag was added to the SU9-FdxN construct was generated and expressed in strain SB12Y (FIG. 1B).

Figure 2:
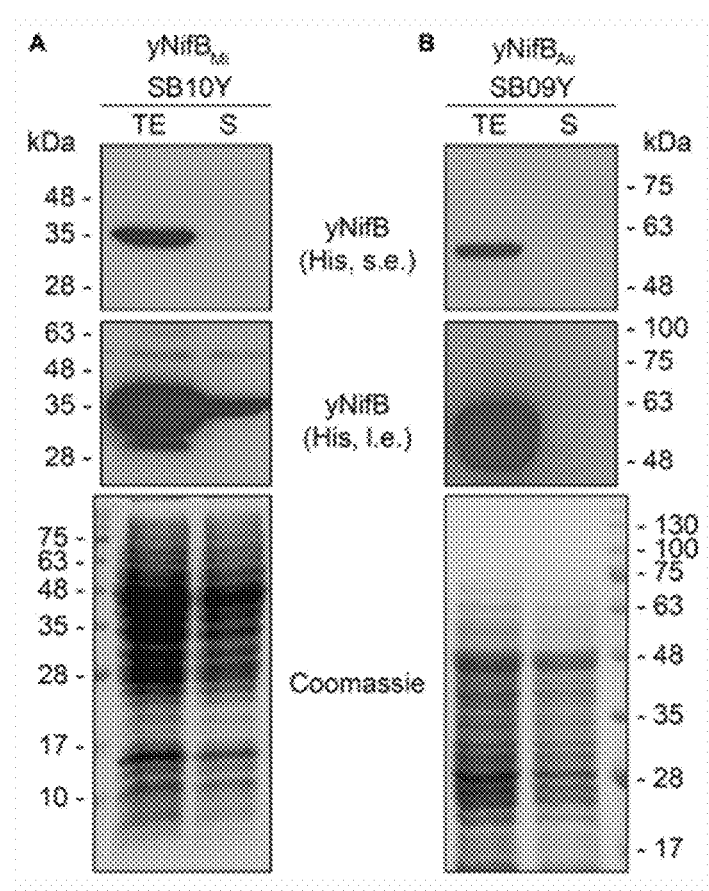
FIG. 2. Solubility of *A. vinelandii* and *M. infernus* NifB proteins expressed in *S. cerevisiae*. (A, B) Western blot analysis of $NifB_{Mi}$ (A) and $NifB_{Av}$ (B) present in total protein extracts (TE) and the soluble fraction (S) of yeast strains SB10Y and SB09Y. Conditions for strain growth, induction of protein expression, total extract preparation, and separation by SDS-PAGE are as in FIG. 1. Antibodies recognizing the His epitope were used. Coomassie stained SDS gels (below) of the protein extracts are included as loading controls.
Figure 3:
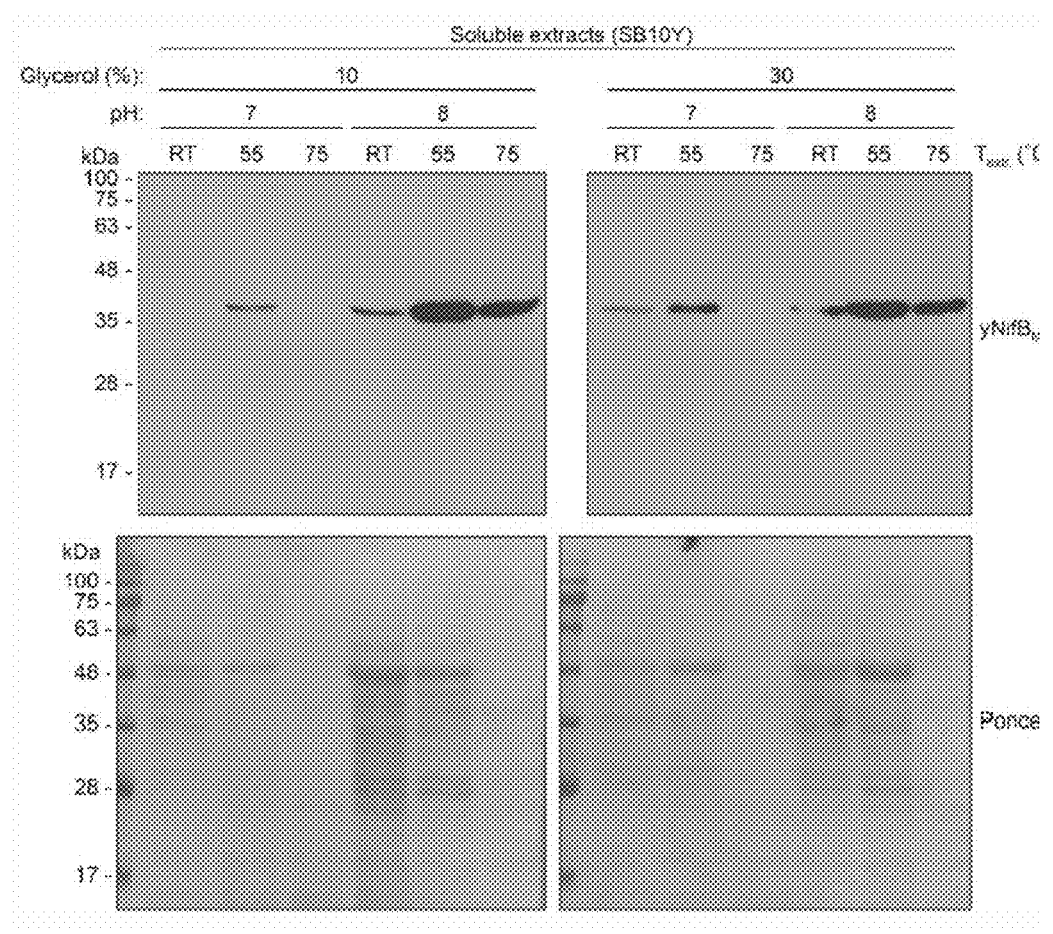
FIG. 3. Levels of soluble yNifBMi in SB10Y obtained by using 12 different extraction conditions. Protein extracts were resolved by SDS-PAGE and then transferred to membranes for immunoblot analysis. Western blot membranes were exposed together on the same film. Ponceau stainings of the same membranes show the levels of total yeast proteins in each extracted sample.
Figure 4:
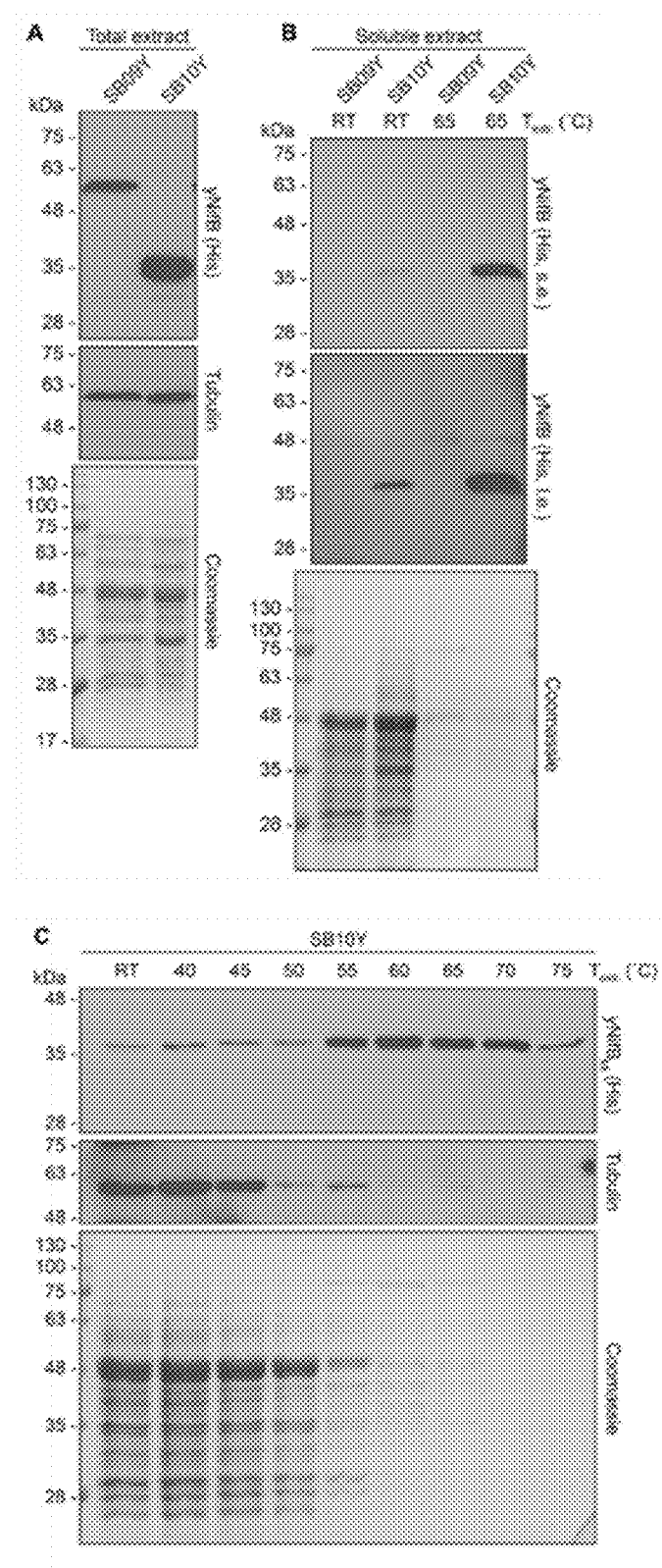
FIG. 4. Levels of soluble $NifB_{Av}$ and $NifB_{Mi}$ in heat-treated yeast extracts. (A, B) Total NifB levels (A) and levels of soluble NifB upon 65° C. heat treatment (B) of protein extracts from yeast expressing $NifB_{Av}$ (SB09Y) or $NifB_{Mi}$ (SB10Y). Antibodies recognizing the His epitope were used. Short (s.e.) and Ions (i.e.) film exposures are shown. RT means room temperature. Tubulin and/or Coomassie stained SDS gels of the same protein extracts are included as loading controls. (C) Western blot analysis of soluble $NifB_{Mi}$ in SB10Y protein extracts upon heat-treatment at increasing temperatures. Heat-induced precipitation of yeast proteins in the extract at the different temperatures is shown using antibodies recognizing tubulin, as well as by Coomassie staining of proteins from the extract resolved by SDS-PAGE.
Figure 5:
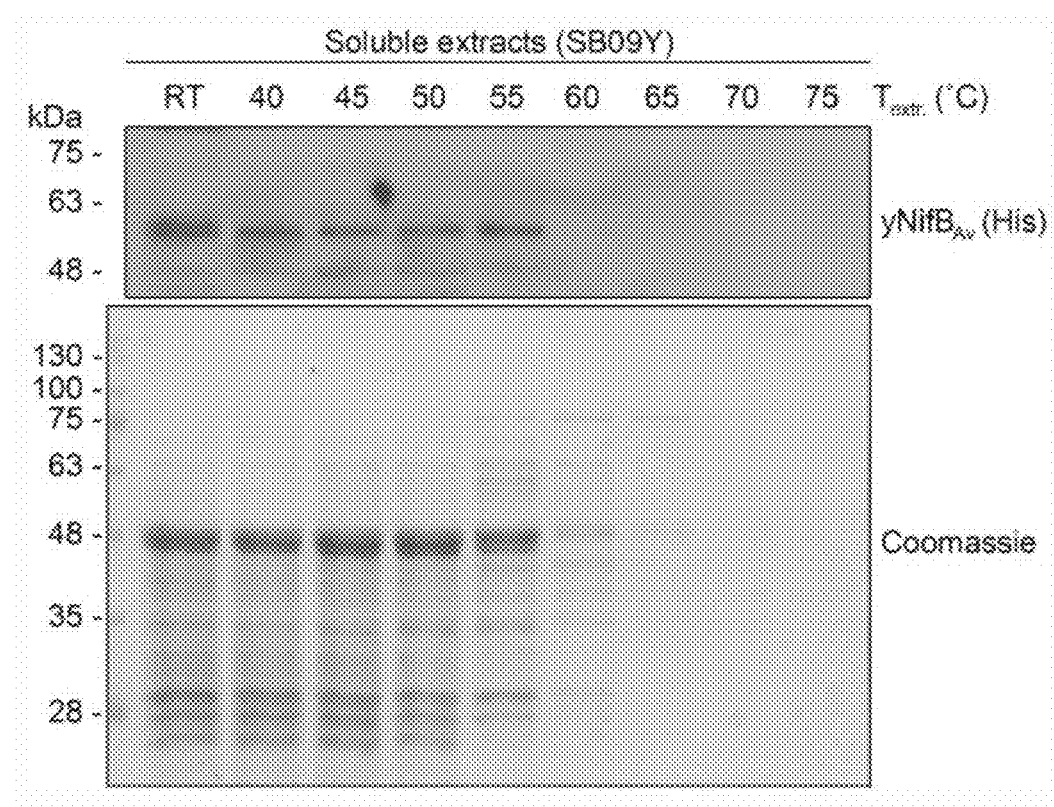
FIG. 5. Levels of soluble yNifBAv upon heat-treatment of SB09Y extracts. SDS-PAGE and Western blot analysis showing levels of soluble yNifBAv in SB09Y protein extracts upon heat-treatment at increasing temperatures. Heat-precipitation of yeast proteins at the different temperatures is shown using Coomassie stained SDS gels loaded with the treated extracts.

Further analysis of the soluble fractions prepared from yeast cells lysed in absence of detergents indicated that most yNifB$_{Mi}$ and nearly all yNifB$_{Mi}$ were of poor solubility (FIG. 2). This suggested that the proteins were either forming insoluble aggregates upon strong expression or interacting with membranes. Exchanging the C-terminal His-tag for an N-terminal variant, and addition of detergents during lysis (see Materials and Methods for details), did not improve conditions were tested (including different temperatures) to screen yNifB$_{Mi}$ solubility and to find a protocol for extraction and enrichment of yNifB$_{Mi}$. While increased concentration of glycerol did not improve solubility, the pH of the extraction buffer was important (FIG. 3). In addition, exposing the total yeast lysate to elevated temperatures before centrifugation not only reduced the amount of total yeast proteins remaining in solution, but also increased the levels of yNifB$_{Mi}$ in the soluble fraction of the extract. Unfortunately, no similar improvement could be obtained for yNifB$_{A}$, (FIGS. 4 A,B and Figure FIG. 5) impairing yNifB$_{Av}$ purifications. Further optimization confirmed that maximum solubility yNifB$_{Mi}$ was obtained at pH 8 upon treatment at 60-65° C. (FIG. 4 C). Therefore 65° C. was chosen for the following yNifB$_{Mi}$ extractions in order to minimize the complexity of the yeast cell-free extracts used for affinity chromatography.

Figure 6:
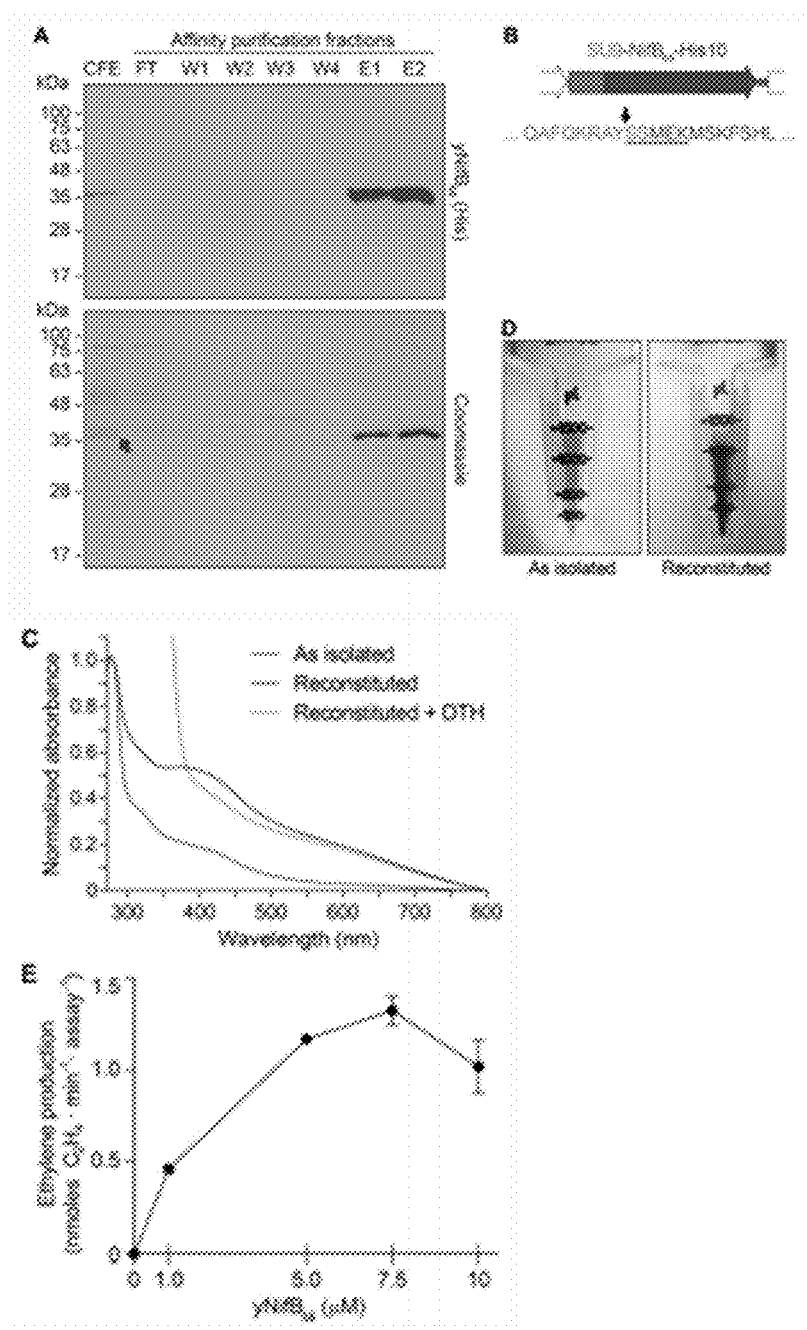
FIG. 6. Purification and biochemical properties of $NifB_{Mi}$. (A) SDS-PAGE and Western blot analysis of $NifB_{Mi}$ purification. CFE, 65° C. heated SB10Y cell-free extract; FT, affinity chromatography flow through; W1-W4 and E1-E2, affinity chromatography wash and elution fractions containing increasing concentrations of imidazole. Arrow in the Coomassie stained panel points to the position of $NifB_{Mi}$ in the gel. (B) SU9 processing site (arrow) of $NifB_{Mi}$. Underlined sequence indicates de N-terminal amino acids of $NifB_{Mi}$ identified by Edman degradation. (C) UV-visible spectra of as isolated, reconstituted, and dithionite (DTH)-reduced reconstitute $NifB_{Mi}$. (D) Typical color of as isolated and reconstituted $NifB_{Mi}$ purified preparations. (E) Titration of FeMo-co synthesis and nitrofenase reconstitution assay with $NifB_{Mi}$. The indicated concentrations of $NifB_{Mi}$ monomer were used. NifB activity was determined by acetylene reduction assay of reconstituted NifDK from ΔnifB *A. vinelandii* UW140 cell-free extracts. Data represent mean±standard deviation (n=2) at each $NifB_{Mi}$ concentration.

Yeast-Expression of his-Tapped NifB$_{Mi}$ is Active in the In Vitro FeMo—Co Synthesis Assay Typical yeast NifB$_{Mi}$ purification (yNifB$_{Mi}$) isolated from SB10Y strain yielded about 4 mg/100 g cell pellet (4.4±1.1, mean and standard deviation from four individual purifications), and NifB$_{Mi}$ was at near purity as determined by SDS-PAGE analysis (FIG. 6 A). To confirm mitochondria import and functionality of the SU9 leader sequence, purified yNifBMi was subjected to N-terminal sequencing. Successful processing of the SU9 sequence was verified, and cleavage appeared at the site predicted from alignment of the SU9 peptide with a reported consensus sequence for yeast mitochondria proteins (Vogtle et al., 2009) (FIG. 6 B).

While as isolated yNifB$_{Mi}$ showed some color and UV-vis absorbance spectrum characteristic of Fe—S protein (3.3±0.8 Fe atoms per monomer from four individual purifications, S not determined), in vitro reconstitution with Fe and S increased color intensity and the 320 and 420 nm features of the UV-vis spectrum indicative of [4Fe—4S] cluster formation (FIGS. 6 C,D). Treatment with dithionite (DTH) reduced absorbance at 420 nm as expected for a redox responsive Fe—S protein. Fe and S content of reconstituted yNifB$_{Mi}$ was consistent with the presence of, at minimum, two [Fe—S] clusters in addition to the SAM-binding [4Fe-4S] cluster (12.5±2.8 Fe and 10.6±3.1 S atoms per monomer; average±standard deviation from four individual purifications). All these features are typical of NifB proteins (Curatti et al., 2006; Wilcoxen et al., 2016).

NifB can be used for in vitro FeMo-co synthesis and nitrogenase reconstitution assays using an Azotobacter vinelandii strain carrying a disrupted nifB gene extract, supplemented with ATP-regenerating mixture, molybdenum (Mo), and homocitrate (Curatti et al., 2006). When in vitro FeMo-co synthesis occurs, de novo-synthesized FeMo-co is incorporated into apo-MoFe nitrogenase present in the extract and activity of reconstituted nitrogenase can be determined by the acetylene reduction assay. To test whether reconstituted yNifBMi was functional, 5 mM protein was added to UW140 extracts lacking NifB-co activity, but providing the rest of the protein components required for FeMo-co synthesis and activatable apo-MoFe nitrogenase. While extract without yNifBMi only showed negligible acetylene reduction, addition of NifB$_{Mi}$ resulted in 40-fold increase in ethylene formation (Table 2). Importantly, yNifB$_{Mi}$ showed similar concentration-dependent activity as purified and reconstituted yNifB from A. vinelandii (Curatti et al., 2006) (FIG. 6 E). The maximum activity appeared to occur at slightly higher concentration (5 mM vs. 1 mM), which could result from slight incompatibility between the yNifB$_{Mi}$ and the other Nif components in the Azotobacter vinelandii strain carrying a disrupted nifB gene extract, as has been shown for NifH (Emerich and Burris, 1976, 1978), or from the suboptimal reaction temperature for the thermophile M. infernus (optimal growth at 85C) NifB protein (Jeanthon et al., 1998). In summary, yNifB$_{Mi}$ exhibits the spectroscopic and catalytic properties of active NifB proteins.

TABLE 3 yNifBMo-dependent in vitro FeMo-co sunthesis and nitrogenase reconstitution assays. Acetylene reduction assays of nitrogenase reconstituted in Azotobacter vinelandii strain extract carrying a disrupted nifB gene. Extracts of extracts supplemented with NifB-co were used as negative and positive controls, respectively. Data represent mean ± standard deviation (n = 2) from four individual yNifB$_{Mi}$ purifications (at 5 uM yNifB$_{Mi}$).

| Azotobacter vinelandii strain carrying a disrupted nifB gene extract | Nmol C$_2$H$_4$ (min– 1 · assay– 1 |
|---|---|
| –NifB-co | 0.04 |
| +NifB-co | 15.54 ± 0.23 |
| +yNifBMi (1) | 1.33 ± 0.22 |
| +yNifBMi (2) | 0.97 ± 0.02 |
| +yNifBMi (3) | 1.92 ± 0.04 |
| +yNifBMi (4) | 1.41 ± 0.06 |

Expression and Mitochondria Targeting of his-Tagged NifB in Plant Leaves

Figure 7:
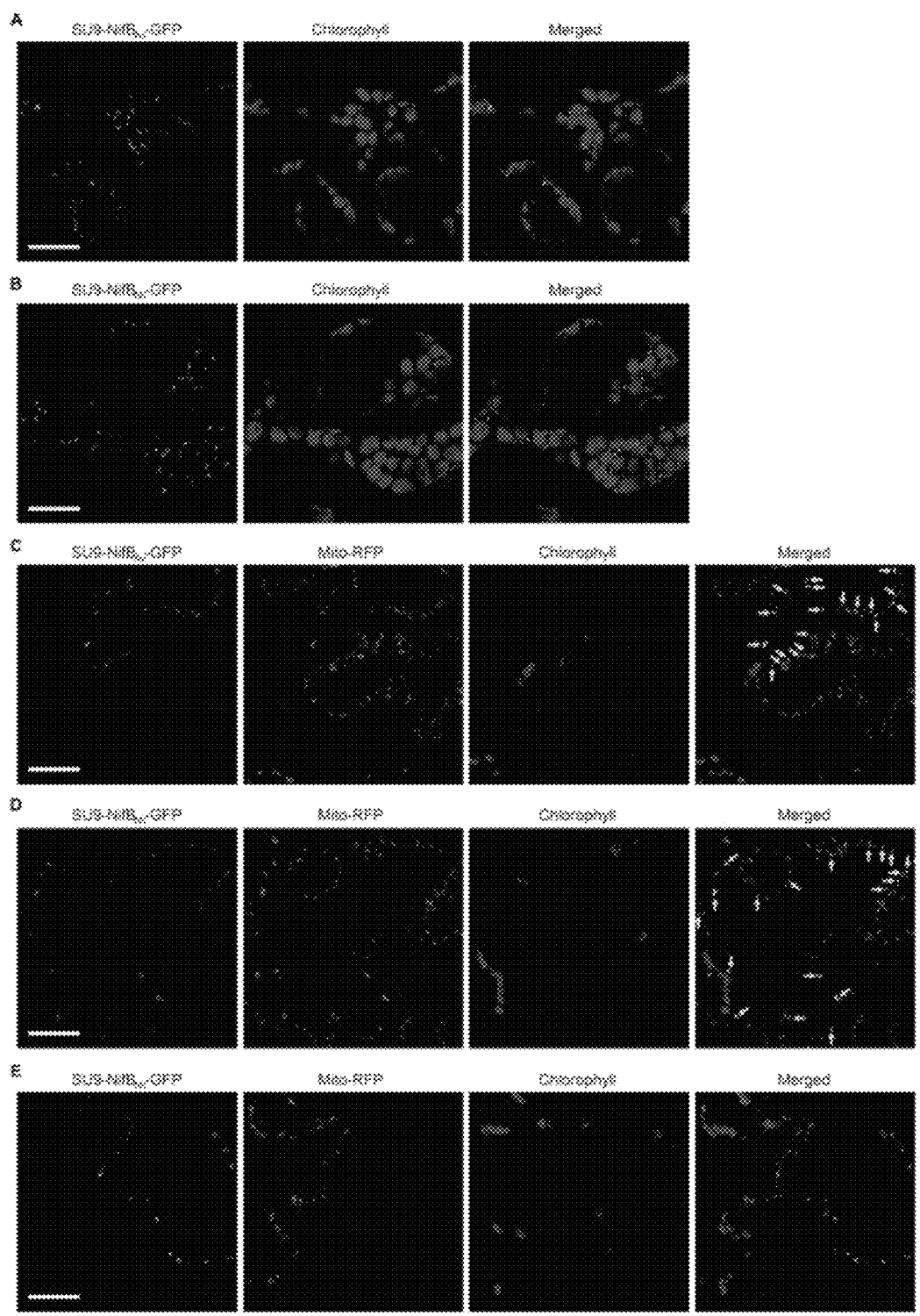
FIG. 7. Expression of mitochondria targeted (SU9) $NifB_{Av}$ and $NifB_{Mi}$ GFP fusions in *N. benthamiana* leaves. (A,B) Mesophyll cells expressing SU9-$NifB_{Av}$-GFP (A) or SU9-$NifB_{Mi}$-GFP (B). GFP (green) and chlorophyll autofluorescence (red) of chloroplasts is shown. (C-E) Epidermal cells expressing SU9-$NifB_{Av}$-GFP (C) and SU9-$NifB_{Mi}$-GFP (D,E), together with a fluorescent mitochondria marker (Mito-RFP). GFP (green), Mito-RFP (magenta) and chlorophyll autofluorescence (red) of chloroplasts is shown. Co-localization of SU9-$NifB_{Ai}$-GFP or SU9-$NifB_{Mi}$-GFP constructs with Mito-RFP labeled structures is shown as white in the merged images, and highlighted with yellow arrows. Adjacent cells expressing SU9-$NofB_{Mi}$-GFP or Mito-RFP are shown as control to verify the specificity of the signal recorded in each channel (E). Scale bars show 30 um.

In order to test whether differences in solubility of plant expressed and mitochondria targeted NifB proteins could be observed, as in yeast, NifB$_{Av}$ and NifB$_{Mi}$ were cloned into plant expression vectors under the control of the constitutive 35S promoter (Table 2). As yeast and tobacco codon usage is similar, no further sequence optimization and gene synthesis was performed. As SU9 is a mitochondria leader sequence from fungi without obvious plant homolog, the C-terminal His-tag of SU9-NifBAv and SU9-NifB$_{Mi}$ was replaced with GFP to track SU9 functionality in N. benthamiana cells. Confocal microscopy analysis showed that SU9 successfully targeted the two NifB variants to the mitochondria of N. benthamiana, as seen from colocalization with a red fluorescent mitochondria marker (Candat et al., 2014) (FIGS. 7A-D). Specific and individual detection of the fluorescent signals was verified from adjacent cells expressing only each one of the constructs (FIG. 7E). Confocal microscopy indicated that the expression level of SU9-NifB$_{Av}$-GFP was lower than SU9-NifB$_{Mi}$-GFP, which was confirmed by Western blot analysis (FIG. 8A). Importantly, SU9-NifB$_{Mi}$-GFP was only detected in the soluble fraction of the extract, in contrast to SU9-NifB$_{Av}$-GFP that could also be seen in the pellet fraction. Migration of the expressed fusion proteins was consistent with correct SU9 leader sequence processing in N. benthamiana cells (FIG. 8A and Table 2). Migration of the plant expressed C-terminally His-tagged versions of the SU9-NifBAv and SU9-NifBMi proteins appeared identical to the corresponding proteins expressed in yeast, supporting that the SU9 leader sequence was processed correctly also in the plant mitochondria (FIGS. 8B,C and FIG. 22).

To enable simultaneous and comparative detection of the two N. benthamiana expressed NifB variants, and to exclude that solubility was affected by the C-terminal GFP moiety, new constructs were generated were the His-tag was exchanged for an N-terminal 28 amino acid Twin-Strep-tag (Schmidt et al., 2013) (FIG. 9). The Twin-Strep-tag is an improved version of the eight amino acid Strep-tag II that was shown superior to His-tag for use with plant tissue replaced by the first 29 amino acids of the yeast cytochrome c oxidase IV (COX4) protein, which has been shown to successfully target proteins to the mitochondria in tobacco and Arabidopsis thaliana (Köhler et al., 1997; Nelson et al., 2007; Pan et al., 2014). As cleavage of COX4 in yeast has been shown to occur between amino acids 25 and 26 (Vogtle et al., 2009), similar processing in N. benthamiana would leave only four amino acids in addition to the Twin-Strep-tag. To verify functionality of the COX4 peptide, and to confirm that the Twin-Strep-tag was not interfering with targeting or solubility, a COX4-twin-Strep-GFP construct was generated (FIG. 9). As expected, COX4 efficiently targeted twin-Strep-GFP to mitochondria in N. benthamiana cells (FIGS. 10 A-C). Specific and individual detection of the fluorescent signals was verified using adjacent cells expressing only one of the constructs (FIG. 10 C).

Both COX4-twin-Strep-NifB$_{Av}$ and COX4-twin-Strep-Nif$_{Bm}$, were readily detected in total protein extracts of A. tumefaciens infiltrated N. benthamiana leaves (FIG. 11 A). To test the solubility of the expressed NifB proteins, total protein extracts were separated in soluble fractions and pellet associated fractions. COX4-twin-Strep-Nif$_{Bm}$, was detected exclusively in the soluble fraction, even upon prolonged exposure (FIG. 11 B). On the contrary, COX4-twin-Strep-NifBAv was more difficult to detect using the Strep-tag II antibody, and appeared to be in the nonsoluble fraction. To verify the identity of the NifBAv protein detected by the Strep-tag II antibody we used NifBAv specific antibody, which confirmed that COX4-twin-Strep-NifB$_{Av}$ was mainly present in the pellet associated fraction (FIG. 11 C).

In summary, we show that mitochondria targeting using SU9 and COX4 resulted in expression of both NifB$_{Av}$ and NifB$_{Mi}$ in leaves of N. benthamiana. Leader sequence processing of all proteins appeared efficient and correct, as only one band of the expected size was detected. Similar to yeast, the NifB$_{Mi}$ protein was more soluble than the corresponding NifB$_{Av}$ variant in N. benthamiana.

Expression and Purification of TS-NifB Carrying [Fe—S] Clusters from Yeast.

Purified NifB$_{Mi}$-His$_{10}$ contained ca. 3 Fe atoms per monomer, in contrast to the 12 Fe atoms expected from a protein with three [4Fe-4S] clusters as NifB. Yeast expressed NifB was therefore only active following [Fe—S] cluster reconstitution, as determined by its ability to complement AnifB A. vinelandii cell-free extracts in the in vitro FeMo-co synthesis assay. The inability to obtain NifB with full cluster complement precluded determining exact genetic requirements for its functional expression in yeast. Therefore, in this experiment, the inventors aimed at analyzing NifB$_{Mi}$ using methods not requiring IMAC resins that could affect [Fe—S] cluster occupancy of the as-isolated protein.

Twin-Strep-tag and mitochondrial matrix leading sequence SU9 were fused to the N-terminus of NifB$_{Mi}$ creating SU9-Twin-Strep-NifB$_{Mi}$ for expression in yeast (hereafter denoted as TS-NifB) (Table1). Analysis of temperature-dependent properties of TS-NifB in SB17Y (TS-NifB co-expressed with mitochondria targeted NifU, NifS and FdxN proteins) showed that the 28 amino acid tag dramatically improved NifB$_{Mi}$ solubility compared to the C-terminally His-tagged counterpart (FIG. 12), suggesting that the Twin-Strep-tag prevented aggregate formation and/or membrane interactions. As TS-NifB could be expressed as a largely soluble protein targeted to the mitochondria of yeast, the influence of presumed NifB accessory proteins NifU, NifS and FdxN could be tested. For this, four new yeast strains were created harboring plasmids for galactose (GAL) induced expression of TS-NifB alone (strain SB30Y, for expression of TS-NifB*), TS-NifB together with NifU and NifS (SB31Y, TS-NifB$^{US}$), TS-NifB with FdxN (SB32Y, TS-NifB$^{F}$), or TS-NifB with FdxN, NifU and NifS (SB33Y, TS-NifB$^{USF}$) (FIG. 13, Table 1). FdxN was equipped with a C-terminal HA-tag to facilitate its detection in yeast protein extracts. All proteins were targeted to mitochondria using SU9 targeting signals (FIG. 14 A), and proper SU9 processing was confirmed by migration on SDS-PAGE (FIG. 14 A, Table 1) and by N-terminal amino acid sequencing of TS-NifB (FIG. 14 B).

TS-NifB from aerated fermenter cultures of yeast cells were purified under anaerobic conditions with yields averaging ca. 6 mg protein per 100 grams of cells (FIGS. 13 B and C, FIG. 15, Table 4), superior to yields previously obtained for NifB$_{Mi}$-His from heat-treated yeast extracts. Analysis of TS-NifB purified from the four strains showed that NifU and NifS significantly increased the amount of Fe co-purifying with TS-NifB, while FdxN-HA had a minor effect on Fe content (Table 4). UV-visible spectra of as-isolated (anaerobic) and air-exposed TS-NifB were consistent with oxygen sensitive [Fe—S] cluster containing proteins (FIGS. 13D and E, FIG. 16). Improved TS-NifB cluster site occupancy from co-expression of NifU and NifS, as seen from increased absorbance at 315 and 400 nm in as-isolated proteins (FIG. 13D), indicate NifB [Fe—S] cluster assembly dependence on NifU and NifS.

TABLE 4

Summary of TS-NifB purifications reported in this work. Purifications, TS-NifB expressing strain and eventual additional expressed proteins, together with the yield of TS-NifB per 100 g cells and Fe per TS-NifB monomer are indicated. Data for average values represent mean ± standard deviation.

| Strain | Expr. Prot. | Pur. | Yield (mg TS-NifB per 100 g cells) | Fe (per TS-NifB monomer) | Yield$_{av}$ (mg TS-NifB per 100 g cells) | Fe$_{av}$ (per TS-NifB monomer) |
|---|---|---|---|---|---|---|
| SB30Y | B | 1 | 4.67 | 2.10 | 6.38 ± 1.49 | 2.01 ± 0.13 |
|  |  | 6 | 7.42 | 1.86 |  |  |
|  |  | 7 | 7.05 | 2.07 |  |  |
| SB31Y | B U S | 2 | 5.68 | 4.95 | 6.16 ± 0.59 | 5.02 ± 0.12 |
|  |  | 3 | 5.69 | 4.93 |  |  |
|  |  | 8 | 7.02 | 5.02 |  |  |
|  |  | 9 | 5.95 | 5.19 |  |  |

TABLE 4-continued

Summary of TS-NifB purifications reported in this work. Purifications, TS-NifB expressing strain and eventual additional expressed proteins, together with the yield of TS-NifB per 100 g cells and Fe per TS-NifB monomer are indicated. Data for average values represent mean ± standard deviation.

| Strain | Expr. Prot. | Pur. | Yield (mg TS-NifB per 100 g cells) | Fe (per TS-NifB monomer) | Yield$_{av}$ (mg TS-NifB per 100 g cells) | Fe$_{av}$ (per TS-NifB monomer) |
|---|---|---|---|---|---|---|
| SB32Y | B F | 4 | 7.17 | 2.34 | 6.52 ± 0.84 | 2.22 ± 0.30 |
|  |  | 5 | 6.82 | 2.43 |  |  |
|  |  | 11 | 5.57 | 1.87 |  |  |
| SB33Y | B U S F | 10 | 7.43 | 6.43 | 6.26 ± 1.46 | 6.11 ± 0.89 |
|  |  | 12 | 4.37 | 4.87 |  |  |
|  |  | 13 | 7.38 | 6.98 |  |  |
|  |  | 14 | 5.87 | 6.16 |  |  |

In Vitro FeMo—Co Synthesis Assay and Reconstitution of Apo-NifDK Using ΔnifB *A. vinelandii* Cell-Free Extracts.

TS-NifB activities were tested by the in vitro FeMo-co synthesis assay and reconstitution of apo-NifDK using ΔnifB *A. vinelandii* cell-free extracts. Although FdxN-HA did not significantly influence Fe content (Table 4), activity of as-isolated TS-NifB showed critical dependence of co-expressed FdxN-HA (FIG. 17 A).

In Vitro FeMo—Co Synthesis and Apo-NifDK Reconstitution

Activity of TS-NifB$^{USF}$ was further specified using the minimal protein constituents required for in vitro FeMo-co synthesis (FIG. 19)). A dose-dependent increase in apo-NifDK activation was observed using TS-NifB$^{USF}$ (FIG. 17 B) combined with apo-Nif EN, NifH, apo-NifDK and NifX in a reaction additionally containing Fe, S, S-adenosyl methionine (SAM), molybdate, R-homocitrate, sodium dithionite (DTH) and Mg-ATP. To further understand the biochemical characteristics of yeast expressed TS-NifB$^{USF}$, components required for NifB-co biosynthesis (Fe, S and SAM) were individually tested (FIG. 17 C). No activity was detected when SAM was absent. Presence of sulfide did not affect TS-NifB$^{USF}$ activity, while elimination of Fe reduced apo-NifDK activation to half. These properties are consistent with functional protein carrying NifB-co [4Fe-4S] cluster precursors. The apparent independence from exogenously added sulfide could also be explained by S species originating from breakdown of the DTH present in the reaction mixture.

Genetic and Biochemical Requirements for TS-NifB Functionality

FdxN was previously shown to be involved in FeMo-co biosynthesis, with a suggested role of donating electrons required for NifB-co synthesis. To understand how FdxN-HA enhanced TS-NifB activity we tested whether FdxN-HA was present in purified preparations of TS-NifBF and TS-NifBUSF. While negligible amounts of FdxN-HA and NifU were found in active TS-NifBUSF purifications, FdxN-HA was consistently found with inactive TS-NifBF (FIG. 18A, FIG. 20). This observation ruled out the requirement of FdxN during NifB-co formation, and indicated a possible prior effect over NifB in vivo. Because NifB [4Fe-4S] cluster reconstitution was not required for its activity when co-expressed with FdxN, a prior role in NifB cluster acquisition or maturation was hypothesized. As FdxN-HA did not significantly increase the Fe content bound to TS-Nif B per se, but instead affected TS-NifB activity (FIG. 17A), one explanation could be that FdxN exerted its action on [Fe—S] clusters delivered to NifB by NifU, and was subsequently released from NifB. FdxN could dock at NifB and await [Fe—S] cluster donation by NifU, a hypothesis we tested in vitro, using Strep-Tactin-immobilized TS-NifBF. When this TS-NifBF was exposed to NifU (purified from *Escherichia coli* and loaded with [4Fe-4S] clusters) we observed a dose-dependent decrease in TS-NifBF associated with FdxN-HA (FIG. 18B).

As-isolated TS-NifB$^{US}$ and TS-NifB$^{USF}$ were further analyzed by electronic paramagnetic resonance (EPR). The EPR spectrum of the as-isolated TS-NifB$^{USF}$ measured at 12 K exhibited S=½ signals typical of reduced 4Fe4S ([Fe$_4$S$_4$]$^+$) clusters (FIG. 18C). This assignment was confirmed by temperature dependent measurements, which showed signal disappearance above 70 K (FIG. 21). The signal was well reproduced by including three different [Fe$_4$S$_4$]$^+$ clusters in spectral simulations (FIG. 18C), with g values almost identical to those of the clusters found in the reconstituted *M. infernus* NifB expressed in *E. coli*. Total spin concentration of the S=½ [Fe$_4$S$_4$]+ signals was ~1.5 mM, which translates to ~6 mM Fe. The EPR determined Fe concentration is in good agreement with biochemical Fe determination (~7 mM), indicating that almost all Fe in TS-NifB$^{USF}$ was in the form of [Fe$_4$S$_4$]$^+$ clusters. In contrast, only one type of [Fe$_4$S$_4$]$^+$ clusters (AC1 cluster) was observed in the EPR spectrum of as-isolated TS-NifB$^{US}$ (FIG. 18C), while clusters RS and AC2 were missing. These observations provide strong correlation between FdxN function, NifB [Fe—S] cluster composition, and activity.

What is claimed is:

1. A method for expressing a functional NifB protein in a eukaryotic cell comprising the steps of:
   i) introducing into said cell a polynucleotide encoding a fusion protein comprising NifB protein and a mitochondrial targeting peptide, a polynucleotide encoding a fusion protein comprising NifU and a mitochondrial targeting peptide, a polynucleotide encoding a fusion protein comprising NifS and a mitochondrial targeting peptide, and a polynucleotide encoding a fusion protein comprising fdxN and a mitochondrial targeting peptide,
   ii) growing said cell under conditions allowing the expression of said protein and, if desired,
   iii) purifying said protein under anaerobic conditions, wherein the resulting NifB protein has metal clusters containing at least 6 Fe atoms per monomer of protein.

2. A method for expressing a functional NifB protein in a eukaryotic cell comprising the steps of:
   iv) introducing into said cell an expression vector comprising a polynucleotide encoding a fusion protein comprising NifB protein and a mitocondrial targeting peptide, an expression vector comprising a polynucleotide encoding a fusion protein comprising NifU and a mitochondrial targeting peptide, an expression vector comprising a polynucleotide encoding a fusion protein comprising NifS and a mitochondrial targeting peptide, and an expression vector comprising a polynucleotide encoding a fusion protein comprising fdxN and a mitochondrial targeting peptide,
   v) growing said cell under conditions allowing the expression of said protein and, if desired,
   vi) purifying said protein under anaerobic conditions, wherein the resulting NifB protein has metal clusters containing at least 6Fe atoms per monomer of protein.

3. The method according to claim 1, wherein the polynucleotide further comprises at least one peptide tag adequate for detection or purification of the fusion protein.

4. The method according to claim 3, wherein the peptide tag is N-terminal to NifB and wherein the mitochondrial targeting peptide is N-terminal to said peptide tag.

5. The method according to claim 3, wherein the mitochondrial targeting peptide is the polypeptide sequence of SEQ ID NO: 1 or SEQ ID NO: 2.

6. The method according to claim 3, wherein the tag peptide is the polypeptide sequence of SEQ ID NO: 3.

7. The method according to claim 2, wherein the polynucleotide further comprises at least one peptide tag adequate for detection or purification of the fusion protein.

8. The method according to claim 7, wherein the peptide tag is N-terminal to NifB and wherein the mitochondrial targeting peptide is N-terminal to said peptide tag.

9. The method according to claim 7, wherein the mitochondrial targeting peptide is the polypeptide sequence of SEQ ID NO: 1 or SEQ ID NO: 2.

10. The method according to claim 7, wherein the tag peptide is the polypeptide sequence of SEQ ID NO: 3.

* * * * *

UNITED STATES PATENT AND TRADEMARK OFFICE
CERTIFICATE OF CORRECTION

PATENT NO. : 10,941,428 B2
APPLICATION NO. : 16/161487
DATED : March 9, 2021
INVENTOR(S) : Luis Manuel Rubio Herrero et al.

Page 1 of 8

It is certified that error appears in the above-identified patent and that said Letters Patent is hereby corrected as shown below:

On the Title Page

Column 2, Item (56), Line 5, under Other Publications, delete "Cofractor" and insert --Cofactor--.

Column 2, Item (56), Line 24, under Other Publications, delete "Nitorgenase" and insert --Nitrogenase--.

Column 2, Item (56), Line 24, under Other Publications, delete "Azotbacter:" and insert --Azotobacter:--.

Column 2, Item (56), Line 32, under Other Publications, delete "Nitorgenase" and insert --Nitrogenase--.

On Page 2, Column 1, Item (56), Line 10, under Other Publications, delete "Aradiopsis" and insert --Arabidopsis--.

On Page 2, Column 1, Item (56), Line 19, under Other Publications, delete "Nif-B" and insert --NifB--.

On Page 2, Column 1, Item (56), Line 46, under Other Publications, delete "Hemopietic" and insert --Hematopoietic--.

On Page 3, Column 1, Item (56), Line 20, under Other Publications, delete "(Sarracenia purp urea)," and insert --(Sarracenia purpurea),--.

On Page 3, Column 1, Item (56), Line 23, under Other Publications, delete "Nitrogenas" and insert --Nitrogenase--.

On Page 3, Column 1, Item (56), Line 25, under Other Publications, delete "Nififdxnrnfoq" and insert --nifBfdxNnifOQ--.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,941,428 B2

On Page 3, Column 1, Item (56), Line 33, under Other Publications, delete "Rubio, L." and insert --Rubio, L.,--.

On Page 3, Column 1, Item (56), Line 44, under Other Publications, delete "Nitro-Genase" and insert --Nitrogenase--.

On Page 3, Column 1, Item (56), Line 44, under Other Publications, delete "Aztobacter" and insert --Azotobacter--.

On Page 3, Column 2, Item (56), Line 3, under Other Publications, delete "Nicotania" and insert --Nicotiana--.

On Page 3, Column 2, Item (56), Line 4, under Other Publications, delete "Escherichi" and insert --Escherichia--.

On Page 3, Column 2, Item (56), Line 6, under Other Publications, delete "Uid a" and insert --uidA--.

On Page 3, Column 2, Item (56), Line 12, under Other Publications, delete "Dipolid" and insert --Diploid--.

In the Specification

In Column 1, Line 53, delete "Azotobactereceae," and insert --Acetobacteraceae,--.

In Column 2, Line 34, delete "invention." and insert --invention,--.

In Column 3, Line 31, delete "proteins." and insert --proteins,--.

In Column 3, Line 63, delete "stainings" and insert --staining--.

In Column 4, Line 4, delete "Ions" and insert --long--.

In Column 4, Line 34, delete "nitrofenase" and insert --nitrogenase--.

In Column 4, Line 50, delete "SU9-NifB$_{Ai}$" and insert --SU9-NifB$_{Av}$--.

In Column 4, Line 57, delete "NifB$_{AV}$" and insert --NifB$_{Av}$--.

In Column 4, Line 60, delete "SU9-NifB$_{Ai}$" and insert --SU9-NifB$_{Av}$--.

In Column 4, Line 64, delete "SU9-NifBAv" and insert --SU9-NifB$_{Av}$--.

In Column 4, Line 67, delete "NifB$_{AV}$" and insert --NifB$_{Av}$--.

In Column 5, Line 2, delete "Nis10" and insert --His10--.

CERTIFICATE OF CORRECTION (continued)
U.S. Pat. No. 10,941,428 B2

In Column 6, Line 12, delete "TS-NifB<sup>us</sup>" and insert --TS-NifB*--.

In Column 6, Line 13, delete "TS-Nif Bus" and insert --TS-NifB<sup>us</sup>--.

In Column 6, Line 39, delete "(D)" and insert --(D).--.

In Column 7, Line 16 (Approx.), delete "Nif U." and insert --NifU.--.

In Column 7, Line 18 (Approx.), delete "Streptactin" and insert --Strep-Tactin--.

In Column 7, Line 19 (Approx.), delete "TS-Nif BUS" and insert --TS-NifBUS--.

In Column 7, Line 35 (Approx.), delete "extact;" and insert --extract;--.

In Column 8, Line 51, delete "omithinolytica" and insert --ornithinolytica--.

In Column 8, Line 64, delete "(A0A011U198)," and insert --(A0A011Ul98),--.

In Column 8, Line 65, delete "(AOLH03)," and insert --(A0LH03),--.

In Column 12, Line 7, delete "tag" and insert --tag.--.

In Column 12, Line 33, delete "resourfin" and insert --resorufin--.

In Column 12, Line 42, delete "tagan" and insert --tag an--.

In Column 12, Lines 45-46, delete "3-galactosidase" and insert --β-galactosidase--.

In Column 13, Line 7, delete "resoruf in" and insert --resorufin--.

In Column 15, Line 1, delete "(the a" and insert --(the α--.

In Column 15, Line 49, delete "Acti" and insert --Act1--.

In Column 15, Line 52, delete "comalina" and insert --commelina--.

In Column 16, Line 1, delete "5,378,619)," and insert --5,378,619).--.

In Column 16, Line 32, delete "P. stiptis," and insert --P. stipitis,--.

In Column 16, Line 35, delete "wickeramii," and insert --wickerhamii,--.

In Column 16, Line 36, delete "thernotolerans," and insert --thermotolerans,--.

In Column 16, Line 37, delete "reesia," and insert --reesei,--.

CERTIFICATE OF CORRECTION (continued)
U.S. Pat. No. 10,941,428 B2

In Column 16, Line 38, delete "Totypocladium," and insert --Tolypocladium,--.

In Column 16, Line 45, delete "luchiowense," and insert --lucknowense,--.

In Column 17, Line 35 (Approx.), delete "Nicotina" and insert --Nicotiana--.

In Column 17, Line 37 (Approx.), delete "cerevisae" and insert --cerevisiae--.

In Column 18, Line 17 (Approx.), delete "partening" and insert --partnering--.

In Column 22, Line 46 (Approx.), delete "et al," and insert --et al.--.

In Column 23, Line 6, delete "cerevisae of Nicotina" and insert --cerevisiae of Nicotiana--.

In Column 23, Line 36, delete "is is" and insert --is--.

In Column 28, Line 22, delete "mitrotracker" and insert --mitotracker--.

In Column 28, Line 25, delete "MitoTrackerR" and insert --MitoTracker®--.

In Column 28, Line 27, delete "MitoTrackerR" and insert --MitoTracker®--.

In Column 28, Line 28, delete "MitoTrackerR dyes, MitoTrackerR" and insert --MitoTracker® dyes, MitoTracker®--.

In Column 28, Line 29, delete "MitoTrackerR" and insert --MitoTracker®--.

In Column 28, Line 65, delete "DNaseI" and insert --DNase I--.

In Column 29, Line 30, delete "a of" and insert --a--.

In Column 30, Line 59, delete "fe" and insert --Fe--.

In Column 31, Line 58, delete "asparate" and insert --aspartate--.

In Column 32, Lines 33-34, delete "S-Transferase tagMaltose" and insert --S-Transferase-tag, Maltose--.

In Column 32, Line 55, delete "1 or 2" and insert --1 or 2.--.

In Column 36, Line 40 (Approx.), delete "invention" and insert --invention.--.

In Column 38, Line 14, delete "ENa$_2$B$_2$." and insert --EN$\alpha_2\beta_2$.--.

In Column 38, Line 16, delete "the a" and insert --the--.

CERTIFICATE OF CORRECTION (continued)
U.S. Pat. No. 10,941,428 B2

In Column 38, Line 16, delete "ENa₂B₂" and insert --ENα₂β₂--.

In Column 38, Line 17, delete "ENa₂B₂" and insert --ENα₂β₂--.

In Column 38, Line 39, delete "(AIS31022.11 )," and insert --(AIS31022.1I),--.

In Column 38, Line 40, delete "(WP_018701501.11)" and insert --(WP_018701501.1I)--.

In Column 39, Line 6, delete "(WP_011744626.11)," and insert --(WP_011744626.1I),--.

In Column 39, Line 7, delete "(WP_009565928.11)," and insert --(WP_009565928.1I),--.

In Column 39, Line 22, delete "syntethase," and insert --synthetase,--.

In Column 39, Line 24, delete "molibdate" and insert --molybdate--.

In Column 39, Line 33, delete "molibdate" and insert --molybdate--.

In Column 40, Lines 6-7, delete "leptomitiform is (WP_062149047.11)" and insert --leptomitiformis (WP_062149047.11)--.

In Column 40, Line 53, delete "Nif H," and insert --NifH,--.

In Column 41, Lines 8-18, delete "The A. vinelandii......zole." and insert the same in Column 41, Line 7 as the continuation of same paragraph.

In Column 41, Line 11, delete "Co²⁺-affinity" and insert --Co2+-affinity--.

In Column 41, Line 24, delete "strain" and insert --strain.--.

In Column 42, Lines 2-3, delete "apo-Nif EN," and insert --apo-NifEN,--.

In Column 42, Line 24, delete "Nif H," and insert --NifH,--.

In Column 42, Line 47 (Approx.), delete "Nif H," and insert --NifH,--.

In Column 42, Line 67, delete "proteins." and insert --proteins,--.

In Column 45, Line 28, delete "Nif H," and insert --NifH,--.

In Column 45, Line 56, delete "DH5a" and insert --DH5α--.

In Column 46, Line 4, delete "Nis10" and insert --His10--.

In Column 46, Line 4, delete "5% and 3%" and insert --5'- and 3'- --.

CERTIFICATE OF CORRECTION (continued)
U.S. Pat. No. 10,941,428 B2

In Column 46, Line 7, delete "5% ATTT" and insert --5'- ATTTT--.

In Column 46, Line 8, delete "5%" and insert --5'- --.

In Column 46, Line 10, delete "5%" and insert --5'- --.

In Column 46, Line 11, delete "5%" and insert --5'- --.

In Column 46, Line 14, delete "5%" and insert --5'- --.

In Column 46, Line 18, delete "Nis10," and insert --His10,--.

In Column 46, Line 18, delete "5%" and insert --5'- --.

In Column 46, Line 22, delete "5%" and insert --5'- --.

In Column 46, Line 23, delete "5%" and insert --5'- --.

In Column 46, Line 24, delete "5%" and insert --5'- --.

In Column 46, Line 28, delete "5%" and insert --5'- --.

In Column 46, Line 32, delete "Nis10," and insert --His10,--.

In Column 46, Line 42, delete "5%" and insert --5'- --.

In Column 46, Line 44, delete "5%" and insert --5'- --.

In Column 46, Line 49, delete "5"" and insert --5'- --.

In Column 48, Lines 43-44, delete "Commassie" and insert --Coomassie--.

In Column 49, Lines 9-10, delete "b-mercaptoethanol (b-ME)," and insert --β-mercaptoethanol (β-ME),--.

In Column 49, Line 12, delete "0.5 mmglass" and insert --0.5 mm glass--.

In Column 49, Line 23, delete "(TS-Nif B)" and insert --(TS-NifB)--.

In Column 49, Line 27, delete "05" and insert --C5--.

In Column 50, Lines 14-17 (Approx.), delete "Coomassie staining...... liquid $N_2$." and insert the same in Column 50, Line 13 (Approx.) as the continuation of the same paragraph.

In Column 51, Line 33, delete "(CoyLabs)" and insert --(Coy Labs)--.

CERTIFICATE OF CORRECTION (continued)
U.S. Pat. No. 10,941,428 B2

In Column 52, Line 1, delete "Nif EN" and insert --NifEN--.

In Column 52, Line 27, delete "5%" and insert --5'- --.

In Column 52, Line 37, delete "5%" and insert --5'- --.

In Column 52, Line 43, delete "5%" and insert --5'- --.

In Column 52, Line 44, delete "5%" and insert --5'- --.

In Column 52, Line 59, delete "5%" and insert --5'- --.

In Column 52, Line 60, delete "5%" and insert --5'- --.

In Column 53, Line 29 (Approx.), delete "tuve" and insert --tube--.

In Column 53, Lines 48-49, delete "Commassie" and insert --Coomassie--.

In Column 53, Line 56, delete "Nicotina" and insert --Nicotiana--.

In Column 53, Line 57, delete "realated" and insert --related--.

In Column 54, Line 61, delete "conjutaged" and insert --conjugated--.

In Column 55, Line 19, delete "yNifB$_{Mi}$" and insert --yNifB$_{Av}$--.

In Column 55, Line 35, delete "yNifB$_A$," and insert --yNifB$_{Av}$--.

In Column 56, Line 35, delete "sunthesis" and insert --synthesis--.

In Column 56, Line 37, delete "NifUAv" and insert --NifU$_{Av}$--.

In Column 56, Line 55, delete "NifUAv" and insert --NifU$_{Av}$--.

In Column 56, Line 55, delete "NifSAv" and insert --NifS$_{Av}$--.

In Column 56, Line 61, delete "SU9-NifBAv" and insert --SU9-NifB$_{Av}$--.

In Column 57, Line 41, delete "Nif$_{Bm}$," and insert --NifB$_{Mi}$--.

In Column 57, Line 45, delete "Nif$_{Bm}$," and insert --NifB$_{Mi}$--.

In Column 57, Line 48, delete "NifBAv" and insert --NifB$_{Av}$--.

In Column 57, Line 51, delete "NifBAv" and insert --NifB$_{Av}$--.

CERTIFICATE OF CORRECTION (continued)
U.S. Pat. No. 10,941,428 B2

In Column 57, Line 63, delete "$His_{10}$" and insert --His10--.

In Column 57, Line 67, delete "AnifB" and insert --$\Delta$nifB--.

In Column 59, Line 33 (Approx.), delete "119))." and insert --119).--.

In Column 59, Line 34 (Approx.), delete "apo-Nif EN," and insert --apo-NifEN,--.

In Column 60, Line 17 (Approx.), delete "TS-Nif B" and insert --TS-NifB--.

In Column 60, Line 31 (Approx.), delete "S='/2" and insert --S=1/2--.

In the Claims

In Column 93, Claim 2, Line 56 (Approx.), delete "mitocondrial" and insert --mitochondrial--.

In Column 94, Claim 2, Line 40, delete "6Fe" and insert --6 Fe--.